(12) United States Patent
Casado Izquierdo et al.

(10) Patent No.: US 12,282,021 B2
(45) Date of Patent: Apr. 22, 2025

(54) STRATIFICATION OF ACUTE MYELOID LEUKAEMIA PATIENTS FOR SENSITIVITY TO KINASE PATHWAY INHIBITOR THERAPY

(71) Applicant: KINOMICA LIMITED, Macclesfield (GB)

(72) Inventors: Pedro Maria Casado Izquierdo, London (GB); Pedro Rodriquez Cutillas, London (GB)

(73) Assignee: KINOMICA LIMITED, Macclesfield (GB)

(*) Notice: Subject to any disclaimer, the term of this patent is extended or adjusted under 35 U.S.C. 154(b) by 644 days.

(21) Appl. No.: 16/624,549

(22) PCT Filed: Jun. 20, 2018

(86) PCT No.: PCT/EP2018/066472
§ 371 (c)(1),
(2) Date: Dec. 19, 2019

(87) PCT Pub. No.: WO2018/234404
PCT Pub. Date: Dec. 27, 2018

(65) Prior Publication Data
US 2020/0393466 A1    Dec. 17, 2020

(30) Foreign Application Priority Data

Jun. 21, 2017 (GB) .................... 1709917

(51) Int. Cl.
G01N 33/574 (2006.01)
A61K 31/519 (2006.01)
A61K 31/553 (2006.01)

(52) U.S. Cl.
CPC ..... *G01N 33/57426* (2013.01); *A61K 31/519* (2013.01); *A61K 31/553* (2013.01); *G01N 2440/14* (2013.01)

(58) Field of Classification Search
CPC ............... A61K 31/519; A61K 31/553; G01N 2440/14; G01N 2800/52; G01N 33/57426
See application file for complete search history.

(56) References Cited

U.S. PATENT DOCUMENTS

2010/0009364 A1    1/2010 Fantl et al.

FOREIGN PATENT DOCUMENTS

WO    2016193745    12/2016
WO    WO-2017214433 A1 * 12/2017    ......... A61K 31/4709

OTHER PUBLICATIONS

Hauswirth et al. European Journal of Clinical Investigation, 2007, 37, pp. 73-82. (Year: 2007).*

Bain et al., "The selectivity of protein kinase inhibitors: a further update", Biochem J, 2007, 408, pp. 297-315.
Bennett et al., "Proposed Revised Criteria for the Classification of Acute Myeloid Leukemia", Annals of Internal Medicine, 1985, 103, pp. 626-629.
Burgess et al., "Preclinical efficacy of MEK inhibition in Nras-mutant AML", Blood, 2014, 124(26), pp. 3947-3955.
Casado et al., "Phosphoproteomics data classify hematological cancer cell lines according to tumor type and sensitivity to kinase inhibitors", Genome Biology, 2013, 14(R37), pp. 1-18.
Casado et al., "Kinase-Substrate Enrichment Analysis Provides Insights into the Heterogeneity of Signaling Pathway Activation in Leukemia Cells", Science Signaling, 2013, 6(268 rs6), pp. 1-14.
Casado et al., "Differentiation Status Revealed By Shotgun Phosphoproteomics Determines Sensitivity of Primary AML Cells to Kinase Inhibitors", Blood, 2016, 128(840), pp. 1-4.
Casado et al., "Proteomic and genomic integration identifies kinase and differentiation determinants of kinase Inhibitor sensitivity in leukemia cells", Leukemia, 2018, 32, pp. 1818-1822.
Gruhler et al., "Quantitative Phosphoproteomics Applied to the Yeast Pheromone Signaling Pathway", Molecular & Proteomics, 2005, 4(3), pp. 310-327.
Hastie et al., "Assay of protein kinases using radiolabled ATP: a protocol", Nature Protocols, 2006, 1(2), pp. 968-971.
Larsen et al., "Highly Selective Enrichment of Phosphorylated Peptides from Peptide Mixtures Using Titanium Dioxide Microcolumns", Molecular & Cellular Proteomics, 2005, 4(7), pp. 873-886.
Montoya et al., "Characterization of a TiO2 enrichment method for label-free quantitative phosphoproteomics", Methods, 2011, 54(4), pp. 370-378.
Perkins et al., "Probability-based protein identification by searching sequence databases using mass spectrometry data", Electrophoresis, 1999, 20, pp. 3551-3567.
Vizcaino et al., "2016 update of the PRIDE database and its related tools", Nucleic Acids Research, 2016, 44, pp. D447-D456.
Wilkes et al., "Empirical inference of circuitry and plasticity in a kinase signaling network", PNAS, 2015, 112(25), pp. 7719-7724.
Yohe, "Molecular Genetic Markers in Acute Myeloid Leukemia", J Clin Med, 2015, 4, pp. 460-478.

(Continued)

*Primary Examiner* — Kara R. McMillian
(74) *Attorney, Agent, or Firm* — Perkins Coie LLP; Viola Kung; Andrew T. Pettit

(57) ABSTRACT

The invention relates to the treatment of acute myeloid leukaemia (AML) in patients. In particular, the invention concerns improved methods for identifying AML patients who may be effectively treated with kinase pathway inhibitors, and improved methods for predicting whether a kinase pathway inhibitor may be efficacious for treatment of AML in an individual patient. The invention also comprehends a method of screening a plurality of patients suffering from acute myeloid leukaemia, to determine whether the acute myeloid leukaemia of any one or more of the patients may be effectively treated with a kinase pathway inhibitor. The invention further provides methods for the treatment of such patients with kinase pathway inhibitors, and kinase pathway inhibitors for use in such methods.

1 Claim, 14 Drawing Sheets

(56) References Cited

OTHER PUBLICATIONS

Figure 1:
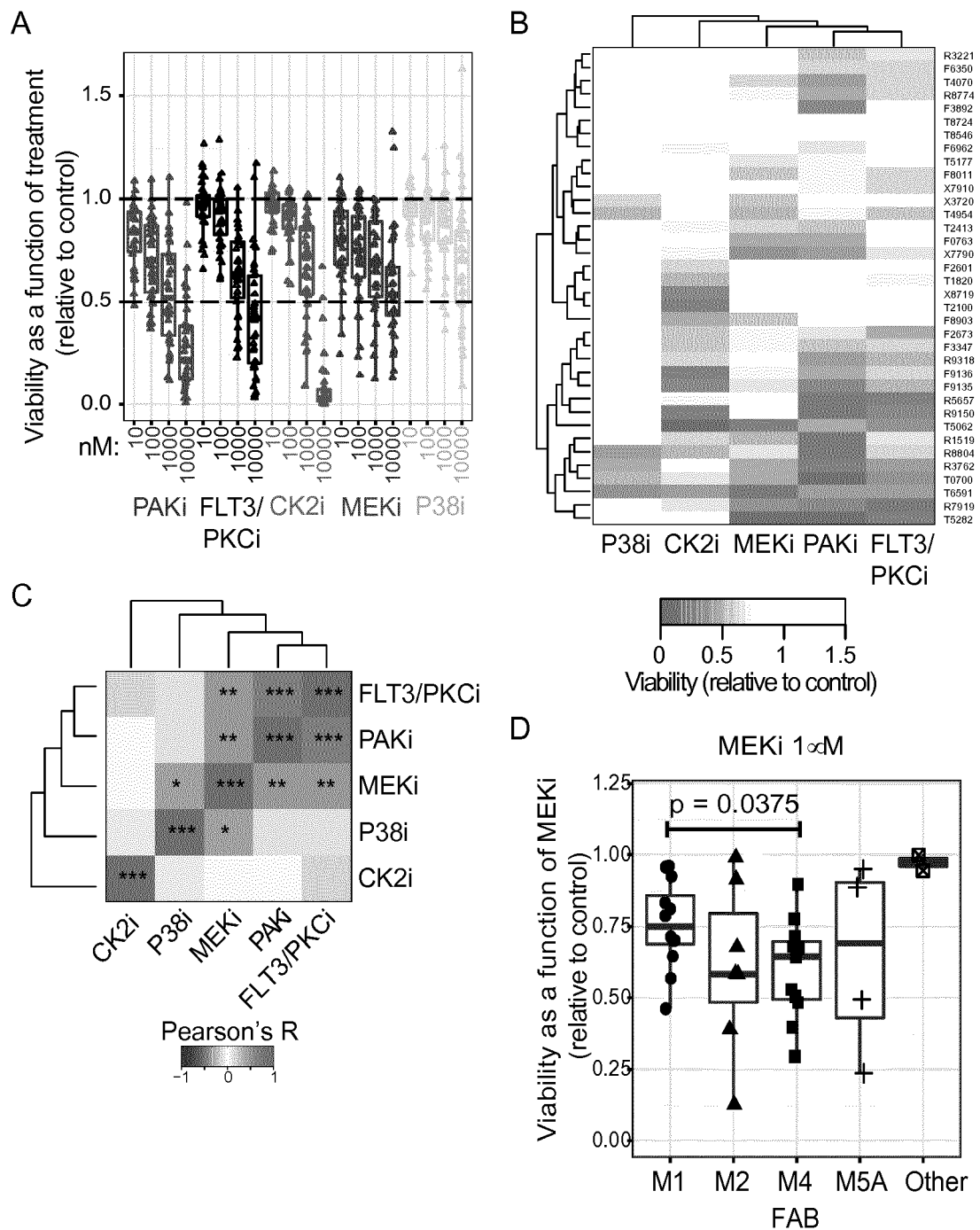

Zola et al., "CD molecules 2006—Human cell differentiation molecules", Journal of Immunological Methods, 2007, 319, pp. 1-5.
International Search Report and Written Opinion dated Aug. 13, 2018 for International Patent Application No. PCT/EP2018/066472.
Alcolea et al., "Phosphoproteomic Analysis of Leukemia Cells under Basal and Drug-treated Conditions Identifies Markers of Kinase Pathway Activation and Mechanisms of Resistance", Molecular & Cellular Proteomics, 2012, 11(8), pp. 453-466.

* cited by examiner

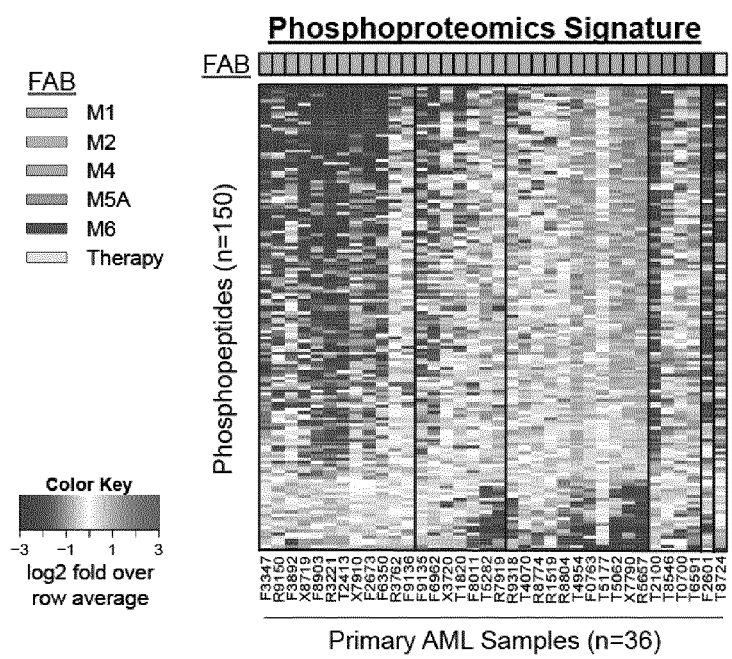
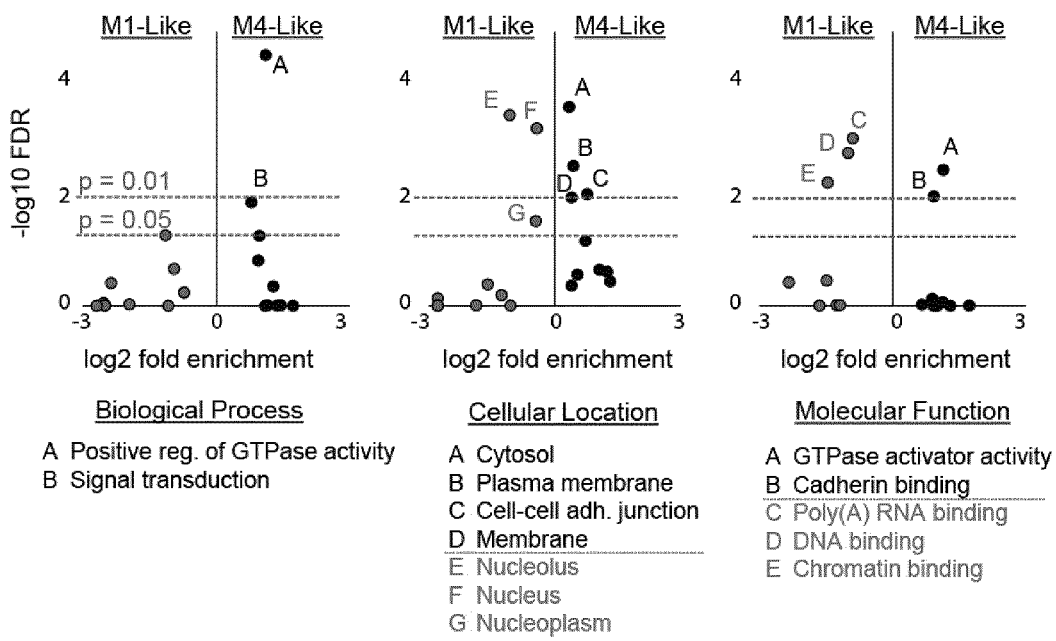
Figure 9

A

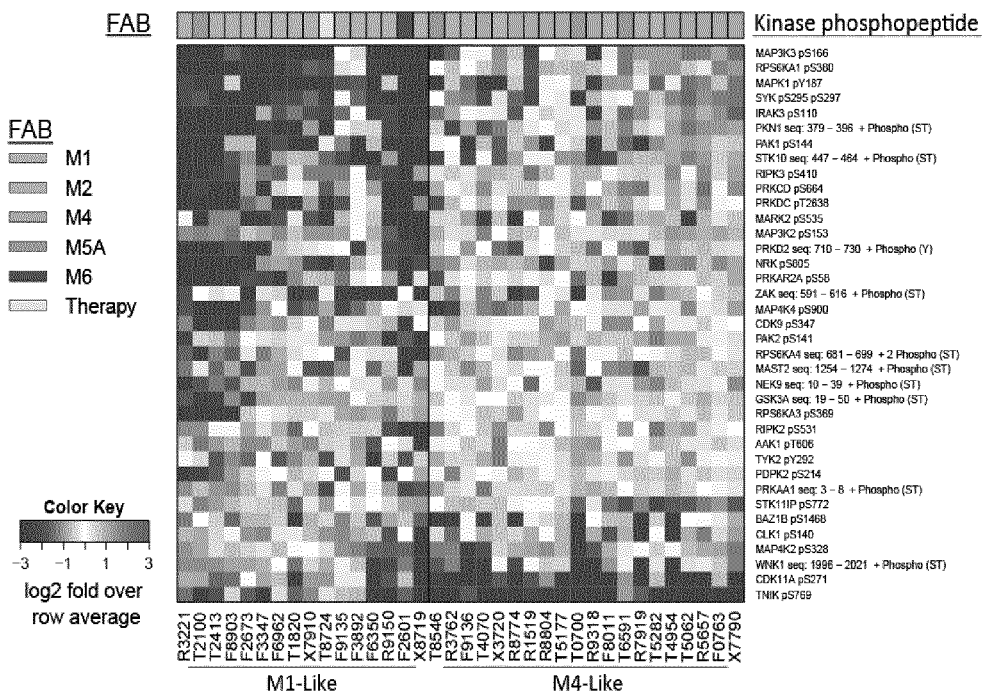

B

| Determinat | |
|---|---|
| CD19 | Co-receptor for CD21 |
| CD117 | Receptor Tyrosine Kinase /SCF |
| CD11b | Fibrinogen Receptor |
| CD64 | Fc Receptor |
| CD7 | |
| CD123 | Interleukin 3 Receptor |
| CD45 | Receptor Tyrosine Phosphatase C |
| CD33 | Sialic Acid Receptor |
| CD15 | Carbohydrate |
| CD34 | Cell-Cell Adhesion Factor |
| CD3 | TCR Co-receptor |
| CD44 | Hyaluronic Acid Receptor |
| CD38 | Synthesis of Cyclic ADP |
| HLA-DR | Antigen Presentation |
| CD184 | Chemokine Receptor /PSD-1 |
| CD14 | Co-activator of TLR4 |
| CD16 | Fc Receptor |

C

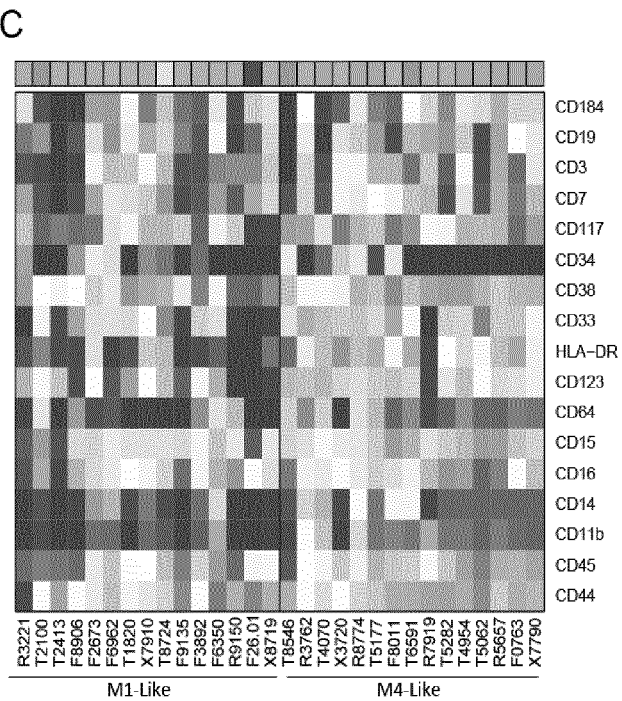

Figure 10

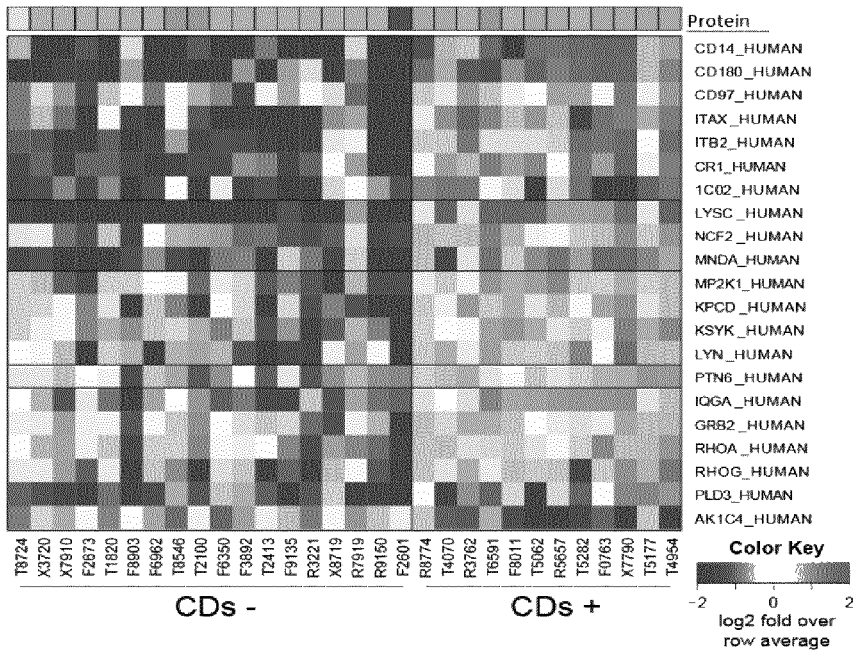
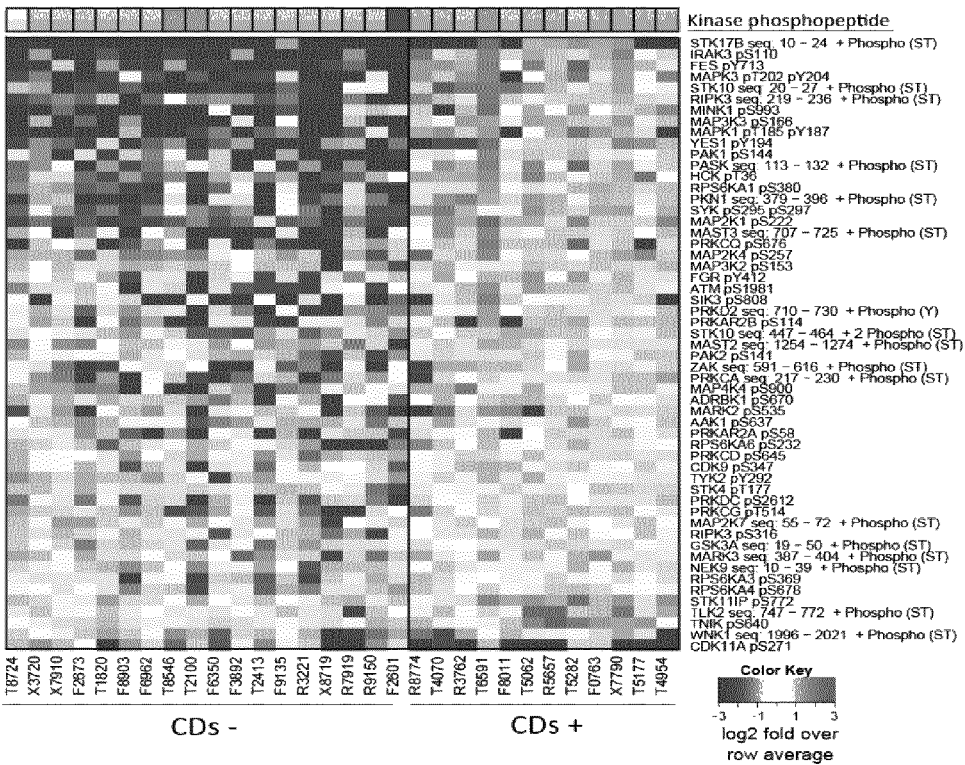
Figure 12

STRATIFICATION OF ACUTE MYELOID LEUKAEMIA PATIENTS FOR SENSITIVITY TO KINASE PATHWAY INHIBITOR THERAPY

The present invention relates to the treatment of acute myeloid leukaemia (AML) in patients. In particular, the invention concerns improved methods for identifying AML patients who may be effectively treated with kinase pathway inhibitors, and improved methods for predicting whether a kinase pathway inhibitor may be efficacious for treatment of AML in an individual patient. The invention also comprehends a method of screening a plurality of patients suffering from acute myeloid leukaemia, to determine whether the acute myeloid leukaemia of any one or more of the patients may be effectively treated with a kinase pathway inhibitor. The invention further provides methods for the treatment of such patients with kinase pathway inhibitors, and kinase pathway inhibitors for use in such methods.

Acute Myeloid Leukaemia—Disease Characteristics and Classification

Acute myeloid leukaemia (AML), also known as acute myelogenous leukaemia, acute myeloblastic leukaemia, acute granulocytic leukemia or acute nonlymphocytic leukemia, is an aggressive cancer of the blood and bone marrow. AML is characterised by excessive production of immature white blood cells, known as myeloblasts, by bone marrow. In healthy individuals, blasts normally develop into mature white blood cells. In AML, however, the blasts do not differentiate normally but remain at a premature arrested state of development.

In AML, the bone marrow may also make abnormal red blood cells and platelets. The number of these abnormal cells increases rapidly, and the abnormal cells begin to crowd out the normal white blood cells, red blood cells and platelets that the body needs. If left untreated, acute myeloid leukaemia is rapidly fatal.

Various classification systems have been devised for classifying AML into disease subtypes, with the aim of enabling more accurate prognosis of disease progression and identification of the optimal form of treatment. The earliest system was the French-American-British (FAB) classification, first devised in the 1970s by a group of French, American and British leukaemia experts. This system divides AML into subtypes according to the type of cell from which the leukaemia has developed, and the stage of maturity reached by the myeloblast cells at the point of arrest. Subtypes M0 to M5 originate from precursors of white blood cells and range from undifferentiated myeloblastic leukaemia (M0) to monocytic leukaemia (M5). Subtype M6 originates in very early forms of red blood cells (erythroid leukaemia), whilst subtype M7 AML starts in early forms of cells that form platelets (megakaryoblastic leukaemia).

Under the FAB system, AML is categorised by visual inspection of cytomorphological features under the microscope, and by identification of various chromosomal abnormalities. An updated version of the FAB categorisation was published in 1985—see Bennett et al, Proposed revised criteria for the classification of acute myeloid leukaemia, Ann Intern Med 1985; 103(4): 620-625.

Since the FAB system was first devised in the 1970s, the level of knowledge in the field has moved on considerably. Whilst the system has been updated to incorporate some of this knowledge, it was felt to be necessary to create a new classification system, taking into account additional factors now known to affect prognosis and to be determinative in optimising effective treatment.

The World Health Organization (WHO) classification system accordingly divides AML into several broad groups. These include:—
  AML with recurrent genetic abnormalities, meaning with specific chromosomal changes
  AML with multilineage dysplasia
  AML, related to previous therapy that is damaging to cells, including chemotherapy and radiotherapy, also called therapy-related myeloid neoplasm
  AML that is not otherwise categorized—including:—
    Undifferentiated AML (M0)
    AML with minimal maturation (M1)
    AML with maturation (M2)
    Acute myelomonocytic leukemia (M4)
    Acute monocytic leukemia (M5)
    Acute erythroid leukemia (M6)
    Acute megakaryoblastic leukemia (M7)
    Acute basophilic leukemia
    Acute panmyelosis with fibrosis
    Myeloid sarcoma (also known as granulocytic sarcoma or chloroma)

In addition to these two main classification systems, AML is further categorised and subtyped by reference to specific molecular markers which are found to correlate with certain phenotypes and outcomes. For example, patients with mutations in the NPM1 gene or CEBPA genes are known to have a better long term outcome, whilst patients with certain mutations in FLT3 have been found to have a worse prognosis—see Yohe et al, J Clin Med. 2015 Mar. 4(3): 460-478.

Current Treatment Regimes

Conventional treatment for AML includes chemotherapy and radiation therapy, as well as stem cell and bone marrow transplants. Most patients respond well at first to such therapy, but there is a high rate of relapse and patients typically become refractory to primary treatments. Overall, the 5 year survival rate for AML patients undergoing conventional therapy is around 26%.

Historically, with the exception of acute promyelocytic leukaemia, therapy for AML has not been targeted to the disease subtype. Rather, classification of AML according to the above-mentioned systems has principally served to inform clinical decisions as to the appropriate intensity of treatment. More recently, however, efforts have been made to identify targeted forms of treatment suitable for specific disease types and patient subgroups. Kinase pathway inhibitors have been the subject of particular interest as possible new personalised therapeutics in AML. Recently, the FLT3 inhibitor midostaurin has been approved by the FDA for treatment of adult patients having newly-diagnosed AML with certain activating mutations in the FLT3 gene. The pre-clinical efficacy of MEK inhibitors for treating AML with oncogenic NRAS mutations has also been investigated (Burgess at al, Blood 2014; 124(26): 3947-3955). However, kinase pathway inhibitors are not yet used routinely for treatment of AML, and the sensitivity of these screening protocols for reliably identifying patients who are susceptible to kinase pathway inhibitor treatment has not been fully tested.

There remains therefore a need for improved methods for targeted treatment of AML, and in particular for identifying patients who will be responsive to treatment with kinase pathway inhibitors, and those who will not be responsive to such treatment. Accurate and sensitive stratification is needed not only to ensure that patients who will respond to a particular treatment can be identified as such and treated appropriately, but also to ensure that patients who will not respond are not treated unnecessarily.

SUMMARY OF THE INVENTION

The present inventors have integrated proteomic, kinomic and genomic profiling to investigate the mechanisms that sensitise primary AML cells to kinase pathway inhibitors, thus permitting identification of biomarker panels which accurately identify sensitive cells. The inventors have found that leukaemia cells with an advanced differentiation status show higher sensitivity to kinase pathway inhibitors than less differentiated leukaemia cells. The differentiation status of leukaemia cells, which may be assessed according to protocols and criteria described herein, thus provides an effective biomarker for identification of leukaemia cells and patients that are sensitive to kinase pathway inhibitors. This enables new and effective stratification of patients for kinase inhibitor therapy. The inventors have further identified correlations between specific gene mutations and kinase pathway inhibitor sensitivity. These have the potential, inter alia, for providing effective companion diagnostic tests for use in conjunction with kinase pathway inhibitor therapy.

In a first aspect, therefore, the present invention provides a method for predicting the efficacy of a kinase pathway inhibitor for treatment of acute myeloid leukaemia in an individual patient, which kinase pathway inhibitor inhibits a kinase signalling pathway that is involved in cell proliferation or cell survival, comprising the steps of:

(a) determining the differentiation status of the patient's leukaemia; and (b) if the differentiation status of the leukaemia is advanced, predicting that the acute myeloid leukaemia in the patient may be effectively treated with said kinase pathway inhibitor.

In a second aspect, the present invention provides a method of treating acute myeloid leukaemia in an individual patient, comprising the steps of:

(a) determining the differentiation status of the patient's leukaemia; and (b) if the differentiation status of the leukaemia is advanced, treating the patient with a kinase pathway inhibitor which inhibits a kinase signalling pathway that is involved in cell proliferation or cell survival.

In a third aspect, the present invention provides a method of screening a plurality of patients with acute myeloid leukaemia to determine whether the acute myeloid leukaemia of any one or more of said plurality of patients may be effectively treated with a kinase pathway inhibitor, which kinase pathway inhibitor inhibits a kinase signalling pathway that is involved in cell proliferation or cell survival, comprising the steps of:

(a) for each patient, determining the differentiation status of the patient's leukaemia; and (b) identifying any one or more patients having leukaemia with an advanced differentiation status as having leukaemia suitable for effective treatment with the kinase pathway inhibitor.

In a fourth aspect, the present invention provides a kinase pathway inhibitor, which kinase pathway inhibitor inhibits a kinase pathway that is involved in cell proliferation or cell survival, for use in a method of treating acute myeloid leukaemia in an individual patient, wherein the treatment comprises:

(a) determining the differentiation status of the patient's leukaemia; and (b) if the differentiation status of the leukaemia cells is advanced, treating the patient with said kinase pathway inhibitor.

The present invention further provides for computer implementation of the method of screening according to the third aspect of the invention and the method of predicting efficacy of kinase pathway inhibitor therapy according to the first aspect of the invention. The present invention also provides software for performing either or both of these computer-implemented methods.

These aspects of the present invention each comprise a step (a) of determining the differentiation status of a patient's leukaemia. As described above, AML involves proliferation of aberrant, partially-differentiated myeloblasts. The term "differentiation status of a patient's leukaemia" thus refers to the differentiation status of the patient's leukaemia cells. Suitably, therefore, step (a) may involve determining the differentiation status of leukaemia cells which have previously been obtained from the patient. Alternatively, step (a) may further involve obtaining leukaemia cells from the patient, prior to determining the differentiation status of said leukaemia cells. Said leukaemia cells may, for example, be obtained from peripheral blood samples or from bone marrow samples. This invention is applicable to all AML patients, including newly-diagnosed (untreated) AML patients, AML patients who have undergone or are undergoing other forms of treatment, and relapsed AML patients.

Suitably, the differentiation status of the leukaemia cells may be determined by analysing data relating to the leukaemia cells as described hereinbelow. In some embodiments, said data has previously been gathered and recorded and step (a) comprises obtaining or receiving said data for analysis. In other embodiments, step (a) further comprises gathering and recording said data for analysis, as described hereinbelow. In some embodiments, said step of determining the differentiation status of the patient's leukaemia may consist of determining whether or not the patient's leukaemia is advanced (a binary (yes/no) determination).

The differentiation status of a patient's leukaemia may be determined by analysing data relating to morphological and/or cytochemical features of the leukaemia cells, and/or by analysing data relating to expression, activation and/or phosphorylation in the leukaemia cells of one or more differentiation markers such as cell surface differentiation markers and/or functional differentiation markers including kinase pathway activity markers, and/or by reference to data recording the classification of the leukaemia cells under the French-American-British (FAB) classification as described in Bennett et al, *Proposed revised criteria for the classification of acute myeloid leukaemia*, Ann Intern Med 1985; 103(4): 620-625. The data may include any type of information concerning the cells, including without limit information regarding the appearance, properties, characteristics, genotype, phenotype, activity, classification and function of the cells, and including without limit images of the cells, written descriptions of the cells, and measurements of all types obtained from the cells.

Said data relating to morphological features of the leukaemia cells may include data recording the visual appearance of the cells under a light microscope, optionally using a stain such as Romanowsky's stain. Said data may, for example, include visual images of the cells and/or written descriptions of the cells. Step (a) may comprise analysing the data to determine if the cells satisfy the FAB criteria for identification of M4 cells as defined in Bennett et al, op. cit. In particular, an advanced differentiation status may be determined if the data indicates that at least 20% of the leukaemia cells have an appearance characteristic of granulocytic-monocytic cells, and/or if the data indicates that amongst the leukaemia cells, myeloblasts, monoblasts and promonocytes constitute 20% or more of nonerythroid cells, and myeloblasts and granulocytes constitute 80% or less of nonerythroid cells. An advanced differentiation status may for example be determined if the data indicates that at least 20% of the cells have lightly granulated, greyish cytoplasm and folded nuclei, characteristic of granulocytic-monocytic cells (M4 FAB). An advanced differentiation status may be determined if in a sample obtained from bone marrow, the blast cells (myeloblasts, promyelocytes, myelocytes and later granulocytes) constitute more than 30% but less than 80% of the non-erythroid cells; and, preferably but not essentially, if in a sample obtained from peripheral blood, the monocyte count (monoblasts, promonocytes and monocytes) is $5 \times 10^9$/L or more. See Bennett, op. cit, at page 622.

In some embodiments, said data relating to morphological features of the leukaemia cells has previously been recorded and step (a) comprises obtaining said data for analysis. In other embodiments, step (a) further comprises gathering and recording said data relating to morphological features of the leukaemia cells for analysis. Methods for collecting and recording said data relating to morphological features of the cells are conventional and well-known in the art, being described in Bennett et al (op cit) and elsewhere.

Said data relating to cytochemical features of the leukaemia cells may include data recording the response of the cells to reagents such as sudan black B and/or peroxidase and/or specific or non-specific esterases. Said data may, for example, include visual images of the cells, written descriptions of the cells, flow cytometry data and other types of cytochemical data. Step (a) may comprise analysing the data to determine if the cells satisfy the FAB criteria for identification of M4 cells as defined in Bennett et al, op. cit. In particular, an advanced differentiation status may be determined if the data indicates that at least 20% of the cells are responsive to sudan black B and/or peroxidase and/or specific or non-specific esterase (M4 FAB).

In some embodiments, said data relating to cytochemical features of the leukaemia cells has previously been recorded and step (a) comprises obtaining said data for analysis. In other embodiments, step (a) further comprises gathering and recording said data relating to cytochemical features of the leukaemia cells for analysis. Methods for collecting and recording data relating to cytochemical features of cells are conventional and well-known in the art, being described in Bennett et al (op cit) and elsewhere.

Said data relating to expression, activation and/or phosphorylation in the leukaemia cells of one or more differentiation markers such as cell surface differentiation markers and/or functional differentiation markers may include data recording the presence or absence or the level of expression on the surface of the leukaemia cells of one or more cell surface differentiation markers, such as signalling molecules, which cell surface differentiation markers are typically expressed or over-expressed in healthy myelomonocytic cells and which cell surface differentiation markers are not typically expressed or over-expressed in undifferentiated myeloblasts; wherein the presence of said one or more cell surface differentiation markers on the leukaemia cells, or the expression of said one or more cell surface differentiation markers at a high level on the leukaemia cells indicates an advanced differentiation status. Said data may, for example, include a written description of the cells, or any type of data obtained from an assay measuring cell surface protein expression, such as by mass cytometry or any other technique or assay that is known in the art. In some embodiments, said data has previously been recorded and step (a) comprises obtaining said data for analysis. In other embodiments, step (a) further comprises collecting and recording said data for analysis, according to standard conventional methods and protocols known in the art, for example by mass cytometry.

Said cell surface differentiation markers may comprise a panel of cell surface marker proteins including one or more of CD3, CD7, CD11b, CD11c (integrin α-X, ITAX), CD14, CD15, CD16, CD18 (integrin β, ITB2), CD19, CD33, CD34, CD35 (CR1), CD38, CD44, CD45, CD64, CD97, CD117, CD123, CD180, CD184, HLA-C(1CO2), APOBR, the platelet membrane receptor Gi24 (VSIR) and HLA-DR; and/or any cell surface proteins which are expressed in conjunction with said one or more cell surface marker proteins. CD markers, also known as cluster of differentiation markers, are a well-defined subset of cellular surface receptors (epitopes) that are specific as to cell type and stage of differentiation, and which are recognized by antibodies. The cell surface marker proteins listed above are all known in the art and are well characterised—see, for example, Zola et al H, (2007). "CD molecules 2006—human cell differentiation molecules.". J Immunol Methods. 319 (1-2): 1-5. These cell surface marker proteins have been found to be typically expressed typically at a high level on the surface of leukaemia cells with an advanced differentiation status which are sensitive to kinase pathway inhibitors, but are not typically expressed in undifferentiated myeloblasts. Step (a) may therefore involve analysing the data to determine if the panel of cell surface marker proteins is expressed or is expressed at a high level by said leukaemia cells, where an advanced differentiation status is determined if the panel of cell surface marker proteins is expressed or is expressed at a high level. Preferably, the panel of cell surface marker proteins includes any two, or three, or four, or five, or six, or seven, or eight, or nine, or ten, or eleven, or twelve, or thirteen, or fourteen, or fifteen, or sixteen, or seventeen, or eighteen, or all of CD11b, CD11c (integrin α-X, ITAX), CD14, CD15, CD16, CD18 (integrin β, ITB2), CD33, CD35 (CR1), CD38, CD44, CD45, CD64, CD97, CD123, CD180, HLA-C(1CO2), APOBR, the platelet membrane receptor Gi24 (VSIR) and HLA-DR.

References to expression of one or more cell surface proteins, such as cell surface marker proteins, at a "high level", as used here and elsewhere in the specification, denote a level of expression which is higher than the average level of expression of the relevant cell surface proteins. References to a "low level" of expression similarly denote a level of expression which is the same as or less than the average level of expression of the cell surface proteins. The average level of expression of the cell surface proteins is a standardised value which may be determined by reference to an average calculated across a plurality of samples, or by reference to the level of expression of the cell surface proteins in undifferentiated myeloblasts or other healthy cell types, which may be established either by laboratory analysis according to methods well known in the art (including LC-MS/MS), or by reference to information available in the art. Thus, for example, the average level of expression of the cell surface proteins may be determined by establishing the range of expression levels of the cell surface proteins in cell samples obtained from a large number of AML patients, and calculating the mean level of expression across the samples. A "high level" of expression of the cell surface proteins is a level of expression which is higher than the calculated mean.

Optionally, the panel of cell surface marker proteins may further include one or more of CD19, CD117, CD7, CD34, CD3, and CD184. The panel of cell surface marker proteins may advantageously include CD45, and/or CD11b, and/or CD44, and/or CD14, and/or CD16, and/or CD64 and/or CD15. In particular, the panel of cell surface marker proteins may include any one of CD45, CD11b, CD44, CD14, CD16, CD64 and CD15, or any two, three, four, five or six of CD45, CD11b, CD44, CD14, CD16, CD64 and CD15. Suitably, the panel of cell surface marker proteins may consist of CD45, CD11b, CD44, CD14, CD16, CD64 and CD15. In some preferred embodiments, the panel of cell surface markers consists of any one, two, three, four, five, six, seven, eight, nine, ten or all of CD11b, CD14, CD15, CD16, CD33, CD38, CD44, CD45, CD64, CD123 and HLA-DR. In other preferred embodiments, the panel of cell surface marker proteins consists of any one, two, three, four, five, six, seven, eight, nine, ten, eleven, twelve, thirteen, fourteen, fifteen, sixteen or all of CD3, CD7, CD11b, CD14, CD15, CD16, CD19, CD33, CD34, CD38, CD44, CD45, CD64, CD117, CD123, CD184, and HLA-DR.

Said data relating to expression, activation and/or phosphorylation in the leukaemia cells of one or more differentiation markers such as cell surface differentiation markers and/or functional differentiation markers may, additionally or alternatively, comprise data recording the expression and/or activation and/or phosphorylation of one or more functional differentiation markers, which functional differentiation markers are typically expressed, over-expressed, activated and/or phosphorylated in healthy monomyelocytic cells, and which functional differentiation markers are not typically expressed, over-expressed, activated and/or phosphorylated in undifferentiated myeloblasts; wherein the expression, activation and/or phosphorylation of said one or more functional differentiation markers indicates an advanced differentiation status. Said data may, for example, include a written description of the cells, or any type of data obtained from an assay measuring expression, activation or phosphorylation of cellular proteins, according to any technique known in the art, such as LC-MS/MS analysis or immunochemical techniques including Western blotting, ELISA, and reversed phase protein assays. In some embodiments, said data has previously been recorded and step (a) comprises obtaining said data for analysis. In other embodiments, step (a) further comprises collecting and recording said data for analysis, according to standard conventional methods known in the art, such as by LC-MS/MS.

Said one or more functional differentiation markers may comprise a panel of protein markers including one or more enzymes, integrins, kinases, phosphatases, signal transduction regulators, cytoplasmic proteins and phosphoproteins, membrane proteins and phosphoproteins, including cytoplasmic and membrane phosphoproteins that are involved in GTPase or other forms of cell signalling, which protein markers are typically expressed, over-expressed and/or activated in healthy monomyelocytic cells, and are not typically expressed, over-expressed and/or activated in undifferentiated myeloblasts.

The panel of protein markers may include any one, two, three, four, five, six, seven, eight, nine, ten or more of lysozyme C (LYZ), neutrophil cytosol factor 2 (NCF2), myeloid cell nuclear differentiation antigen (MNDA), AK1C4, ERG, Nesprin 3, Voltage-gated hydrogen channel 1, Fructose-1,6-bisphosphatase 1, Monocyte differentiation antigen CD14, Thymidine phosphorylase, CD180 antigen, Putative annexin A2-like protein, Retinoid-inducible serine carboxypeptidase, Annexin A2, Golgi-associated plant pathogenesis-related protein 1, Integrin beta-2, BTB/POZ domain-containing protein KCTD12, Cytoskeleton-associated protein 4, Integrin alpha-X, Complement receptor type 1, Annexin A5, Uncharacterized protein F1145252, Galectin-3, Adenylate kinase isoenzyme 1, Protein S100-A10, Thiamine-triphosphatase, Deoxynucleoside triphosphate triphosphohydrolase SAMHD1, Mitochondrial amidoxime-reducing component 1, Coronin-1B, Arf-GAP with Rho-GAP domain, ANK repeat and PH domain-containing protein 1, Granulins, Ribonuclease inhibitor, Long-chain-fatty-acid—CoA ligase 1, Protein S100-A11, Pro-cathepsin H, Cathepsin S, Galectin-1, Transport and Golgi organization protein 2 homolog, Arf-GAP domain and FG repeat-containing protein 1, Long-chain-fatty-acid—CoA ligase 3, Ras GTPase-activating-like protein IQGAP1, Allograft inflammatory factor 1, Transcription intermediary factor 1-beta, Beta-arrestin-2, Dihydropyrimidine dehydrogenase [NADP(+)], Alpha-N-acetylgalactosaminidase, Cathepsin B, Aminopeptidase B, Lysosomal protective protein, Phosphoglycerate mutase 1, Polypeptide N-acetylgalactosaminyltransferase 2, Cytokine receptor-like factor 3, Calpastatin, EF-hand domain-containing protein D2, Dual specificity mitogen-activated protein kinase kinase 1, Major vault protein, Alpha-galactosidase A, Tyrosine-protein kinase SYK, Sister chromatid cohesion protein PDS5 homolog B, Calpain-2 catalytic subunit, FK506-binding protein 15, Protein disulfide-isomerase, Tensin-3, Apolipoprotein B receptor, Transforming protein RhoA, Plastin-2, Actin-related protein 2/3 complex subunit 2, CD97 antigen, Cathepsin Z, Neuroblast differentiation-associated protein AHNAK, Unconventional myosin-If, Pyruvate kinase PKM, Protein THEMIS2, Plastin-3, Tyrosine-protein phosphatase non-receptor type 6, Ezrin, Leucine-rich repeat-containing protein 59, Guanine nucleotide-binding protein G(I)/G(S)/G(T) subunit beta-2, Coronin-1A, Radixin, Transketolase, Growth factor receptor-bound protein 2, V-type proton ATPase subunit B (kidney isoform), Coatomer subunit epsilon, Alpha-soluble NSF attachment protein, Rho GDP-dissociation inhibitor 2, and/or Guanine nucleotide-binding protein subunit beta-4, and/or any proteins which are selectively expressed and/or activated therewith. These protein markers have been found to be typically expressed and/or activated in leukaemia cells with an advanced differentiation status which are sensitive to kinase pathway inhibitors, but are not typically expressed and/or activated in undifferentiated myeloblasts. Step (a) may therefore comprise analysing the data to determine if the panel of protein markers is expressed and/or activated in said leukaemia cells, where an advanced differentiation status is determined if the panel of protein markers is expressed and/or activated in the cells.

Advantageously, the panel of protein markers may include any one, two, three, four or five of lysozyme C (LYZ), neutrophil cytosol factor 2 (NCF2), myeloid cell nuclear differentiation antigen (MNDA), AK1C4, and ERG; and step (a) may comprise analysing the data to determine if this panel of protein markers is expressed in the leukaemia cells, where an advanced differentiation status is determined if the panel of protein markers is expressed in the cells.

Said one or more functional differentiation markers may additionally or alternatively comprise a panel of kinase pathway activity markers including one or more kinases, phosphatases, phospholipoases, integrins, signal transduction regulators, G proteins, transmembrane receptors, phosphopeptides and/or other kinase signalling molecules that are typically expressed and/or activated and/or phosphorylated in a kinase signalling pathway in healthy monomyelocytic cells but are not typically expressed and/or activated and/or phosphorylated in undifferentiated myeloblasts. Advantageously, the kinase signalling pathway may be a pathway that is inhibited by the kinase pathway inhibitor.

Thus, for example, where the kinase pathway inhibitor is a RAS-RAF-MEK-ERK pathway inhibitor such as trametinib, the panel of kinase pathway activity markers may comprise markers of the RAS-RAF-MEK-ERK signalling pathway.

In particular, the panel of kinase pathway activity markers may include one or more kinases, phosphatases, phospholipoases, integrins, signal transduction regulators, G proteins, transmembrane receptors and/or other kinase signalling molecules that are expressed and/or activated in a kinase signalling pathway that is involved in cell proliferation or cell survival. In some embodiments, one or more of said kinases, phosphatases, phospholipoases, integrins, signal transduction regulators, G proteins, transmembrane receptors and/or other kinase signalling molecules may be expressed and/or activated in a kinase signalling pathway that is inhibited by said kinase pathway inhibitor. In some embodiments, one or more of said kinases, phosphatases, phospholipoases, integrins, signal transduction regulators, G proteins, transmembrane receptors and/or other kinase signalling molecules may be inhibited by said kinase pathway inhibitor.

The panel of kinase pathway activity markers may include any one, two, three, four, five, six, seven, eight, nine, ten or more of FES, PKC and protein kinase C isoforms including PKCδ (KPCD), PRKCA, PRKCB, and PRKCD, PKA, PAK including PAK1 and PAK2, STK10, GSK3A, RSK2, RAS, RAF, MEK including MEK1 (MAP2K1), ERK including MAPK3 (ERK1) and MAPK1 (ERK2), PI3K, AKT including AKT1, MTOR, S6 kinase, STAT5, CAMKK, SYK (KSYK), LYN, P38A, CDK1, CK2A1, PKACA, IRAK4, PKCB iso2, Cot, PKCD, PKCA, PKCB, PKCG, PKCH, BRAF, MEK2, PDK1, CDK2, PTN6, D3 (PLD3), IQGAP1, GRB2, RHOA, RHOG and S10AB, and any kinases, phosphatases, phospholipoases, integrins, signal transduction regulators, G proteins, transmembrane receptors and/or other kinase signalling molecules that are selectively expressed or activated therewith. These kinase pathway activity markers have been found to be typically expressed and/or activated and/or phosphorylated in leukaemia cells with an advanced differentiation status which are sensitive to kinase pathway inhibitors, but are not typically expressed and/or activated and/or phosphorylated in undifferentiated myeloblasts. Step (a) may therefore comprise analysing the data to determine if the panel of kinase pathway activity markers is expressed and/or activated and/or phosphorylated in said leukaemia cells, where an advanced differentiation status is determined if the panel of kinase pathway activity markers is expressed and/or activated and/or phosphorylated in the cells.

Advantageously, the panel of kinase pathway activity markers may include any one, two, three, or four of PKC, ERK, PAK1 and P38α and step (a) may include analysing the data to determine if this panel of kinase pathway activity markers is expressed and activated in the leukaemia cells, where an advanced differentiation status is determined if the panel of kinase pathway activity markers is expressed and activated in the cells.

Suitably, the panel of kinase pathway activity markers may include any one, two, three, four or five of PKCD, PKCA, PKACA, IRAK4 and CK2A1, and step (a) may include analysing the data to determine if this panel of kinase pathway activity markers is expressed and activated in the leukaemia cells, where an advanced differentiation status is determined if the panel of kinase pathway activity markers is expressed and activated in the cells. Alternatively, the panel of kinase pathway activity markers may include any one, two, three, four, five or six of MAPK1, MAPK2, AKT, AKT1S1, MAP2K1 and MAP2K2, and step (a) may include analysing the data to determine if this panel of kinase pathway activity markers is expressed and activated in the leukaemia cells, where an advanced differentiation status is determined if the panel of kinase pathway activity markers is expressed and activated in the cells.

The panel of kinase pathway activity markers may additionally or alternatively comprise a panel of one or more phosphorylation sites which are typically phosphorylated or are typically phosphorylated at a high level in a kinase signalling pathway in healthy monomyelocytic cells but are not typically phosphorylated or not typically phosphorylated at a high level in undifferentiated myeloblasts Step (a) may comprise analysing the data to determine if the panel of phosphorylation sites is phosphorylated at a high level in said leukaemia cells, where an advanced differentiation status is determined if the panel of phosphorylation sites is phosphorylated at a high level in the leukaemia cells.

References to phosphorylation at a "high level", as used here and elsewhere in the specification, denote a level of phosphorylation which is higher than the average phosphorylation of the reference protein or at the reference phosphorylation site. References to a "low level" of phosphorylation similarly denote a level of phosphorylation which is the same as or less than the average phosphorylation of the reference protein or at the reference phosphorylation site. The average phosphorylation of the reference protein or the reference phosphorylation site is a standardised value which may be determined by reference to an average calculated across a plurality of samples, or by reference to the phosphorylation state of the reference protein or the reference phosphorylation site in undifferentiated myeloblasts or other healthy cell types, which may be established either by laboratory analysis according to methods well known in the art (including LC-MS/MS), or by reference to information available in the art. Thus, for example, the average level of phosphorylation at a particular phosphorylation site may be determined by establishing the range of phosphorylation at that site in cell samples obtained from a large number of AML patients, and calculating the mean phosphorylation across the samples. A "high level" of phosphorylation at that site is a level of phosphorylation which is higher than the calculated mean.

In particular, the panel of phosphorylation sites may include one or more phosphorylation sites that are phosphorylated at a high level in a kinase signalling pathway which is involved in cell proliferation or cell survival. In some embodiments, one or more of said phosphorylation sites may be phosphorylated at a high level in a kinase signalling pathway which is inhibited by said kinase pathway inhibitor.

The panel of phosphorylation sites may include any one, two, three, four, five, six, seven, eight, nine, ten or more than ten of the phosphorylation sites set out in Table 1 below.

TABLE 1

| Phosphoprotein | Phosphorylation site |
|---|---|
| 1-phosphatidylinositol 3-phosphate 5-kinase PIKFYVE | PIKFYVE pS307 |

TABLE 1-continued

| Phosphoprotein | Phosphorylation site |
|---|---|
| 26S proteasome non-ATPase regulatory subunit 4 PSMD4 | PSMD4 pS256 |
| 28 kDa heat- and acid-stable phosphoprotein PDAP1 | PDAP1 pS178 |
| 2-oxoisovalerate dehydrogenase subunit alpha, mitochondrial BCKDHA | BCKDHA pS347 |
| 40S ribosomal protein S14 RPS14 | RPS14 seq: 129-141 + Phospho (ST) |
| 40S ribosomal protein S2 RPS2 | RPS2 seq: 276-284 + Phospho (ST) |
| 40S ribosomal protein S6 RPS6 | RPS6 seq: 233-243 + 2 Phospho (ST) |
| 5'-3' exoribonuclease 2 XRN2 | XRN2 pS448 |
| 5'-AMP-activated protein kinase catalytic subunit alpha-1 PRKAA1 | PRKAA1 seq: 3-8 + Phospho (ST) |
| 60S acidic ribosomal protein P1 RPLP1 | RPLP1 pS104 |
| 60S ribosomal protein L23a RPL23A | RPL23A seq: 40-47 + Phospho (ST) |
| 7SK snRNA methylphosphate capping enzyme MEPCE | MEPCE pS254 |
| 7SK snRNA methylphosphate capping enzyme MEPCE | MEPCE pS60 |
| Absent in melanoma 1 prote | AIM1 seq: 479-495 + Phospho (ST) |
| Acetyl-coenzyme A synthetase, cytoplasmic ACSS2 | ACSS2 pS267 |
| Acetyl-coenzyme A synthetase, cytoplasmic ACSS2 | ACSS2 pS30 |
| Acetyl-coenzyme A synthetase, cytoplasmic ACSS2 | ACSS2 seq: 256-272 + Phospho (ST) |
| Actin, alpha skeletal muscle ACTA1 | ACTA1 pS54 |
| Actin-related protein 2/3 complex subunit 1B ARPC1B | ARPC1B seq: 309-326 + Phospho (ST) |
| Activating transcription factor 7-interacting protein 1 ATF7IP | ATF7IP pS113 |
| Adaptin ear-binding coat-associated protein 2 NECAP2 | NECAP2 seq: 177-195 + Phospho (ST) |
| ADP-ribosylation factor GTPase-activating protein 2 ARFGAP2 | ARFGAP2 seq: 314-336 + Phospho (ST) |
| Aflatoxin B1 aldehyde reductase member 2 AKR7A2 | AKR7A2 pS255 |
| A-kinase anchor protein 11 AKAP11 | AKAP11 pS1611 |
| A-kinase anchor protein 13 AKAP13 | AKAP13 pS1507 |
| A-kinase anchor protein 13 AKAP13 | AKAP13 pS1559 |
| A-kinase anchor protein 13 AKAP13 | AKAP13 pS1559 |
| A-kinase anchor protein 13 AKAP13 | AKAP13 pS1876 |
| A-kinase anchor protein 13 AKAP13 | AKAP13 pS2709 |
| A-kinase anchor protein 13 AKAP13 | AKAP13 pS983 |
| A-kinase anchor protein 13 AKAP13 | AKAP13 seq: 1600-1631 + Phospho (ST) |
| A-kinase anchor protein 13 AKAP13 | AKAP13 seq: 1904-1924 + Phospho (ST) |
| A-kinase anchor protein 13 AKAP13 | AKAP13 seq: 2561-2573 + Phospho (ST) |
| A-kinase anchor protein 13 AKAP13 | AKAP13 seq: 330-367 + Phospho (ST) |
| A-kinase anchor protein 13 AKAP13 | AKAP13 seq: 647-681 + Phospho (ST) |
| A-kinase anchor protein 13 AKAP13 | AKAP13 seq: 939-966 + Phospho (ST) |
| Allograft inflammatory factor 1 AIF1 | AIF1 seq: 37-53 + Phospho (ST) |
| AMP deaminase 2 AMPD2 | AMPD2 pS100 |
| Amyloid beta A4 precursor protein-binding family A member 3 APBA3 | APBA3 pS11 |
| AP2-associated protein kinase 1 AAK1 | AAK1 pT606 |
| AP2-associated protein kinase 1 AAK1 | AAK1 pT620 |
| AP2-associated protein kinase 1 AAK1 | AAK1 seq: 652-667 + Phospho (ST) |
| AP2-associated protein kinase 1 AAK1 | AAK1 seq: 9-37 + Phospho (ST) |
| Apolipoprotein B recept | APOBR seq: 552-571 + Phospho (ST) |
| Apolipoprotein B recept | APOBR seq: 968-990 + Phospho (ST) |
| Apolipoprotein B receptor APOBR | APOBR seq: 1004-1009 + 2 Phospho (ST) |

TABLE 1-continued

| Phosphoprotein | Phosphorylation site |
|---|---|
| Apolipoprotein O-like APOOL | APOOL seq: 201-212 + Phospho (ST) |
| Arf-GAP domain and FG repeat-containing protein 1 AGFG1 | AGFG1 seq: 291-313 + Phospho (ST) |
| Arf-GAP with coiled-coil, ANK repeat and PH domain-containing protein 2 ACAP2 | ACAP2 seq: 538-543 + Phospho (ST) |
| Arf-GAP with Rho-GAP domain, ANK repeat and PH domain-containing protein | ARAP1 pS1435 |
| Arf-GAP with Rho-GAP domain, ANK repeat and PH domain-containing protein 1 ARAP1 | ARAP1 pS1419 |
| Arf-GAP with Rho-GAP domain, ANK repeat and PH domain-containing protein 1 ARAP1 | ARAP1 pS1435 |
| Arf-GAP with Rho-GAP domain, ANK repeat and PH domain-containing protein 1 ARAP1 | ARAP1 pS229 |
| Arf-GAP with Rho-GAP domain, ANK repeat and PH domain-containing protein 1 ARAP1 | ARAP1 seq: 222-244 + Phospho (ST) |
| Arf-GAP with SH3 domain, ANK repeat and PH domain-containing protein 1 ASAP1 | ASAP1 pS839 pS843 |
| Arf-GAP with SH3 domain, ANK repeat and PH domain-containing protein 1 ASAP1 | ASAP1 seq: 733-750 + Phospho (ST) |
| Arf-GAP with SH3 domain, ANK repeat and PH domain-containing protein 1 ASAP1 | ASAP1 seq: 837-852 + 2 Phospho (ST) |
| Arginine/serine-rich protein PNISR PNISR | PNISR pS211 |
| Astrocytic phosphoprotein PEA-15 PEA15 | PEA15 pS116 |
| Ataxin-1 ATXN1 | ATXN1 seq: 230-259 + Phospho (ST) |
| Ataxin-2-like protein ATXN2L | ATXN2L pS111 |
| Atherin SAMD1 | SAMD1 pS161 |
| ATPase WRNIP1 WRNIP1 | WRNIP1 pS153 |
| ATP-binding cassette sub-family F member 1 ABCF1 | ABCF1 pS140 |
| ATP-citrate synthase ACLY | ACLY pS455 |
| ATP-dependent 6-phosphofructokinase, liver type PFKL | PFKL pS775 |
| ATP-dependent RNA helicase DDX3Y DDX3Y | DDX3Y pS592 |
| ATP-dependent RNA helicase DHX | DHX29 seq: 66-83 + Phospho (ST) |
| Band 4.1-like protein 3 EPB41L3 | EPB41L3 pS460 |
| Band 4.1-like protein 3 EPB41L3 | EPB41L3 pS962 |
| B-cell lymphoma/leukemia 11A BCL11A | BCL11A pS328 |
| B-cell lymphoma/leukemia 11A BCL11A | BCL11A pS718 |
| B-cell lymphoma/leukemia 11A BCL11A | BCL11A pS86 |
| B-cell lymphoma/leukemia 11A BCL11A | BCL11A seq: 321-341 + 2 Phospho (ST) |
| BCL2/adenovirus E1B 19 kDa protein-interacting protein 2 BNIP2 | BNIP2 pS114 |
| Beta-1-syntrophin SNTB1 | SNTB1 seq: 222-239 + Phospho (ST) |
| Beta-adrenergic receptor kinase 1 ADRBK1 | ADRBK1 pS670 |
| Brain-specific angiogenesis inhibitor 1-associated protein 2 BAIAP2 | BAIAP2 pS366 |
| Breakpoint cluster region protein BCR | BCR pS122 |
| Breakpoint cluster region protein BCR | BCR pS459 |
| Bridging integrator 2 BIN2 | BIN2 pS458 |
| Bridging integrator 2 BIN2 | BIN2 seq: 355-390 + 2 Phospho (ST) |
| Bridging integrator 2 BIN2 | BIN2 seq: 450-477 + 2 Phospho (ST) |
| Bridging integrator 2 BIN2 | BIN2 seq: 461-477 + Phospho (ST) |
| Bridging integrator 2 BIN2 | BIN2 seq: 461-482 + 2 Phospho (ST) |
| Bromodomain and PHD finger-containing protein 3 BRPF3 | BRPF3 pS645 |
| BTB/POZ domain-containing protein KCTD | KCTD12 seq: 185-206 + 2 Phospho (ST) |
| BTB/POZ domain-containing protein KCTD | KCTD12 seq: 247-265 + Phospho (ST) |
| BTB/POZ domain-containing protein KCTD12 KCTD12 | KCTD12 pS151 |
| BTB/POZ domain-containing protein KCTD12 KCTD12 | KCTD12 pS176 |
| BTB/POZ domain-containing protein KCTD12 KCTD12 | KCTD12 seq: 185-205 + Phospho (ST) |
| BUD13 homolog BUD13 | BUD13 pS271 |
| Calmin CLMN | CLMN pS419 |
| Calmodulin-regulated spectrin-associated protein 1 CAMSAP1 | CAMSAP1 pS629 |

TABLE 1-continued

| Phosphoprotein | Phosphorylation site |
|---|---|
| Calmodulin-regulated spectrin-associated protein 1 CAMSAP1 | CAMSAP1 seq: 498-523 + Phospho (ST) |
| Calpastatin CAST | CAST pS243 |
| Calpastatin CAST | CAST pS660 |
| Calpastatin CAST | CAST seq: 212-249 + Phospho (ST) |
| cAMP-dependent protein kinase type II-alpha regulatory subunit PRKAR2A | PRKAR2A pS58 |
| CapZ-interacting protein RCSD1 | RCSD1 pS68 |
| CapZ-interacting protein RCSD1 | RCSD1 seq: 177-188 + Phospho (ST) |
| Caspase recruitment domain-containing protein 9 CARD9 | CARD9 pS460 |
| Cation-independent mannose-6-phosphate recept | IGF2R pS2409 |
| Cation-independent mannose-6-phosphate receptor IGF2R | IGF2R pS2409 |
| Cation-independent mannose-6-phosphate receptor IGF2R | IGF2R pS2484 |
| Cation-independent mannose-6-phosphate receptor IGF2R | IGF2R seq: 2398-2420 + Phospho (ST) |
| C-C motif chemokine 13 CCL13 | CCL13 seq: 42-47 + Phospho (ST) |
| CCAAT/enhancer-binding protein beta CEBPB | CEBPB seq: 209-242 + Phospho (ST) |
| CD2-associated protein CD2AP | CD2AP seq: 505-517 + Phospho (ST) |
| CD97 antigen CD97 | CD97 pS831 |
| Cdc42 effector protein 3 CDC42EP3 | CDC42EP3 pS89 |
| Cdc42 effector protein 3 CDC42EP3 | CDC42EP3 seq: 87-104 + Phospho (ST) |
| Chloride intracellular channel protein 1 CLIC1 | CLIC1 pS156 |
| Choline-phosphate cytidylyltransferase A PCYT1A | PCYT1A pS343 |
| Chromatin target of PRMT1 protein CHTOP | CHTOP pS40 |
| Chromodomain-helicase-DNA-binding protein 4 CHD4 | CHD4 seq: 354-390 + Phospho (ST) |
| Chromodomain-helicase-DNA-binding protein 4 CHD4 | CHD4 seq: 354-390 + Phospho (Y) |
| C-Jun-amino-terminal kinase-interacting protein | SPAG9 pS203 pT217 |
| C-Jun-amino-terminal kinase-interacting protein 4 SPAG9 | SPAG9 pS203 pT217 |
| Cleavage and polyadenylation specificity factor subunit 2 CPSF2 | CPSF2 pS452 |
| Cleavage stimulation factor subunit 2 tau variant CSTF2T | CSTF2T seq: 554-576 + Phospho (ST) |
| Cleavage stimulation factor subunit 3 CSTF3 | CSTF3 pS691 |
| CLK4-associating serine/arginine rich protein CLASRP | CLASRP pS547 |
| C-myc promoter-binding protein DENND4A | DENND4A seq: 1013-1030 + Phospho (ST) |
| C-myc promoter-binding protein DENND4A | DENND4A seq: 1149-1160 + Phospho (ST) |
| C-myc promoter-binding protein DENND4A | DENND4A seq: 1508-1526 + Phospho (ST) |
| C-myc promoter-binding protein DENND4A | DENND4A seq: 1587-1601 + Phospho (ST) |
| Coiled-coil domain-containing protein 12 CCDC12 | CCDC12 pS165 |
| Coiled-coil domain-containing protein 6 CCDC6 | CCDC6 pS240 pS244 |
| Coiled-coil domain-containing protein 86 CCDC86 | CCDC86 pS18 |
| Coiled-coil domain-containing protein 88B CCDC88B | CCDC88B pS1379 |
| Coiled-coil domain-containing protein 88B CCDC88B | CCDC88B pS1408 |
| Coiled-coil domain-containing protein 88B CCDC88B | CCDC88B seq: 429-454 + Phospho (ST) |
| Coiled-coil domain-containing protein 88B CCDC88B | CCDC88B seq: 595-613 + 2 Phospho (ST) |
| Coiled-coil domain-containing protein 88B CCDC88B | CCDC88B seq: 595-613 + Phospho (ST) |
| Coiled-coil-helix-coiled-coil-helix domain-containing protein 3, mitochondrial CHCHD3 | CHCHD3 seq: 49-64 + Phospho (ST) |
| Collagen type IV alpha-3-binding protein COL4A3BP | COL4A3BP pS373 |
| COP9 signalosome complex subunit 7a COPS7A | COPS7A seq: 222-243 + Phospho (ST) |
| Coronin-7 CORO7 | CORO7 pS21 |
| Coronin-7 CORO7 | CORO7 pS465 |
| Crk-like protein CRKL | CRKL seq: 105-129 + Phospho (ST) |

TABLE 1-continued

| Phosphoprotein | Phosphorylation site |
| --- | --- |
| Cyclin-dependent kinase 11A CDK11A | CDK11A pS271 |
| Cyclin-dependent kinase 13 CDK13 | CDK13 pS437 pS439 |
| Cyclin-dependent kinase 9 CDK9 | CDK9 pS347 |
| Cyclin-L1 CCNL1 | CCNL1 pS352 |
| Cyclin-Y-like protein 1 CCNYL1 | CCNYL1 pS344 |
| Cytohesin-4 CYTH4 | CYTH4 pS215 |
| Cytoplasmic dynein 1 heavy chain 1 DYNC1H1 | DYNC1H1 pS4368 |
| Cytoplasmic dynein 1 heavy chain 1 DYNC1H1 | DYNC1H1 seq: 4366-4378 + Phospho (ST) |
| Cytoplasmic dynein 1 light intermediate chain 1 DYNC1LI1 | DYNC1LI1 seq: 412-428 + Phospho (ST) |
| Death domain-associated protein 6 DAXX | DAXX pS495 |
| Death domain-associated protein 6 DAXX | DAXX pS690 |
| Dedicator of cytokinesis protein 10 DOCK10 | DOCK10 pS12 |
| Dedicator of cytokinesis protein 10 DOCK10 | DOCK10 pT1440 |
| Dedicator of cytokinesis protein 10 DOCK10 | DOCK10 pT196 |
| Dedicator of cytokinesis protein 10 DOCK10 | DOCK10 seq: 12-23 + Phospho (ST) |
| Dedicator of cytokinesis protein 11 DOCK11 | DOCK11 pS12 |
| Dedicator of cytokinesis protein 8 DOCK8 | DOCK8 pS451 |
| Dedicator of cytokinesis protein 8 DOCK8 | DOCK8 seq: 900-920 + Phospho (ST) |
| DENN domain-containing protein 1A DENND1A | DENND1A seq: 518-531 + 2 Phospho (ST) |
| DENN domain-containing protein 1A DENND1A | DENND1A seq: 518-531 + Phospho (ST) |
| DENN domain-containing protein 1C DENND1C | DENND1C pS596 |
| DENN domain-containing protein 1C DENND1C | DENND1C pS619 |
| DENN domain-containing protein 5A DENND5A | DENND5A pS193 |
| Deoxynucleoside triphosphate triphosphohydrolase SAMH | SAMHD1 pS102 |
| Deoxynucleoside triphosphate triphosphohydrolase SAMH | SAMHD1 pT592 |
| Deoxynucleoside triphosphate triphosphohydrolase SAMHD1 SAMHD1 | SAMHD1 pS33 |
| Deoxynucleoside triphosphate triphosphohydrolase SAMHD1 SAMHD1 | SAMHD1 pT592 |
| Deoxynucleoside triphosphate triphosphohydrolase SAMHD1 SAMHD1 | SAMHD1 seq: 15-43 + 2 Phospho (ST) |
| Deoxynucleoside triphosphate triphosphohydrolase SAMHD1 SAMHD1 | SAMHD1 seq: 21-43 + 2 Phospho (ST) |
| DEP domain-containing mTOR-interacting protein DEPTOR | DEPTOR seq: 227-249 + Phospho (ST) |
| Dihydropyrimidinase-related protein | DPYSL2 seq: 533-552 + Phospho (ST) |
| Dihydropyrimidinase-related protein 2 DPYSL2 | DPYSL2 seq: 533-552 + Phospho (ST) |
| Disks large-associated protein 4 DLGAP4 | DLGAP4 seq: 971-991 + Gln−>pyro-Glu (N-term Q); Phospho (ST) |
| DmX-like protein 2 DMXL2 | DMXL2 pS1400 |
| DmX-like protein 2 DMXL2 | DMXL2 seq: 2397-2414 + Phospho (ST) |
| DmX-like protein 2 DMXL2 | DMXL2 seq: 941-969 + Phospho (ST) |
| DNA replication complex GINS protein PSF2 GINS2 | GINS2 pS182 |
| DNA replication licensing factor MCM2 MCM2 | MCM2 pS139 |
| DNA replication licensing factor MCM3 MCM3 | MCM3 pS711 pT722 |
| DNA replication licensing factor MCM3 MCM3 | MCM3 seq: 701-724 + Phospho (ST); Phospho (Y) |
| DNA topoisomerase 2-alpha TOP2A | TOP2A seq: 1374-1411 + Phospho (ST) |
| DNA topoisomerase 2-beta TOP2B | TOP2B pS1400 pS1424 |
| DNA-binding protein SATB1 SATB1 | SATB1 pS637 |
| DNA-dependent protein kinase catalytic subunit PRKDC | PRKDC pS2612 |
| DNA-dependent protein kinase catalytic subunit PRKDC | PRKDC pT2638 |
| DNA-dependent protein kinase catalytic subunit PRKDC | PRKDC seq: 3197-3217 + Phospho (ST) |
| DNA-directed RNA polymerase I subunit RPA43 TWISTNB | TWISTNB pS304 |
| DNA-directed RNA polymerase I subunit RPA43 TWISTNB | TWISTNB pS328 |
| Docking protein 3 DOK3 | DOK3 pS483 |
| Docking protein 3 DOK3 | DOK3 seq: 388-424 + Phospho (Y) |

TABLE 1-continued

| Phosphoprotein | Phosphorylation site |
|---|---|
| Double-strand break repair protein MRE11A MRE11A | MRE11A seq: 674-682 + Phospho (ST) |
| Drebrin-like protein DBNL | DBNL pS141 |
| Drebrin-like protein DBNL | DBNL pS232 |
| Drebrin-like protein DBNL | DBNL pS269 |
| Drebrin-like protein DBNL | DBNL pS283 |
| Drebrin-like protein DBNL | DBNL seq: 149-164 + Phospho (Y) |
| Drebrin-like protein DBNL | DBNL seq: 267-280 + 2 Phospho (ST) |
| Dual adapter for phosphotyrosine and 3-phosphotyrosine and 3-phosphoinositide DAPP1 | DAPP1 seq: 274-280 + Phospho (ST) |
| Dual specificity mitogen-activated protein kinase kinase 7 MAP2K7 | MAP2K7 seq: 55-72 + Phospho (ST) |
| Dual specificity protein kinase CLK1 CLK1 | CLK1 pS140 |
| E3 SUMO-protein ligase RanBP2 RANBP2 | RANBP2 pS1509 |
| E3 SUMO-protein ligase RanBP2 RANBP2 | RANBP2 seq: 1507-1522 + Phospho (ST) |
| E3 ubiquitin/ISG15 ligase TRIM25 TRIM25 | TRIM25 pS100 |
| E3 ubiquitin-protein ligase BRE1A RNF20 | RNF20 pS138 |
| E3 ubiquitin-protein ligase BRE1A RNF20 | RNF20 seq: 125-142 + Phospho (ST) |
| E3 ubiquitin-protein ligase BRE1A RNF20 | RNF20 seq: 515-551 + Phospho (ST) |
| E3 ubiquitin-protein ligase HECTD1 HECTD1 | HECTD1 seq: 1382-1403 + Phospho (ST) |
| E3 ubiquitin-protein ligase HUWE1 HUWE1 | HUWE1 seq: 1084-1099 + Phospho (ST) |
| E3 ubiquitin-protein ligase HUWE1 HUWE1 | HUWE1 seq: 2522-2538 + Phospho (ST) |
| E3 ubiquitin-protein ligase MYCBP2 MYCBP2 | MYCBP2 pS2833 |
| E3 ubiquitin-protein ligase MYCBP2 MYCBP2 | MYCBP2 pS3440 |
| E3 ubiquitin-protein ligase MYCBP2 MYCBP2 | MYCBP2 pS3467 |
| E3 ubiquitin-protein ligase MYCBP2 MYCBP2 | MYCBP2 seq: 1584-1596 + Gln–>pyro-Glu (N-term Q); Phospho (ST) |
| E3 ubiquitin-protein ligase RBBP6 RBBP6 | RBBP6 pS1277 |
| E3 ubiquitin-protein ligase RNF213 RNF213 | RNF213 pS217 |
| E3 ubiquitin-protein ligase TRIM22 TRIM22 | TRIM22 seq: 383-396 + Phospho (ST) |
| E3 ubiquitin-protein ligase TRIP12 TRIP12 | TRIP12 pS1577 |
| E3 ubiquitin-protein ligase ZFP91 ZFP91 | ZFP91 seq: 81-100 + Phospho (ST) |
| E3 ubiquitin-protein ligase ZNRF2 ZNRF2 | ZNRF2 pS82 |
| Echinoderm microtubule-associated protein-like 3 EML3 | EML3 seq: 191-205 + Phospho (ST) |
| EF-hand domain-containing protein D2 EFHD2 | EFHD2 pS74 |
| EF-hand domain-containing protein D2 EFHD2 | EFHD2 seq: 62-77 + Phospho (ST) |
| EF-hand domain-containing protein D2 EFHD2 | EFHD2 seq: 63-78 + Phospho (ST) |
| EH domain-binding protein 1-like protein 1 EHBP1L1 | EHBP1L1 pS1257 |
| EH domain-binding protein 1-like protein 1 EHBP1L1 | EHBP1L1 pS310 |
| EH domain-binding protein 1-like protein 1 EHBP1L1 | EHBP1L1 seq: 1270-1278 + Phospho (ST) |
| EH domain-binding protein 1-like protein 1 EHBP1L1 | EHBP1L1 seq: 1270-1278 + Phospho (ST) |
| Elongation factor 1-gamma EEF1G | EEF1G pT46 |
| Elongation factor 1-gamma EEF1G | EEF1G seq: 46-51 + Phospho (ST) |
| Elongation factor 1-gamma EEF1G | EEF1G seq: 46-51 + Phospho (ST) |
| Eomesodermin homolog EOMES | EOMES seq: 105-133 + Phospho (ST) |
| Ephrin type-B receptor 3 EPHB3 | EPHB3 seq: 669-676 + Phospho (ST) |
| Epidermal growth factor receptor substrate 15 EPS15 | EPS15 seq: 562-584 + Phospho (ST) |
| Epsin-1 EPN1 | EPN1 seq: 446-468 + Phospho (ST) |
| Eukaryotic translation initiation factor 4 gamma | EIF4G1 pS1092 |
| Eukaryotic translation initiation factor 4 gamma 1 EIF4G1 | EIF4G1 pS1092 |
| Eukaryotic translation initiation factor 4 gamma 1 EIF4G1 | EIF4G1 pS1231 |
| Eukaryotic translation initiation factor 4B EIF4B | EIF4B pS283 |

TABLE 1-continued

| Phosphoprotein | Phosphorylation site |
|---|---|
| Eukaryotic translation initiation factor 4B EIF4B | EIF4B seq: 280-287 + Phospho (ST) |
| Eukaryotic translation initiation factor 4E-binding protein 1 EIF4EBP1 | EIF4EBP1 seq: 64-99 + 2 Phospho (ST) |
| Eukaryotic translation initiation factor 4H EIF4H | EIF4H pS21 |
| FACT complex subunit SSRP1 SSRP1 | SSRP1 pS444 |
| Far upstream element-binding protein 2 KHSRP | KHSRP pS125 |
| Far upstream element-binding protein 3 FUBP3 | FUBP3 pS569 |
| Fatty aldehyde dehydrogena | ALDH3A2 pS293 |
| Fatty aldehyde dehydrogenase ALDH3A2 | ALDH3A2 pS293 |
| Filamin-A FLNA | FLNA seq: 1072-1087 + Phospho (ST) |
| Filamin-A FLNA | FLNA seq: 2521-2540 + Phospho (ST) |
| Filamin-B FLNB | FLNB pS2107 |
| Filamin-B FLNB | FLNB pS2481 |
| Filamin-B FLNB | FLNB seq: 2476-2495 + Phospho (ST) |
| FK506-binding protein 15 FKBP15 | FKBP15 seq: 1009-1036 + Phospho (ST) |
| FK506-binding protein 15 FKBP15 | FKBP15 seq: 344-361 + Phospho (ST) |
| FK506-binding protein 15 FKBP15 | FKBP15 seq: 954-974 + Phospho (ST) |
| Forkhead box protein K1 FOXK1 | FOXK1 pS441 |
| Forkhead box protein K2 FOXK2 | FOXK2 seq: 369-395 + Phospho (ST) |
| Formin-binding protein 4 FNBP4 | FNBP4 pS18 |
| Formin-binding protein 4 FNBP4 | FNBP4 seq: 448-453 + Oxidation (M); Phospho (ST) |
| Friend leukemia integration 1 transcription factor FLI1 | FLI1 pS241 |
| FYN-binding protein FYB | FYB pS46 |
| FYVE, RhoGEF and PH domain-containing protein 3 FGD3 | FGD3 pS547 |
| FYVE, RhoGEF and PH domain-containing protein 3 FGD3 | FGD3 seq: 540-550 + Phospho (ST) |
| GA-binding protein alpha chain GABPA | GABPA pS62 |
| Gamma-enolase ENO2 | ENO2 pY44 |
| GEM-interacting protein GMIP | GMIP pS437 |
| GEM-interacting protein GMIP | GMIP pS914 |
| GEM-interacting protein GMIP | GMIP seq: 231-248 + Phospho (ST) |
| General transcription factor IIF subunit 1 GTF2F1 | GTF2F1 seq: 425-435 + Phospho (ST) |
| Genetic suppressor element 1 GSE1 | GSE1 pS909 |
| Girdin CCDC88A | CCDC88A pS1417 |
| Girdin CCDC88A | CCDC88A seq: 1417-1424 + Phospho (ST) |
| Glycerol-3-phosphate acyltransferase 3 AGPAT9 | AGPAT9 pS68 |
| Glycogen [starch] synthase, muscle GYS1 | GYS1 seq: 709-737 + Phospho (ST) |
| Glycogen synthase kinase-3 alpha GSK3A | GSK3A seq: 19-50 + Phospho (ST) |
| Golgin subfamily A member 4 GOLGA4 | GOLGA4 pS71 |
| Golgin subfamily B member 1 GOLGB1 | GOLGB1 seq: 3008-3031 + Phospho (ST) |
| GPALPP motifs-containing protein 1 GPALPP1 | GPALPP1 pS105 |
| G-protein-signaling modulator 3 GPSM3 | GPSM3 pS39 |
| GRIP1-associated protein 1 GRIPAP1 | GRIPAP1 seq: 688-714 + Phospho (ST) |
| GTPase-activating protein and VPS9 domain-containing protein 1 GAPVD1 | GAPVD1 seq: 900-910 + Phospho (ST) |
| GTPase-activating protein and VPS9 domain-containing protein 1 GAPVD1 | GAPVD1 seq: 902-910 + Phospho (ST) |
| H(+)/Cl(−) exchange transporter 7 CLCN7 | CLCN7 pS9 |
| Hamartin TSC1 | TSC1 pS505 |
| HEAT repeat-containing protein 5B HEATR5B | HEATR5B seq: 1562-1578 + Phospho (ST) |
| Hematopoietic lineage cell-specific protein HCLS1 | HCLS1 pS275 |
| Hematopoietic lineage cell-specific protein HCLS1 | HCLS1 pT308 |
| Hematopoietic lineage cell-specific protein HCLS1 | HCLS1 pT333 |
| Hematopoietic lineage cell-specific protein HCLS1 | HCLS1 pY198 |
| Heme oxygenase 1 HMOX1 | HMOX1 pS229 |
| Hemogen HEMGN | HEMGN seq: 190-217 + Phospho (ST) |
| Hepatoma-derived growth factor-related protein 2 HDGFRP2 | HDGFRP2 pS454 |

TABLE 1-continued

| Phosphoprotein | Phosphorylation site |
|---|---|
| Heterochromatin protein 1-binding protein 3 HP1BP3 | HP1BP3 pS142 |
| Heterochromatin protein 1-binding protein 3 HP1BP3 | HP1BP3 pS156 |
| Heterogeneous nuclear ribonucleoprotein A/B HNRNPAB | HNRNPAB pS242 |
| Heterogeneous nuclear ribonucleoprotein A1 HNRNPA1 | HNRNPA1 seq: 337-352 + Phospho (ST) |
| Heterogeneous nuclear ribonucleoprotein A3 HNRNPA3 | HNRNPA3 pS112 pS116 |
| Heterogeneous nuclear ribonucleoprotein A3 HNRNPA3 | HNRNPA3 seq: 110-126 + Phospho (ST) |
| Heterogeneous nuclear ribonucleoprotein F HNRNPF | HNRNPF seq: 180-192 + Phospho (ST) |
| Heterogeneous nuclear ribonucleoprotein H HNRNPH1 | HNRNPH1 pS23 |
| Heterogeneous nuclear ribonucleoprotein K HNRNPK | HNRNPK pS77 |
| Heterogeneous nuclear ribonucleoprotein M HNRNPM | HNRNPM pS633 |
| Heterogeneous nuclear ribonucleoprotein U HNRNPU | HNRNPU pS271 |
| Heterogeneous nuclear ribonucleoprotein U HNRNPU | HNRNPU pS59 |
| Heterogeneous nuclear ribonucleoproteins C1/C2 HNRNPC | HNRNPC pS138 |
| Heterogeneous nuclear ribonucleoproteins C1/C2 HNRNPC | HNRNPC pS299 |
| Heterogeneous nuclear ribonucleoproteins C1/C2 HNRNPC | HNRNPC seq: 251-288 + Phospho (ST) |
| Hexokinase-3 HK3 | HK3 seq: 11-41 + Phospho (ST) |
| High affinity immunoglobulin epsilon receptor subunit gamma FCER1G | FCER1G pT78 |
| High mobility group protein 20A HMG20A | HMG20A pS105 |
| Histone deacetylase 1 HDAC1 | HDAC1 pS393 |
| Histone deacetylase 1 HDAC1 | HDAC1 seq: 405-413 + Phospho (ST) |
| Histone deacetylase 2 HDAC2 | HDAC2 pS394 |
| Histone deacetylase 4 HDAC4 | HDAC4 seq: 465-492 + Phospho (ST) |
| Histone deacetylase 4 HDAC4 | HDAC4 seq: 630-651 + Phospho (ST) |
| Histone H1.1 HIST1H1A | HIST1H1A pS107 |
| Histone H1.5 HIST1H1B | HIST1H1B pS81 |
| Histone H1.5 HIST1H1B | HIST1H1B seq: 101-109 + Phospho (ST) |
| Histone-lysine N-methyltransferase 2A KMT2A | KMT2A seq: 504-527 + Phospho (ST) |
| Histone-lysine N-methyltransferase 2D KMT2D | KMT2D seq: 6-50 + Phospho (ST) |
| HMG box transcription factor BBX BBX | BBX pS844 |
| Huntingtin HTT | HTT pS1874 |
| Huntingtin HTT | HTT seq: 417-437 + 2 Phospho (ST) |
| Hyaluronan and proteoglycan link protein 4 HAPLN4 | HAPLN4 pS111 |
| Inactive rhomboid protein | RHBDF2 seq: 88-95 + Phospho (ST) |
| Inactive rhomboid protein 2 RHBDF2 | RHBDF2 pS113 |
| Inactive rhomboid protein 2 RHBDF2 | RHBDF2 seq: 88-95 + Phospho (ST) |
| Inhibitor of nuclear factor kappa-B kinase subunit beta IKBKB | IKBKB pS672 |
| Inhibitor of nuclear factor kappa-B kinase subunit beta IKBKB | IKBKB seq: 681-704 + Phospho (ST) |
| Inositol hexakisphosphate and diphosphoinositol-pentakisphosphate kinase 2 PPIP5K2 | PPIP5K2 pS1006 |
| Insulin receptor substrate 2 IRS2 | IRS2 pS577 |
| Insulin receptor substrate 2 IRS2 | IRS2 pS594 |
| Insulin receptor substrate 2 IRS2 | IRS2 seq: 603-611 + Phospho (ST) |
| Interferon regulatory factor 2-binding protein 2 IRF2BP2 | IRF2BP2 seq: 237-252 + Phospho (ST) |
| Interleukin enhancer-binding factor 3 ILF3 | ILF3 pS190 |
| Interleukin enhancer-binding factor 3 ILF3 | ILF3 seq: 183-200 + Phospho (ST) |

TABLE 1-continued

| Phosphoprotein | Phosphorylation site |
|---|---|
| Interleukin enhancer-binding factor 3 ILF3 | ILF3 seq: 475-523 + Phospho (ST) |
| Interleukin-1 receptor-associated kinase 3 IRAK3 | IRAK3 pS110 |
| Interleukin-1 receptor-associated kinase 3 IRAK3 | IRAK3 seq: 505-526 + Phospho (ST) |
| Interleukin-17 receptor A IL17RA | IL17RA pS708 |
| Intersectin-2 ITSN2 | ITSN2 pY968 |
| IQ motif and SEC7 domain-containing protein 1 IQSEC1 | IQSEC1 pS512 |
| IQ motif and SEC7 domain-containing protein 2 IQSEC2 | IQSEC2 pS1133 |
| IQ motif and SEC7 domain-containing protein 2 IQSEC2 | IQSEC2 seq: 212-235 + Phospho (ST) |
| KH domain-containing, RNA-binding, signal transduction-associated protein 1 KHDRBS1 | KHDRBS1 seq: 18-31 + Oxidation (M); Phospho (ST) |
| KH domain-containing, RNA-binding, signal transduction-associated protein 1 KHDRBS1 | KHDRBS1 seq: 18-31 + Phospho (ST) |
| Krueppel-like factor | KLF4 seq: 315-328 + Phospho (ST) |
| Krueppel-like factor 4 KLF4 | KLF4 seq: 315-328 + Phospho (ST) |
| Lamina-associated polypeptide 2, isoform alpha TMPO | TMPO seq: 291-315 + Phospho (ST) |
| Lamina-associated polypeptide 2, isoforms beta/gamma TMPO | TMPO seq: 216-239 + Phospho (ST) |
| Lamin-B receptor LBR | LBR pS99 |
| Lamin-B1 LMNB1 | LMNB1 pS200 |
| Lamin-B1 LMNB1 | LMNB1 pS52 |
| Lamin-B1 LMNB1 | LMNB1 pT575 |
| Lamin-B1 LMNB1 | LMNB1 seq: 15-26 + Phospho (ST) |
| Lamin-B1 LMNB1 | LMNB1 seq: 272-290 + Phospho (ST) |
| Lamin-B1 LMNB1 | LMNB1 seq: 277-290 + Phospho (ST) |
| Lamin-B1 LMNB1 | LMNB1 seq: 52-67 + Phospho (ST) |
| Lamin-B2 LMNB2 | LMNB2 pS17 |
| Lamin-B2 LMNB2 | LMNB2 pS296 |
| La-related protein 1 LARP1 | LARP1 pS75 |
| La-related protein 1 LARP1 | LARP1 pS90 |
| La-related protein 1 LARP1 | LARP1 pT526 |
| La-related protein 1 LARP1 | LARP1 seq: 822-839 + Phospho (ST) |
| La-related protein 4B LARP4B | LARP4B pS498 |
| Late secretory pathway protein AVL9 homolog AVL9 | AVL9 seq: 243-278 + Phospho (ST) |
| Leucine-rich repeat and calponin homology domain-containing protein 4 LRCH4 | LRCH4 pS432 |
| Leucine-rich repeat and calponin homology domain-containing protein 4 LRCH4 | LRCH4 seq: 266-293 + Phospho (ST) |
| Leucine-rich repeat and calponin homology domain-containing protein 4 LRCH4 | LRCH4 seq: 311-327 + Phospho (ST) |
| Leucine-rich repeat flightless-interacting protein 1 LRRFIP1 | LRRFIP1 pS768 |
| Leucine-rich repeat flightless-interacting protein 1 LRRFIP1 | LRRFIP1 seq: 762-789 + Phospho (ST) |
| Leucine-rich repeat flightless-interacting protein 1 LRRFIP1 | LRRFIP1 seq: 763-789 + Phospho (ST) |
| Leukocyte immunoglobulin-like receptor subfamily B member 1 LILRB1 | LILRB1 pS579 |
| Leukocyte immunoglobulin-like receptor subfamily B member | LILRB2 seq: 521-537 + Phospho (ST) |
| Leukocyte immunoglobulin-like receptor subfamily B member 2 LILRB2 | LILRB2 seq: 521-537 + Phospho (ST) |
| Leukocyte immunoglobulin-like receptor subfamily B member 3 LILRB3 | LILRB3 seq: 501-518 + Phospho (ST) |
| Leukocyte immunoglobulin-like receptor subfamily B member 3 LILRB3 | LILRB3 seq: 502-518 + Phospho (ST) |
| Leukocyte immunoglobulin-like receptor subfamily B member 4 LILRB4 | LILRB4 seq: 317-334 + Phospho (ST) |
| Leukocyte immunoglobulin-like receptor subfamily B member 5 LILRB5 | LILRB5 pS559 |
| Leukotriene B4 receptor 1 LTB4R | LTB4R seq: 304-316 + Phospho (ST) |
| LIM domain-binding protein 1 LDB1 | LDB1 pS302 |
| LIM domain-binding protein 1 LDB1 | LDB1 seq: 300-320 + Oxidation (M); Phospho (ST) |

TABLE 1-continued

| Phosphoprotein | Phosphorylation site |
|---|---|
| LIM domain-binding protein 1 LDB1 | LDB1 seq: 300-320 + Phospho (ST) |
| Linker for activation of T-cells family member 1 LAT | LAT pS224 |
| Liprin-alpha-1 PPFIA1 | PPFIA1 pS763 |
| Liprin-beta-2 PPFIBP2 | PPFIBP2 pS387 |
| Liprin-beta-2 PPFIBP2 | PPFIBP2 seq: 383-392 + Phospho (ST) |
| Lymphoid-restricted membrane protein LRMP | LRMP pS363 |
| Lymphoid-restricted membrane protein LRMP | LRMP seq: 361-372 + 2 Phospho (ST) |
| Lysine-specific demethylase 2B KDM2B | KDM2B pS1031 |
| Lysine-specific histone demethylase 1A KDM1A | KDM1A pS166 |
| Lysosomal-trafficking regulator LYST | LYST pS2105 |
| Lysosomal-trafficking regulator LYST | LYST pS2124 |
| Lysosomal-trafficking regulator LYST | LYST pS2149 |
| Lysosomal-trafficking regulator LYST | LYST pS2264 |
| Lysosomal-trafficking regulator LYST | LYST seq: 2103-2120 + Phospho (ST) |
| Major vault protein MVP | MVP pS445 |
| Major vault protein MVP | MVP seq: 862-893 + Phospho (ST) |
| Manganese-transporting ATPase 13A1 ATP13A1 | ATP13A1 pS935 |
| MAP kinase-activating death domain protein MADD | MADD seq: 1236-1255 + Phospho (ST) |
| MAP7 domain-containing protein 1 MAP7D1 | MAP7D1 pS442 |
| Mediator of DNA damage checkpoint protein 1 MDC1 | MDC1 seq: 1563-1584 + 2 Phospho (ST) |
| Mediator of DNA damage checkpoint protein 1 MDC1 | MDC1 seq: 360-393 + Phospho (ST) |
| Membrane magnesium transporter 1 MMGT1 | MMGT1 seq: 99-122 + Phospho (ST) |
| Membrane-associated phosphatidylinositol transfer protein 1 PITPNM1 | PITPNM1 seq: 662-685 + Phospho (ST) |
| Microtubule-actin cross-linking factor 1, isoforms 1/2/3/5 MACF1 | MACF1 seq: 7328-7360 + Phospho (ST) |
| Microtubule-associated protein 1A MAP1A | MAP1A pS1069 |
| Microtubule-associated protein 1A MAP1A | MAP1A pS1776 |
| Microtubule-associated protein 1S MAP1S | MAP1S pS546 |
| Microtubule-associated protein 4 MAP4 | MAP4 pS1073 |
| Microtubule-associated protein 4 MAP4 | MAP4 pS928 |
| Microtubule-associated serine/threonine-protein kinase 2 MAST2 | MAST2 seq: 1254-1274 + Phospho (ST) |
| Mini-chromosome maintenance complex-binding protein MCMBP | MCMBP pS154 |
| Mini-chromosome maintenance complex-binding protein MCMBP | MCMBP pS298 |
| Minor histocompatibility protein HA-1 HMHA1 | HMHA1 pS23 |
| Minor histocompatibility protein HA-1 HMHA1 | HMHA1 pS619 |
| Minor histocompatibility protein HA-1 HMHA1 | HMHA1 pS619 |
| Minor histocompatibility protein HA-1 HMHA1 | HMHA1 pS73 |
| Minor histocompatibility protein HA-1 HMHA1 | HMHA1 pS73 |
| Minor histocompatibility protein HA-1 HMHA1 | HMHA1 seq: 576-606 + 2 Phospho (ST) |
| Minor histocompatibility protein HA-1 HMHA1 | HMHA1 seq: 576-606 + Phospho (ST) |
| Minor histocompatibility protein HA-1 HMHA1 | HMHA1 seq: 619-641 + Phospho (ST) |
| Mitochondrial inner membrane protein IMMT | IMMT pS113 |
| Mitogen-activated protein kinase 1 MAPK1 | MAPK1 pY187 |
| Mitogen-activated protein kinase 1 MAPK1 | MAPK1 seq: 173-191 + Phospho (ST) |
| Mitogen-activated protein kinase kinase kinase 2 MAP3K2 | MAP3K2 pS153 |
| Mitogen-activated protein kinase kinase kinase 2 MAP3K2 | MAP3K2 pS239 |
| Mitogen-activated protein kinase kinase kinase 2 MAP3K2 | MAP3K2 seq: 161-179 + Phospho (ST) |
| Mitogen-activated protein kinase kinase kinase 2 MAP3K2 | MAP3K2 seq: 329-348 + Phospho (ST) |
| Mitogen-activated protein kinase kinase kinase 3 MAP3K3 | MAP3K3 pS166 |
| Mitogen-activated protein kinase kinase kinase 3 MAP3K3 | MAP3K3 seq: 144-161 + Phospho (ST) |
| Mitogen-activated protein kinase kinase kinase 3 MAP3K3 | MAP3K3 seq: 164-185 + 2 Phospho (ST) |
| MKL/myocardin-like protein 1 MKL1 | MKL1 pS385 |

TABLE 1-continued

| Phosphoprotein | Phosphorylation site |
|---|---|
| MKL/myocardin-like protein 1 MKL1 | MKL1 seq: 331-351 + Gln–>pyro-Glu (N-term Q); Phospho (ST) |
| MKL/myocardin-like protein 1 MKL1 | MKL1 seq: 331-351 + Phospho (ST) |
| Moesin MSN | MSN pS576 |
| Monocarboxylate transporter 4 SLC16A3 | SLC16A3 pS436 |
| Myb-binding protein 1A MYBBP1A | MYBBP1A pS1267 |
| Myb-binding protein 1A MYBBP1A | MYBBP1Aseq: 1255-1275 + Phospho (ST) |
| Myelin basic protein MBP | MBP seq: 109-138 + Phospho (ST) |
| Myeloid cell nuclear differentiation antigen MNDA | MNDA seq: 149-198 + Phospho (ST) |
| Myeloid cell nuclear differentiation antigen MNDA | MNDA seq: 151-198 + Phospho (ST) |
| Myotubularin-related protein 3 MTMR3 | MTMR3 pS647 |
| Myotubularin-related protein 3 MTMR3 | MTMR3 seq: 613-630 + Phospho (ST) |
| Myotubularin-related protein 3 MTMR3 | MTMR3 seq: 613-630 + Phospho (Y) |
| Myristoylated alanine-rich C-kinase substrate MARCKS | MARCKS pS170 |
| Na(+)/H(+) exchange regulatory cofactor NHE-RF1 SLC9A3R1 | SLC9A3R1 pS280 |
| N-acetyl-D-glucosamine kinase NAGK | NAGK pS76 |
| NAD kinase NADK | NADK pS46 |
| NAD kinase NADK | NADK pS64 |
| NAD kinase NADK | NADK seq: 44-57 + Phospho (ST) |
| NAD-dependent protein deacetylase sirtuin-2 SIRT2 | SIRT2 seq: 347-370 + Phospho (ST) |
| Nascent polypeptide-associated complex subunit alpha NACA | NACA pS166 |
| Nascent polypeptide-associated complex subunit alpha NACA | NACA pT161 |
| Nascent polypeptide-associated complex subunit alpha NACA | NACA seq: 143-179 + Phospho (ST) |
| Natural killer cell receptor 2B4 CD244 | CD244 pS334 |
| NEDD4-binding protein 1 N4BP1 | N4BP1 pS300 |
| Negative elongation factor E NELFE | NELFE pS131 |
| Neurabin-2 PPP1R9B | PPP1R9B seq: 98-112 + Phospho (ST) |
| Neurobeachin-like protein 2 NBEAL2 | NBEAL2 pS2739 |
| Neurobeachin-like protein 2 NBEAL2 | NBEAL2 pT1867 |
| Neurobeachin-like protein 2 NBEAL2 | NBEAL2 pT1869 |
| Neuroblast differentiation-associated protein AHN | AHNAK pS570 |
| Neuroblast differentiation-associated protein AHN | AHNAK seq: 204-225 + 2 Phospho (ST) |
| Neuroblast differentiation-associated protein AHN | AHNAK seq: 9-28 + Phospho (ST) |
| Neuroblast differentiation-associated protein AHNAK AHNAK | AHNAK pS115 |
| Neuroblast differentiation-associated protein AHNAK AHNAK | AHNAK pS135 |
| Neuroblast differentiation-associated protein AHNAK AHNAK | AHNAK pS177 |
| Neuroblast differentiation-associated protein AHNAK AHNAK | AHNAK pS210 |
| Neuroblast differentiation-associated protein AHNAK AHNAK | AHNAK pS210 pS216 |
| Neuroblast differentiation-associated protein AHNAK AHNAK | AHNAK pS3360 |
| Neuroblast differentiation-associated protein AHNAK AHNAK | AHNAK pS3426 |
| Neuroblast differentiation-associated protein AHNAK AHNAK | AHNAK pS41 |
| Neuroblast differentiation-associated protein AHNAK AHNAK | AHNAK pS4520 |
| Neuroblast differentiation-associated protein AHNAK AHNAK | AHNAK pS4986 |
| Neuroblast differentiation-associated protein AHNAK AHNAK | AHNAK pS5031 |
| Neuroblast differentiation-associated protein AHNAK AHNAK | AHNAK pS511 |
| Neuroblast differentiation-associated protein AHNAK AHNAK | AHNAK pS5110 |

TABLE 1-continued

| Phosphoprotein | Phosphorylation site |
|---|---|
| Neuroblast differentiation-associated protein AHNAK AHNAK | AHNAK pS5400 |
| Neuroblast differentiation-associated protein AHNAK AHNAK | AHNAK pS5448 |
| Neuroblast differentiation-associated protein AHNAK AHNAK | AHNAK pS5552 |
| Neuroblast differentiation-associated protein AHNAK AHNAK | AHNAK pS570 |
| Neuroblast differentiation-associated protein AHNAK AHNAK | AHNAK pS5720 |
| Neuroblast differentiation-associated protein AHNAK AHNAK | AHNAK pS5731 |
| Neuroblast differentiation-associated protein AHNAK AHNAK | AHNAK pS5739 |
| Neuroblast differentiation-associated protein AHNAK AHNAK | AHNAK pS5830 |
| Neuroblast differentiation-associated protein AHNAK AHNAK | AHNAK pS93 |
| Neuroblast differentiation-associated protein AHNAK AHNAK | AHNAK pS93 |
| Neuroblast differentiation-associated protein AHNAK AHNAK | AHNAK pT158 |
| Neuroblast differentiation-associated protein AHNAK AHNAK | AHNAK pT3716 |
| Neuroblast differentiation-associated protein AHNAK AHNAK | AHNAK pT4430 |
| Neuroblast differentiation-associated protein AHNAK AHNAK | AHNAK pT4564 |
| Neuroblast differentiation-associated protein AHNAK AHNAK | AHNAK pT4766 |
| Neuroblast differentiation-associated protein AHNAK AHNAK | AHNAK pT490 |
| Neuroblast differentiation-associated protein AHNAK AHNAK | AHNAK pY121 |
| Neuroblast differentiation-associated protein AHNAK AHNAK | AHNAK seq: 103-123 + Phospho (Y) |
| Neuroblast differentiation-associated protein AHNAK AHNAK | AHNAK seq: 204-225 + 2 Phospho (ST) |
| Neuroblast differentiation-associated protein AHNAK AHNAK | AHNAK seq: 208-225 + 2 Phospho (ST) |
| Neuroblast differentiation-associated protein AHNAK AHNAK | AHNAK seq: 4516-4532 + Phospho (ST) |
| Neuroblast differentiation-associated protein AHNAK AHNAK | AHNAK seq: 4899-4905 + Phospho (ST) |
| Neuroblast differentiation-associated protein AHNAK AHNAK | AHNAK seq: 5385-5405 + Phospho (ST) |
| Neuroblast differentiation-associated protein AHNAK AHNAK | AHNAK seq: 5630-5655 + Phospho (ST) |
| Neuroblast differentiation-associated protein AHNAK AHNAK | AHNAK seq: 5788-5812 + Phospho (ST) |
| Neuroblast differentiation-associated protein AHNAK AHNAK | AHNAK seq: 9-28 + Phospho (ST) |
| Neurofibromin NF1 | NF1 seq: 1137-1142 + Phospho (ST) |
| Neuropathy target esterase PNPLA6 | PNPLA6 pS411 |
| Neuropeptide B NPB | NPB seq: 49-54 + Phospho (ST) |
| Neutrophil cytosol factor | NCF1 pS348 |
| Neutrophil cytosol factor 1 NCF1 | NCF1 pS320 |
| Neutrophil cytosol factor 1 NCF1 | NCF1 pS348 |
| Neutrophil cytosol factor 1 NCF1 | NCF1 seq: 338-354 + Gln–>pyro-Glu (N-term Q); Phospho (ST) |
| Neutrophil cytosol factor 2 NCF2 | NCF2 pS332 |
| Neutrophil cytosol factor 2 NCF2 | NCF2 pS332 |
| Neutrophil cytosol factor 2 NCF2 | NCF2 pT233 |
| Neutrophil cytosol factor 2 NCF2 | NCF2 seq: 233-238 + Phospho (ST) |
| Neutrophil cytosol factor 2 NCF2 | NCF2 seq: 301-324 + Phospho (ST) |
| NHS-like protein 2 NHSL2 | NHSL2 seq: 190-196 + Phospho (ST) |
| NHS-like protein 2 NHSL2 | NHSL2 seq: 208-228 + Phospho (ST) |
| NHS-like protein 2 NHSL2 | NHSL2 seq: 318-331 + Phospho (ST) |
| Niban-like protein | FAM129B pS692 pS696 |
| Niban-like protein 1 FAM129B | FAM129B pS665 |

TABLE 1-continued

| Phosphoprotein | Phosphorylation site |
|---|---|
| Niban-like protein 1 FAM129B | FAM129B pS692 pS696 |
| Niban-like protein 1 FAM129B | FAM129B seq: 567-615 + Phospho (ST) |
| Niban-like protein 1 FAM129B | FAM129B seq: 686-705 + 2 Phospho (ST) |
| Niban-like protein 1 FAM129B | FAM129B seq: 686-705 + Phospho (ST) |
| Nibrin NBN | NBN pS397 |
| Non-POU domain-containing octamer-binding protein NONO | NONO pS147 |
| NSFL1 cofactor p47 NSFL1C | NSFL1C seq: 174-185 + Gln->pyro-Glu (N-term Q); Phospho (ST) |
| Nuclear distribution protein nudE homolog 1 NDE1 | NDE1 pS231 |
| Nuclear factor of activated T-cells, cytoplasmic 2 NFATC2 | NFATC2 seq: 216-223 + Phospho (ST) |
| Nuclear factor of activated T-cells, cytoplasmic 2 NFATC2 | NFATC2 seq: 325-338 + Phospho (ST) |
| Nuclear fragile X mental retardation-interacting protein 2 NUFIP2 | NUFIP2 pS629 |
| Nuclear fragile X mental retardation-interacting protein 2 NUFIP2 | NUFIP2 pS652 |
| Nuclear pore complex protein Nup214 NUP214 | NUP214 pS657 |
| Nuclear pore complex protein Nup50 NUP50 | NUP50 pS221 |
| Nuclear speckle splicing regulatory protein 1 NSRP1 | NSRP1 seq: 15-47 + Phospho (ST) |
| Nuclear ubiquitous casein and cyclin-dependent kinase substrate 1 NUCKS1 | NUCKS1 pS19 |
| Nuclear-interacting partner of ALK ZC3HC1 | ZC3HC1 pS321 |
| Nucleolar and coiled-body phosphoprotein 1 NOLC1 | NOLC1 pS698 |
| Nucleolar protein 56 NOP56 | NOP56 pS520 |
| Nucleolar protein 56 NOP56 | NOP56 pS570 |
| Nucleolar protein 56 NOP56 | NOP56 seq: 511-533 + Oxidation (M); Phospho (ST) |
| Nucleolar protein 56 NOP56 | NOP56 seq: 511-533 + Phospho (ST) |
| Nucleolar protein 58 NOP58 | NOP58 pS502 |
| Nucleolar protein 58 NOP58 | NOP58 pS502 pS514 |
| Nucleolar RNA helicase 2 DDX21 | DDX21 seq: 114-131 + Phospho (ST) |
| Nucleolin NCL | NCL pS619 |
| Nucleophosmin NPM1 | NPM1 pS125 |
| Nucleoprotein TPR TPR | TPR seq: 2133-2145 + Phospho (ST) |
| Nucleosome assembly protein 1-like 4 NAP1L4 | NAP1L4 pS125 |
| Opioid growth factor receptor OGFR | OGFR pS484 |
| OTU domain-containing protein 4 OTUD4 | OTUD4 pS416 |
| Oxysterol-binding protein-related protein 11 OSBPL11 | OSBPL11 pS172 |
| Oxysterol-binding protein-related protein 3 OSBPL3 | OSBPL3 pS437 |
| Paired amphipathic helix protein Sin3a SIN3A | SIN3A seq: 277-313 + Phospho (ST) |
| Palmitoyltransferase ZDHHC5 ZDHHC5 | ZDHHC5 pS621 |
| Palmitoyltransferase ZDHHC5 ZDHHC5 | ZDHHC5 seq: 296-322 + Phospho (ST) |
| Pantothenate kinase 2, mitochondrial PANK2 | PANK2 pS189 |
| Pantothenate kinase 2, mitochondrial PANK2 | PANK2 seq: 166-183 + Phospho (ST) |
| PAS domain-containing serine/threonine-protein kinase PASK | PASK seq: 113-132 + Phospho (ST) |
| Paxillin PXN | PXN pS106 |
| Paxillin PXN | PXN seq: 76-93 + Phospho (ST) |
| PDZ and LIM domain protein 2 PDLIM2 | PDLIM2 pS129 |
| PDZ and LIM domain protein 2 PDLIM2 | PDLIM2 pS161 |
| PDZ and LIM domain protein 2 PDLIM2 | PDLIM2 pS197 |
| PDZ and LIM domain protein 5 PDLIM5 | PDLIM5 seq: 305-324 + Phospho (ST) |
| Peptidyl-prolyl cis-trans isomerase FKBP3 FKBP3 | FKBP3 pS163 |
| Perilipin-5 PLIN5 | PLIN5 pS203 |
| Periphilin-1 PPHLN1 | PPHLN1 pS133 |
| PEST proteolytic signal-containing nuclear protein PCNP | PCNP pS119 |
| PHD finger protein 6 PHF6 | PHF6 seq: 134-157 + Phospho (ST) |

TABLE 1-continued

| Phosphoprotein | Phosphorylation site |
|---|---|
| PH-interacting protein PHIP | PHIP seq: 1554-1571 + Phospho (ST) |
| Phosphatase and actin regulator 2 PHACTR2 | PHACTR2 pS522 |
| Phosphatidylinositol 3,4,5-trisphosphate 5-phosphatase 1 INPP5D | INPP5D pS1085 |
| Phosphatidylinositol 3,4,5-trisphosphate 5-phosphatase 1 INPP5D | INPP5D pY1022 |
| Phosphatidylinositol 3,4,5-trisphosphate 5-phosphatase 1 INPP5D | INPP5D seq: 1085-1095 + Phospho (ST) |
| Phosphatidylinositol 3,4,5-trisphosphate 5-phosphatase 1 INPP5D | INPP5D seq: 883-891 + Phospho (ST) |
| Phosphatidylinositol 3,4,5-trisphosphate 5-phosphatase 1 INPP5D | INPP5D seq: 883-898 + Phospho (ST) |
| Phosphatidylinositol 3,4,5-trisphosphate 5-phosphatase 1 INPP5D | INPP5D seq: 931-957 + Phospho (ST) |
| Phosphatidylinositol 3,4,5-trisphosphate-dependent Rac exchanger 1 protein PREX1 | PREX1 pS319 |
| Phosphatidylinositol 4-kinase alpha PI4KA | PI4KA pS198 |
| Phosphatidylinositol 4-kinase alpha PI4KA | PI4KA seq: 196-210 + Phospho (ST) |
| Phosphatidylinositol 4-kinase type 2-alpha PI4K2A | PI4K2A seq: 460-472 + Phospho (ST) |
| Phosphofurin acidic cluster sorting protein 1 PACS1 | PACS1 seq: 399-421 + Phospho (ST) |
| Phosphoglycerate mutase 1 PGAM1 | PGAM1 pS14 |
| Phosphoinositide 3-kinase adapter protein 1 PIK3AP1 | PIK3AP1 pS656 |
| Phosphoinositide 3-kinase adapter protein 1 PIK3AP1 | PIK3AP1 pY694 |
| Phosphorylase b kinase regulatory subunit alpha, liver isoform PHKA2 | PHKA2 pS1015 |
| Phosphorylase b kinase regulatory subunit alpha, liver isoform PHKA2 | PHKA2 seq: 1039-1063 + 2 Phospho (ST) |
| Phosphorylase b kinase regulatory subunit beta PHKB | PHKB pS27 |
| Phosphorylase b kinase regulatory subunit beta PHKB | PHKB seq: 699-720 + Phospho (ST) |
| Phostensin PPP1R18 | PPP1R18 pS224 |
| Phostensin PPP1R18 | PPP1R18 pS368 |
| Phostensin PPP1R18 | PPP1R18 pS468 |
| Phostensin PPP1R18 | PPP1R18 seq: 468-477 + Phospho (ST) |
| Pinin PNN | PNN pS100 |
| Pituitary tumor-transforming gene 1 protein-interacting protein PTTG1IP | PTTG1IP pY174 |
| Plakophilin-2 PKP2 | PKP2 pS870 |
| Plastin-2 LCP1 | LCP1 pS5 |
| Plastin-2 LCP1 | LCP1 pT114 |
| Platelet receptor Gi | C10orf54 pS235 pS248 |
| Platelet receptor Gi | C10orf54 pS264 |
| Platelet receptor Gi24 C10orf54 | C10orf54 pS235 |
| Platelet receptor Gi24 C10orf54 | C10orf54 pS264 |
| Plectin PLEC | PLEC pS4384 pS4400 |
| Plectin PLEC | PLEC pS4406 |
| Plectin PLEC | PLEC seq: 4384-4401 + Phospho (ST) |
| Pogo transposable element with ZNF domain POGZ | POGZ seq: 1322-1341 + Phospho (ST) |
| Poly [ADP-ribose] polymerase 1 PARP1 | PARP1 seq: 356-394 + Phospho (ST) |
| Poly [ADP-ribose] polymerase 4 PARP4 | PARP4 pS1335 |
| Poly(rC)-binding protein 1 PCBP1 | PCBP1 pS264 |
| Poly(rC)-binding protein 1 PCBP1 | PCBP1 seq: 244-268 + Gln->pyro-Glu (N-term Q); Oxidation (M); Phospho (ST) |
| Poly(rC)-binding protein 2 PCBP2 | PCBP2 seq: 177-199 + Phospho (ST) |
| POTE ankyrin domain family member E POTEE | POTEE seq: 916-938 + Oxidation (M); Phospho (ST) |
| POTE ankyrin domain family member J POTEJ | POTEJ pT729 |
| POU domain, class 2, transcription factor 2 POU2F2 | POU2F2 pS55 |
| Pre-B-cell leukemia transcription factor 2 PBX2 | PBX2 pS330 |
| Prelamin-A/C LMNA | LMNA pS12 |
| Prelamin-A/C LMNA | LMNA pS636 |
| Prelamin-A/C LMNA | LMNA pS636 |
| Prelamin-A/C LMNA | LMNA seq: 645-654 + Phospho (ST) |

TABLE 1-continued

| Phosphoprotein | Phosphorylation site |
| --- | --- |
| Pre-mRNA 3'-end-processing factor FIP1 FIP1L1 | FIP1L1 pS492 |
| Pre-mRNA 3'-end-processing factor FIP1 FIP1L1 | FIP1L1 seq: 490-504 + Phospho (ST) |
| Prickle-like protein 1 PRICKLE1 | PRICKLE1 pS683 |
| Probable ATP-dependent RNA helicase DDX17 DDX17 | DDX17 seq: 569-587 + Phospho (ST) |
| Probable ATP-dependent RNA helicase DDX17 DDX17 | DDX17 seq: 671-684 + Phospho (ST) |
| Probable global transcription activator SNF2L2 SMARCA2 | SMARCA2 pS666 |
| Probable global transcription activator SNF2L2 SMARCA2 | SMARCA2 seq: 697-711 + Phospho (ST) |
| Probable phosphoglycerate mutase 4 PGAM4 | PGAM4 seq: 118-138 + Phospho (ST) |
| Probable phospholipid-transporting ATPase IF ATP11B | ATP11B pS1154 |
| Pro-interleukin-16 IL16 | IL16 pS845 |
| Pro-interleukin-16 IL16 | IL16 pS908 |
| Pro-interleukin-16 IL16 | IL16 pS946 |
| Pro-interleukin-16 IL16 | IL16 seq: 843-861 + Phospho (ST) |
| Proline-rich protein PRCC PRCC | PRCC seq: 147-166 + Phospho (ST) |
| Proline-serine-threonine phosphatase-interacting protein 1 PSTPIP1 | PSTPIP1 pS312 |
| Protein AATF AATF | AATF pS203 |
| Protein CBFA2T3 CBFA2T3 | CBFA2T3 seq: 327-343 + Phospho (ST) |
| Protein ELYS AHCTF1 | AHCTF1 pS1541 |
| Protein EVI2B EVI2B | EVI2B pS294 |
| Protein EVI2B EVI2B | EVI2B seq: 266-279 + 2 Phospho (ST) |
| Protein EVI2B EVI2B | EVI2B seq: 266-279 + Phospho (ST) |
| Protein FAM102B FAM102B | FAM102B pS228 |
| Protein FAM117A FAM117A | FAM117A pS29 |
| Protein FAM117A FAM117A | FAM117A pS67 |
| Protein FAM122A FAM122A | FAM122A seq: 187-203 + Phospho (ST) |
| Protein FAM65B FAM65B | FAM65B pS21 |
| Protein FAM65B FAM65B | FAM65B pS37 |
| Protein FAM65B FAM65B | FAM65B pS573 |
| Protein FAM65B FAM65B | FAM65B seq: 19-31 + Phospho (ST) |
| Protein FAM76B FAM76B | FAM76B pS193 |
| Protein FAM83B FAM83B | FAM83B pS766 |
| Protein flightless-1 homolog FLII | FLII pS856 |
| Protein HEXIM1 HEXIM1 | HEXIM1 seq: 51-86 + Phospho (ST) |
| Protein HIDE1 HIDE1 | HIDE1 seq: 209-227 + 2 Phospho (ST) |
| Protein Hook homolog 3 HOOK3 | HOOK3 pS707 |
| Protein kinase C delta type PRKCD | PRKCD pS645 |
| Protein kinase C delta type PRKCD | PRKCD pS664 |
| Protein kinase C delta type PRKCD | PRKCD pY313 |
| Protein kinase C delta type PRKCD | PRKCD seq: 208-222 + Phospho (ST) |
| Protein kinase C delta type PRKCD | PRKCD seq: 301-318 + Phospho (ST) |
| Protein kinase C delta type PRKCD | PRKCD seq: 302-318 + Phospho (ST) |
| Protein kinase C delta type PRKCD | PRKCD seq: 302-318 + Phospho (ST) |
| Protein LSM14 homolog A LSM14A | LSM14A pS216 |
| Protein LSM14 homolog A LSM14A | LSM14A seq: 182-214 + 2 Phospho (ST) |
| Protein LSM14 homolog A LSM14A | LSM14A seq: 216-229 + Phospho (ST) |
| Protein lyl-1 LYL1 | LYL1 pS260 |
| Protein lyl-1 LYL1 | LYL1 pS36 |
| Protein LYRIC MTDH | MTDH seq: 293-314 + Phospho (ST) |
| Protein NDRG1 NDRG1 | NDRG1 pT328 pS330 |
| Protein NDRG1 NDRG1 | NDRG1 seq: 362-388 + 2 Phospho (ST) |
| Protein NDRG1 NDRG1 | NDRG1 seq: 362-388 + Phospho (ST) |

TABLE 1-continued

| Phosphoprotein | Phosphorylation site |
|---|---|
| Protein NDRG1 NDRG1 | NDRG1 seq: 364-388 + Phospho (ST) |
| Protein NDRG3 NDRG3 | NDRG3 seq: 329-345 + Phospho (ST) |
| Protein numb homolog NUMB | NUMB seq: 224-263 + Phospho (ST) |
| Protein phosphatase 1 regulatory subunit 12A PPP1R12A | PPP1R12A pS299 |
| Protein phosphatase 1 regulatory subunit 12A PPP1R12A | PPP1R12A pS445 |
| Protein phosphatase 1 regulatory subunit 12A PPP1R12A | PPP1R12A seq: 442-456 + Phospho (ST) |
| Protein phosphatase 1 regulatory subunit 12A PPP1R12A | PPP1R12A seq: 443-456 + Phospho (ST) |
| Protein phosphatase 1 regulatory subunit 12C PPP1R12C | PPP1R12C pS407 |
| Protein phosphatase 1 regulatory subunit 12C PPP1R12C | PPP1R12C seq: 450-464 + Phospho (ST) |
| Protein phosphatase 1 regulatory subunit 3D PPP1R3D | PPP1R3D seq: 23-39 + Phospho (ST) |
| Protein phosphatase 1 regulatory subunit 7 PPP1R7 | PPP1R7 pS12 |
| Protein PML PML | PML pS403 |
| Protein PML PML | PML seq: 401-424 + Phospho (ST) |
| Protein polybromo-1 PBRM1 | PBRM1 seq: 7-33 + Phospho (ST) |
| Protein PRRC2A PRRC2A | PRRC2A pS383 |
| Protein RIC1 homolog KIAA1432 | KIAA1432 pS1037 |
| Protein SCAF11 SCAF11 | SCAF11 seq: 329-366 + Phospho (ST) |
| Protein scribble homolog SCRIB | SCRIB pS1448 |
| Protein SDA1 homolog SDAD1 | SDAD1 pS585 |
| Protein SET SET | SET pS7 |
| Protein transport protein Sec61 subunit alpha isoform 1 SEC61A1 | SEC61A1 pS408 |
| Protein transport protein Sec61 subunit beta SEC61B | SEC61B seq: 2-16 + Phospho (ST) |
| Protein-methionine sulfoxide oxidase MICA | MICAL1 seq: 816-835 + Phospho (ST) |
| Protein-methionine sulfoxide oxidase MICAL1 MICAL1 | MICAL1 seq: 613-637 + Oxidation (M); Phospho (ST) |
| Protein-methionine sulfoxide oxidase MICAL1 MICAL1 | MICAL1 seq: 613-637 + Phospho (ST) |
| Protein-methionine sulfoxide oxidase MICAL1 MICAL1 | MICAL1 seq: 816-835 + Phospho (ST) |
| Putative 3-phosphoinositide-dependent protein kinase 2 PDPK2 | PDPK2 pS214 |
| Putative annexin A2-like prote | ANXA2P2 pY24 |
| Putative annexin A2-like protein ANXA2P2 | ANXA2P2 pY24 |
| Putative Polycomb group protein ASXL2 ASXL2 | ASXL2 seq: 569-583 + Phospho (ST) |
| Putative RNA-binding protein 15 RBM15 | RBM15 seq: 123-132 + Phospho (ST) |
| Putative RNA-binding protein 15 RBM15 | RBM15 seq: 666-681 + 2 Phospho (ST) |
| Putative uncharacterized protein LOC100996504 | pS263 |
| Pyrin MEFV | MEFV pS179 |
| Pyrin MEFV | MEFV pS242 |
| Pyrin MEFV | MEFV seq: 177-186 + Phospho (ST) |
| Rab11 family-interacting protein 1 RAB11FIP1 | RAB11FIP1 seq: 353-379 + Phospho (ST) |
| Rab11 family-interacting protein 1 RAB11FIP1 | RAB11FIP1 seq: 498-520 + Gln->pyro-Glu (N-term Q); Phospho (ST) |
| Rab11 family-interacting protein 1 RAB11FIP1 | RAB11FIP1 seq: 498-520 + Phospho (ST) |
| Rab11 family-interacting protein | RAB11FIP5 pS176 |
| Rab11 family-interacting protein 5 RAB11FIP5 | RAB11FIP5 seq: 354-374 + Phospho (ST) |
| Rab11 family-interacting protein 5 RAB11FIP5 | RAB11FIP5 seq: 393-411 + Phospho (ST) |
| Rab3 GTPase-activating protein catalytic subunit RAB3GAP1 | RAB3GAP1 seq: 535-551 + Phospho (ST) |
| RAC-alpha serine/threonine-protein kinase AKT1 | AKT1 seq: 122-142 + Phospho (ST) |
| Ral GTPase-activating protein subunit alpha-1 RALGAPA1 | RALGAPA1 seq: 771-794 + Phospho (ST) |

TABLE 1-continued

| Phosphoprotein | Phosphorylation site |
|---|---|
| Ral GTPase-activating protein subunit alpha-2 RALGAPA2 | RALGAPA2 seq: 818-837 + Phospho (ST) |
| Ral GTPase-activating protein subunit beta RALGAPB | RALGAPB seq: 718-746 + Phospho (ST) |
| Ran-specific GTPase-activating protein RANBP1 | RANBP1 pS60 |
| Rap guanine nucleotide exchange factor 1 RAPGEF1 | RAPGEF1 pS311 |
| Ras and Rab interactor 1 RIN1 | RIN1 pS333 |
| Ras and Rab interactor 2 RIN2 | RIN2 seq: 484-491 + Phospho (ST) |
| Ras-related protein Rab-44 RAB44 | RAB44 pT188 |
| Ras-related protein Rab-7a RAB7A | RAB7A pS72 |
| Receptor expression-enhancing protein 4 REEP4 | REEP4 pS152 |
| Receptor-interacting serine/threonine-protein kinase 3 RIPK3 | RIPK3 pS410 |
| Receptor-interacting serine/threonine-protein kinase 3 RIPK3 | RIPK3 seq: 219-236 + Phospho (ST) |
| Receptor-type tyrosine-protein phosphatase epsilon PTPRE | PTPRE pY696 |
| Regulator of G-protein signaling 14 RGS14 | RGS14 pS218 |
| Regulatory-associated protein of mTOR RPTOR | RPTOR seq: 850-867 + Phospho (ST) |
| Remodeling and spacing factor 1 RSF1 | RSF1 pS748 |
| Reticulon-4 RTN4 | RTN4 seq: 178-201 + Phospho (ST) |
| Retinoic acid receptor RXR-alpha RXRA | RXRA seq: 5-25 + Phospho (ST) |
| Rho GTPase-activating protein 12 ARHGAP12 | ARHGAP12 seq: 229-250 + 2 Phospho (ST) |
| Rho GTPase-activating protein 15 ARHGAP15 | ARHGAP15 pS43 |
| Rho GTPase-activating protein 17 ARHGAP17 | ARHGAP17 seq: 161-172 + Phospho (ST) |
| Rho GTPase-activating protein 9 ARHGAP9 | ARHGAP9 seq: 279-298 + Phospho (ST) |
| Rho guanine nucleotide exchange factor 11 ARHGEF11 | ARHGEF11 seq: 1452-1473 + Phospho (ST) |
| Rho guanine nucleotide exchange factor 2 ARHGEF2 | ARHGEF2 pS174 |
| Rho guanine nucleotide exchange factor 2 ARHGEF2 | ARHGEF2 pT679 |
| Rho guanine nucleotide exchange factor 2 ARHGEF2 | ARHGEF2 seq: 118-131 + Phospho (ST) |
| Rho guanine nucleotide exchange factor 2 ARHGEF2 | ARHGEF2 seq: 132-138 + Phospho (ST) |
| Rho guanine nucleotide exchange factor 2 ARHGEF2 | ARHGEF2 seq: 140-148 + Phospho (ST) |
| Rho guanine nucleotide exchange factor 2 ARHGEF2 | ARHGEF2 seq: 149-168 + Phospho (ST) |
| Rho guanine nucleotide exchange factor 6 ARHGEF6 | ARHGEF6 seq: 122-148 + Phospho (ST) |
| Rho guanine nucleotide exchange factor 7 ARHGEF7 | ARHGEF7 pS518 |
| Ribosomal biogenesis protein LAS1L LAS1L | LAS1L pS617 |
| Ribosomal L1 domain-containing protein 1 RSL1D1 | RSL1D1 pS361 |
| Ribosomal L1 domain-containing protein 1 RSL1D1 | RSL1D1 seq: 357-373 + Phospho (ST) |
| Ribosomal protein S6 kinase alpha-1 RPS6KA1 | RPS6KA1 pS380 |
| Ribosomal protein S6 kinase alpha-3 RPS6KA3 | RPS6KA3 pS369 |
| Ribosomal protein S6 kinase alpha-4 RPS6KA4 | RPS6KA4 pS678 |
| Ribosomal protein S6 kinase alpha-4 RPS6KA4 | RPS6KA4 seq: 681-699 + 2 Phospho (ST) |
| Ribosomal RNA processing protein 1 homolog B RRP1B | RRP1B seq: 443-472 + Phospho (ST) |
| RNA binding motif protein, X-linked-like-1 RBMXL1 | RBMXL1 pS208 |
| RNA polymerase II subunit A C-terminal domain phosphatase CTDP1 | CTDP1 seq: 405-434 + Phospho (ST) |
| RNA polymerase II-associated protein 3 RPAP3 | RPAP3 pS481 |
| RNA polymerase II-associated protein 3 RPAP3 | RPAP3 seq: 478-493 + Phospho (ST) |
| RNA polymerase-associated protein CTR9 homolog CTR9 | CTR9 pT925 |
| RNA polymerase-associated protein LEO1 LEO1 | LEO1 seq: 543-548 + Phospho (ST) |
| RNA-binding protein 14 RBM14 | RBM14 pS256 |
| RNA-binding protein 14 RBM14 | RBM14 pS278 |
| RNA-binding protein 14 RBM14 | RBM14 pS620 |

TABLE 1-continued

| Phosphoprotein | Phosphorylation site |
|---|---|
| RNA-binding protein 14 RBM14 | RBM14 pT206 |
| RNA-binding protein 14 RBM14 | RBM14 seq: 518-541 + Phospho (ST) |
| RNA-binding protein 39 RBM39 | RBM39 pS136 |
| RNA-binding protein Raly RALY | RALY pT84 |
| RRP12-like protein RRP12 | RRP12 pS66 |
| SAM and SH3 domain-containing protein 3 SASH3 | SASH3 pS243 |
| SAM and SH3 domain-containing protein 3 SASH3 | SASH3 seq: 34-67 + 2 Phospho (ST) |
| SAM and SH3 domain-containing protein 3 SASH3 | SASH3 seq: 34-67 + Phospho (ST) |
| SAM domain-containing protein SAMSN-1 SAMSN1 | SAMSN1 pS23 |
| SAM domain-containing protein SAMSN-1 SAMSN1 | SAMSN1 seq: 122-149 + Phospho (ST) |
| SAM domain-containing protein SAMSN-1 SAMSN1 | SAMSN1 seq: 20-29 + Phospho (ST) |
| SAP domain-containing ribonucleoprotein SARNP | SARNP pS163 |
| Scaffold attachment factor B1 SAFB | SAFB pS601 pS604 |
| Scaffold attachment factor B1 SAFB | SAFB pS604 |
| Scaffold attachment factor B2 SAFB2 | SAFB2 seq: 226-252 + Phospho (ST) |
| Secretory carrier-associated membrane protein 2 SCAMP2 | SCAMP2 seq: 317-329 + Phospho (ST) |
| Sentan SNTN | SNTN seq: 37-42 + Phospho (ST) |
| Septin-2 SEPT2 | SEPT2 pS218 |
| Serine/arginine repetitive matrix protein 1 SRRM1 | SRRM1 pS769 |
| Serine/arginine repetitive matrix protein 1 SRRM1 | SRRM1 pS769 pS773 pS781 |
| Serine/arginine repetitive matrix protein 1 SRRM1 | SRRM1 pT220 |
| Serine/arginine repetitive matrix protein 1 SRRM1 | SRRM1 seq: 711-722 + 2 Phospho (ST) |
| Serine/arginine repetitive matrix protein 1 SRRM1 | SRRM1 seq: 763-788 + 2 Phospho (ST) |
| Serine/arginine repetitive matrix protein 2 SRRM2 | SRRM2 pS2100 pS2102 pT2104 |
| Serine/arginine repetitive matrix protein 2 SRRM2 | SRRM2 pS295 pS297 |
| Serine/arginine repetitive matrix protein 2 SRRM2 | SRRM2 pS876 |
| Serine/arginine repetitive matrix protein 2 SRRM2 | SRRM2 pS994 |
| Serine/arginine repetitive matrix protein 2 SRRM2 | SRRM2 pT2289 |
| Serine/arginine repetitive matrix protein 2 SRRM2 | SRRM2 seq: 1527-1536 + Phospho (ST) |
| Serine/arginine repetitive matrix protein 2 SRRM2 | SRRM2 seq: 852-870 + 2 Phospho (ST) |
| Serine/arginine-rich splicing factor 1 SRSF1 | SRSF1 pS199 pS201 |
| Serine/arginine-rich splicing factor 9 SRSF9 | SRSF9 pS211 |
| Serine/arginine-rich splicing factor 9 SRSF9 | SRSF9 seq: 210-221 + Phospho (Y) |
| Serine/threonine-protein kinase 10 STK10 | STK10 seq: 20-27 + Phospho (ST) |
| Serine/threonine-protein kinase 10 STK10 | STK10 seq: 447-464 + 2 Phospho (ST) |
| Serine/threonine-protein kinase 10 STK10 | STK10 seq: 447-464 + Phospho (ST) |
| Serine/threonine-protein kinase 10 STK10 | STK10 seq: 9-17 + Phospho (ST) |
| Serine/threonine-protein kinase 10 STK10 | STK10 seq: 9-17 + Phospho (ST) |
| Serine/threonine-protein kinase 11-interacting protein STK11IP | STK11IP pS772 |
| Serine/threonine-protein kinase 4 STK4 | STK4 pT177 |
| Serine/threonine-protein kinase D2 PRKD2 | PRKD2 seq: 710-730 + Phospho (Y) |
| Serine/threonine-protein kinase LATS1 LATS1 | LATS1 pS464 |
| Serine/threonine-protein kinase MARK2 MARK2 | MARK2 pS535 |
| Serine/threonine-protein kinase N1 PKN1 | PKN1 seq: 379-396 + Phospho (ST) |
| Serine/threonine-protein kinase Nek9 NEK9 | NEK9 seq: 10-39 + Phospho (ST) |
| Serine/threonine-protein kinase Nek9 NEK9 | NEK9 seq: 735-779 + Phospho (ST) |
| Serine/threonine-protein kinase PAK 1 PAK1 | PAK1 pS144 |
| Serine/threonine-protein kinase PAK 1 PAK1 | PAK1 seq: 204-237 + 2 Phospho (ST) |
| Serine/threonine-protein kinase PAK 1 PAK1 | PAK1 seq: 216-237 + Phospho (ST) |
| Serine/threonine-protein kinase PAK 2 PAK2 | PAK2 pS141 |

TABLE 1-continued

| Phosphoprotein | Phosphorylation site |
|---|---|
| Serine/threonine-protein kinase PAK 2 PAK2 | PAK2 seq: 139-160 + Phospho (ST) |
| Serine/threonine-protein kinase PAK 2 PAK2 | PAK2 seq: 53-62 + Phospho (ST) |
| Serine/threonine-protein kinase SIK3 SIK3 | SIK3 pS808 |
| Serine/threonine-protein kinase WNK1 WNK1 | WNK1 seq: 1996-2021 + Phospho (ST) |
| Serine/threonine-protein phosphatase 2B catalytic subunit beta isoform PPP3CB | PPP3CB pS471 |
| Serologically defined colon cancer antigen 3 SDCCAG3 | SDCCAG3 pS247 |
| SH3 domain-binding protein 1 SH3BP1 | SH3BP1 pS262 |
| SH3 domain-binding protein 1 SH3BP1 | SH3BP1 pS544 |
| SH3 domain-binding protein 1 SH3BP1 | SH3BP1 pS613 |
| SH3 domain-binding protein 1 SH3BP1 | SH3BP1 seq: 608-615 + Phospho (ST) |
| SH3 domain-binding protein 5-like SH3BP5L | SH3BP5L pS343 pS350 |
| SH3 domain-containing kinase-binding protein 1 SH3KBP1 | SH3KBP1 pS108 |
| SH3 domain-containing kinase-binding protein 1 SH3KBP1 | SH3KBP1 pS230 |
| SH3 domain-containing kinase-binding protein 1 SH3KBP1 | SH3KBP1 pS410 |
| SHC-transforming protein 1 SHC1 | SHC1 pS139 |
| SHC-transforming protein 1 SHC1 | SHC1 seq: 420-435 + Phospho (Y) |
| Shootin- | KIAA1598 seq: 485-505 + Phospho (ST) |
| Shootin-1 KIAA1598 | KIAA1598 pS506 |
| Sialic acid-binding Ig-like lectin 7 SIGLEC7 | SIGLEC7 seq: 403-420 + Phospho (ST) |
| Sialomucin core protein 24 CD164 | CD164 seq: 1-6 + Phospho (ST) |
| Signal transducer and activator of transcription 3 STAT3 | STAT3 pS691 |
| Signal transducer and activator of transcription 5B STAT5B | STAT5B seq: 122-140 + Phospho (ST) |
| Signal-induced proliferation-associated protein 1 SIPA1 | SIPA1 pS74 |
| Small acidic protein SMAP | SMAP pS17 |
| Small acidic protein SMAP | SMAP pS93 |
| Small acidic protein SMAP | SMAP seq: 15-37 + Phospho (ST) |
| Small acidic protein SMAP | SMAP seq: 15-38 + Phospho (ST) |
| Smith-Magenis syndrome chromosomal region candidate gene 8 protein SMCR8 | SMCR8 pS417 |
| Smoothelin SMTN | SMTN seq: 30-35 + Phospho (ST) |
| Sodium/hydrogen exchanger 1 SLC9A1 | SLC9A1 pS703 |
| Something about silencing protein 10 UTP3 | UTP3 seq: 20-55 + Phospho (ST) |
| Sorting nexin-17 SNX17 | SNX17 pS437 pS440 |
| Sorting nexin-18 SNX18 | SNX18 seq: 193-198 + Phospho (ST) |
| Sorting nexin-2 SNX2 | SNX2 pS119 |
| Sorting nexin-27 SNX27 | SNX27 pS51 |
| Spectrin beta chain, non-erythrocytic 1 SPTBN1 | SPTBN1 seq: 2159-2174 + Phospho (ST) |
| Spermatogenesis-defective protein 39 homolog VIPAS39 | VIPAS39 seq: 117-135 + Phospho (ST) |
| Splicing factor 3A subunit 3 SF3A3 | SF3A3 pS295 |
| Splicing factor, arginine/serine-rich 19 SCAF1 | SCAF1 pS498 pS500 |
| Splicing factor, arginine/serine-rich 19 SCAF1 | SCAF1 pS874 |
| Src kinase-associated phosphoprotein 2 SKAP2 | SKAP2 pS6 |
| Src kinase-associated phosphoprotein 2 SKAP2 | SKAP2 seq: 2-18 + 2 Phospho (ST) |
| Src-like-adapter SLA | SLA pS190 |
| Stathmin STMN1 | STMN1 pS16 |
| Stathmin STMN1 | STMN1 pS16 pS25 |
| Stathmin STMN1 | STMN1 pS25 |
| Stimulator of interferon genes protein TMEM173 | TMEM173 seq: 348-375 + Phospho (ST) |
| Stromal membrane-associated protein 2 SMAP2 | SMAP2 seq: 227-254 + Oxidation (M); Phospho (ST) |
| Stromal membrane-associated protein 2 SMAP2 | SMAP2 seq: 227-254 + Phospho (ST) |

TABLE 1-continued

| Phosphoprotein | Phosphorylation site |
|---|---|
| Structural maintenance of chromosomes protein 3 SMC3 | SMC3 seq: 1080-1099 + Phospho (ST) |
| Sulfotransferase 1A4 SULT1A4 | SULT1A4 pS288 |
| SUMO-activating enzyme subunit 2 UBA2 | UBA2 seq: 277-308 + Phospho (ST) |
| SWI/SNF complex subunit SMARCC1 SMARCC1 | SMARCC1 pS328 pS330 |
| SWI/SNF complex subunit SMARCC1 SMARCC1 | SMARCC1 seq: 326-340 + Phospho (ST) |
| SWI/SNF complex subunit SMARCC2 SMARCC2 | SMARCC2 pS302 pS304 |
| SWI/SNF complex subunit SMARCC2 SMARCC2 | SMARCC2 pS347 |
| SWI/SNF-related matrix-associated actin-dependent regulator of chromatin subfamily A-like protein 1 SMARCAL1 | SMARCAL1 pS112 |
| Synaptojanin-1 SYNJ1 | SYNJ1 pS1049 pS1053 |
| Synaptotagmin-like protein 2 SYTL2 | SYTL2 pT711 |
| Synergin gamma SYNRG | SYNRG seq: 467-485 + Phospho (ST) |
| Synergin gamma SYNRG | SYNRG seq: 750-771 + Gln->pyro-Glu (N-term Q); Phospho (ST) |
| Syntaxin-7 STX7 | STX7 seq: 124-138 + Phospho (ST) |
| TAR DNA-binding protein 43 TARDBP | TARDBP pS292 |
| Target of EGR1 protein 1 TOE1 | TOE1 seq: 418-439 + Phospho (ST) |
| Target of Myb protein 1 TOM1 | TOM1 seq: 453-478 + Phospho (ST) |
| TATA-binding protein-associated factor 2N TAF15 | TAF15 pS97 |
| TBC1 domain family member 1 TBC1D1 | TBC1D1 pS627 |
| TBC1 domain family member 1 TBC1D1 | TBC1D1 seq: 562-591 + Phospho (ST) |
| TBC1 domain family member 22A TBC1D22A | TBC1D22A seq: 143-164 + Phospho (ST) |
| TBC1 domain family member 22A TBC1D22A | TBC1D22A seq: 165-193 + Phospho (ST) |
| TBC1 domain family member 5 TBC1D5 | TBC1D5 pS522 |
| TBC1 domain family member 5 TBC1D5 | TBC1D5 pS539 |
| TBC1 domain family member 5 TBC1D5 | TBC1D5 pS554 |
| TBC1 domain family member 5 TBC1D5 | TBC1D5 pS730 |
| TBC1 domain family member 8 TBC1D8 | TBC1D8 seq: 445-468 + Phospho (ST) |
| TBC1 domain family member 9B TBC1D9B | TBC1D9B pS275 |
| TCF3 fusion partner TFPT | TFPT pS180 |
| Telomerase Cajal body protein 1 WRAP53 | WRAP53 pS54 |
| Telomerase protein component 1 TEP1 | TEP1 pS397 |
| Tensin-3 TNS3 | TNS3 pS776 |
| Tensin-3 TNS3 | TNS3 seq: 330-356 + Phospho (ST) |
| Tensin-3 TNS3 | TNS3 seq: 361-401 + Phospho (ST) |
| Tensin-3 TNS3 | TNS3 seq: 646-663 + Phospho (ST) |
| Tensin-3 TNS3 | TNS3 seq: 646-663 + Phospho (ST) |
| Tensin-3 TNS3 | TNS3 seq: 669-704 + Phospho (ST) |
| Tether containing UBX domain for GLUT4 ASPSCR1 | ASPSCR1 pS500 |
| Tetratricopeptide repeat protein 7A TTC7A | TTC7A pS182 |
| Tetratricopeptide repeat protein 7A TTC7A | TTC7A seq: 49-66 + Phospho (ST) |
| TGF-beta receptor type-2 TGFBR2 | TGFBR2 seq: 350-356 + Phospho (ST) |
| THO complex subunit 1 THOC1 | THOC1 seq: 2-14 + Phospho (ST) |
| Thromboxane A2 receptor TBXA2R | TBXA2R pS331 |
| Thyroid hormone receptor-associated protein 3 THRAP3 | THRAP3 pS377 |
| Thyroid hormone receptor-associated protein 3 THRAP3 | THRAP3 pS379 |
| Thyroid hormone receptor-associated protein 3 THRAP3 | THRAP3 seq: 559-565 + Phospho (ST) |
| Torsin-1A-interacting protein 1 TOR1AIP1 | TOR1AIP1 seq: 252-274 + Phospho (ST) |
| Torsin-4A TOR4A | TOR4A seq: 99-107 + Phospho (ST) |
| TRAF family member-associated NF-kappa-B activator TANK | TANK pS208 |

TABLE 1-continued

| Phosphoprotein | Phosphorylation site |
| --- | --- |
| TRAF2 and NCK-interacting protein kinase TNIK | TNIK pS640 |
| Transcription activator BRG1 SMARCA4 | SMARCA4 pS1452 |
| Transcription elongation factor A protein 1 TCEA1 | TCEA1 pS100 |
| Transcription factor 12 TCF12 | TCF12 seq: 75-90 + Phospho (Y) |
| Transcription factor E2-alpha TCF3 | TCF3 pS379 |
| Transcription factor E3 TFE3 | TFE3 pS548 |
| Transcription factor SPT20 homolog SUPT20H | SUPT20H seq: 507-531 + Phospho (ST) |
| Transcription intermediary factor 1-alpha TRIM24 | TRIM24 pS811 |
| Transcription intermediary factor 1-beta TRIM28 | TRIM28 seq: 747-767 + Phospho (Y) |
| Transcriptional regulator ATRX ATRX | ATRX pS1527 |
| Transcriptional repressor p66-alpha GATAD2A | GATAD2A pS100 pS114 |
| Transcriptional repressor p66-beta GATAD2B | GATAD2B pT120 pS122 |
| Transformer-2 protein homolog alpha TRA2A | TRA2A pS260 pS262 |
| Transformer-2 protein homolog beta TRA2B | TRA2B seq: 198-217 + 2 Phospho (ST) |
| Transgelin-2 TAGLN2 | TAGLN2 pS163 |
| Transgelin-3 TAGLN3 | TAGLN3 pS185 |
| Transmembrane protein 132A TMEM132A | TMEM132A seq: 482-487 + Phospho (ST) |
| Transmembrane protein 201 TMEM201 | TMEM201 pS454 |
| Transmembrane protein C16orf54 C16orf54 | C16orf54 pS194 |
| Treacle protein TCOF1 | TCOF1 pS1350 |
| Treacle protein TCOF1 | TCOF1 pS1378 |
| Treacle protein TCOF1 | TCOF1 pS381 |
| Tristetraprolin ZFP36 | ZFP36 pS60 |
| Tubulin-folding cofactor B TBCB | TBCB pS110 |
| Tumor necrosis factor alpha-induced protein 3 TNFAIP3 | TNFAIP3 pS220 |
| Tumor suppressor p53-binding protein 1 TP53BP1 | TP53BP1 pS1362 |
| Tumor suppressor p53-binding protein 1 TP53BP1 | TP53BP1 pS265 |
| Tumor suppressor p53-binding protein 1 TP53BP1 | TP53BP1 pS727 |
| Tumor suppressor p53-binding protein 1 TP53BP1 | TP53BP1 seq: 1459-1490 + Phospho (ST) |
| Tumor suppressor p53-binding protein 1 TP53BP1 | TP53BP1 seq: 1460-1490 + Phospho (ST) |
| Tumor suppressor p53-binding protein 1 TP53BP1 | TP53BP1 seq: 372-387 + Phospho (ST) |
| Tumor suppressor p53-binding protein 1 TP53BP1 | TP53BP1 seq: 528-558 + Phospho (ST) |
| Type 2 phosphatidylinositol 4,5-bisphosphate 4-phosphatase TMEM55A | TMEM55A seq: 10-35 + Phospho (ST) |
| Type-1 angiotensin II receptor-associated protein AGTRAP | AGTRAP seq: 131-152 + Phospho (ST) |
| Tyrosine-protein kinase ABL1 ABL1 | ABL1 seq: 716-727 + Phospho (ST) |
| Tyrosine-protein kinase Fes/Fps FES | FES pY713 |
| Tyrosine-protein kinase Fgr FGR | FGR pY412 |
| Tyrosine-protein kinase HCK HCK | HCK pT36 |
| Tyrosine-protein kinase SYK SYK | SYK pS295 pS297 |
| Tyrosine-protein kinase SYK SYK | SYK pS297 |
| Tyrosine-protein phosphatase non-receptor type 11 PTPN11 | PTPN11 pY584 |
| Tyrosine-protein phosphatase non-receptor type 12 PTPN12 | PTPN12 pS435 |
| Tyrosine-protein phosphatase non-receptor type 2 PTPN2 | PTPN2 seq: 291-307 + Phospho (ST) |
| Tyrosine-protein phosphatase non-receptor type 6 PTPN6 | PTPN6 pS10 |
| Tyrosine-protein phosphatase non-receptor type 6 PTPN6 | PTPN6 pY536 |
| Tyrosine-protein phosphatase non-receptor type 7 PTPN7 | PTPN7 pS143 |
| Tyrosine-protein phosphatase non-receptor type 7 PTPN7 | PTPN7 pS44 |
| U2 small nuclear ribonucleoprotein A' SNRPA1 | SNRPA1 seq: 178-191 + Phospho (ST) |
| U2 small nuclear ribonucleoprotein A' SNRPA1 | SNRPA1 seq: 178-192 + Phospho (ST) |
| U4/U6 small nuclear ribonucleoprotein Prp31 PRPF31 | PRPF31 pS439 pT440 |
| Ubiquitin carboxyl-terminal hydrolase 14 USP14 | USP14 pS143 |
| Ubiquitin carboxyl-terminal hydrolase 20 USP20 | USP20 seq: 121-142 + Phospho (ST) |
| Ubiquitin carboxyl-terminal hydrolase 24 USP24 | USP24 seq: 1370-1395 + Phospho (ST) |

TABLE 1-continued

| Phosphoprotein | Phosphorylation site |
| --- | --- |
| Ubiquitin-associated protein 2-like UBAP2L | UBAP2L seq: 601-612 + Phospho (ST) |
| Ubiquitin-conjugating enzyme E2 variant 1 UBE2V1 | UBE2V1 pS146 |
| Ubiquitin-like modifier-activating enzyme 1 UBA1 | UBA1 pS820 |
| UBX domain-containing protein 1 UBXN1 | UBXN1 seq: 178-209 + Phospho (ST) |
| Uncharacterized protein C12orf43 C12orf43 | C12orf43 seq: 163-185 + Phospho (ST) |
| Uncharacterized protein C7orf43 C7orf43 | C7orf43 pS517 |
| Uncharacterized protein C7orf43 C7orf43 | C7orf43 seq: 515-525 + Phospho (ST) |
| Uncharacterized protein C9orf142 C9orf142 | C9orf142 pT145 |
| Uncharacterized protein KIAA0930 KIAA0930 | KIAA0930 pS306 |
| Uncharacterized protein KIAA0930 KIAA0930 | KIAA0930 pS362 |
| Uncharacterized protein KIAA0930 KIAA0930 | KIAA0930 seq: 261-284 + Phospho (ST) |
| Uncharacterized protein KIAA0930 KIAA0930 | KIAA0930 seq: 285-296 + Phospho (ST) |
| Uncharacterized protein KIAA1143 KIAA1143 | KIAA1143 pS50 |
| Unconventional myosin-IXb MYO9B | MYO9B pT1271 |
| Unconventional myosin-IXb MYO9B | MYO9B seq: 712-729 + Phospho (ST) |
| Unconventional myosin-Va MYO5A | MYO5A seq: 1650-1666 + Phospho (ST) |
| Unconventional myosin-XVIIIa MYO18A | MYO18A pS2020 |
| Unconventional myosin-XVIIIa MYO18A | MYO18A pS2043 |
| Unconventional myosin-XVIIIa MYO18A | MYO18A seq: 2035-2048 + Phospho (ST) |
| UPF0688 protein C1orf174 C1orf174 | C1orf174 pS189 |
| Vasodilator-stimulated phosphoprotein VASP | VASP seq: 308-319 + Phospho (ST) |
| Vasodilator-stimulated phosphoprotein VASP | VASP seq: 320-346 + Oxidation (M); Phospho (ST) |
| Vasodilator-stimulated phosphoprotein VASP | VASP seq: 320-346 + Phospho (ST) |
| Vasodilator-stimulated phosphoprotein VASP | VASP seq: 322-346 + Phospho (ST) |
| Viment | VIM seq: 322-342 + Gln->pyro-Glu (N-term Q); Phospho (ST) |
| Vimentin VIM | VIM pS325 |
| Vimentin VIM | VIM pS34 |
| Vimentin VIM | VIM pS39 |
| Vimentin VIM | VIM pS419 |
| Vimentin VIM | VIM pS420 |
| Vimentin VIM | VIM pS430 |
| Vimentin VIM | VIM pS49 |
| Vimentin VIM | VIM pS51 |
| Vimentin VIM | VIM pT426 |
| Vimentin VIM | VIM seq: 14-28 + 2 Phospho (ST) |
| Vimentin VIM | VIM seq: 14-28 + Oxidation (M); Phospho (ST) |
| Vimentin VIM | VIM seq: 14-28 + Phospho (ST) |
| Vimentin VIM | VIM seq: 322-342 + Gln->pyro-Glu (N-term Q); Phospho (ST) |
| Vimentin VIM | VIM seq: 37-50 + 2 Phospho (ST) |
| Vimentin VIM | VIM seq: 425-439 + Phospho (ST) |
| Vimentin VIM | VIM seq: 51-64 + Phospho (Y) |
| WAS/WASL-interacting protein family member 1 WIPF1 | WIPF1 pS234 |
| WAS/WASL-interacting protein family member 1 WIPF1 | WIPF1 pS340 |
| WASH complex subunit FAM21B FAM21B | FAM21B pS264 |
| WASH complex subunit FAM21C FAM21C | FAM21C pS288 |
| WD repeat and FYVE domain-containing protein 3 WDFY3 | WDFY3 pS2278 |
| WD repeat-containing protein 7 WDR7 | WDR7 seq: 1152-1173 + Phospho (ST) |
| X-ray repair cross-complementing protein 5 XRCC5 | XRCC5 seq: 569-599 + Phospho (ST) |

TABLE 1-continued

| Phosphoprotein | Phosphorylation site |
|---|---|
| X-ray repair cross-complementing protein 6 XRCC6 | XRCC6 seq: 475-488 + Phospho (ST) |
| YLP motif-containing protein 1 YLPM1 | YLPM1 seq: 887-895 + Phospho (ST) |
| Zinc finger CCCH domain-containing protein 13 ZC3H13 | ZC3H13 pS242 |
| Zinc finger CCCH domain-containing protein 13 ZC3H13 | ZC3H13 pS877 |
| Zinc finger CCCH domain-containing protein 13 ZC3H13 | ZC3H13 pT263 pS265 |
| Zinc finger CCCH domain-containing protein 14 ZC3H14 | ZC3H14 seq: 387-404 + Phospho (ST) |
| Zinc finger CCHC domain-containing protein 8 ZCCHC8 | ZCCHC8 pS658 |
| Zinc finger CCHC domain-containing protein 8 ZCCHC8 | ZCCHC8 seq: 590-609 + Phospho (ST) |
| Zinc finger protein 185 ZNF185 | ZNF185 seq: 463-482 + Phospho (ST) |
| Zinc finger protein 609 ZNF609 | ZNF609 seq: 571-582 + Phospho (ST) |
| Zinc finger protein ubi-d4 DPF2 | DPF2 pS142 |
| Zinc finger protein with KRAB and SCAN domains 8 ZKSCAN8 | ZKSCAN8 seq: 7-26 + Phospho (ST) |
| Zinc finger Ran-binding domain-containing protein 2 ZRANB2 | ZRANB2 pS120 |
| Zinc finger SWIM domain-containing protein 1 ZSWIM1 | ZSWIM1 seq: 465-470 + Phospho (ST) |
| Zyxin ZYX | ZYX pS281 |
| Zyxin ZYX | ZYX seq: 296-320 + Phospho (ST) |

Suitably, the panel of phosphorylation sites may include any one, two, three, four, five, six, seven, eight, nine, ten or more than ten of the phosphorylation sites set out in Table 2 below.

TABLE 2

| Phosphoprotein | Phosphopeptide |
|---|---|
| Dedicator of cytokinesis protein 10 | DOCK10 pS1295 |
| Neutrophil cytosol factor 1 | NCF1 pS348 |
| Protein-methionine sulfoxide oxidase MICAL1 | MICAL1 seq: 816-835 + Phospho (ST) |
| Serine/threonine-protein kinase PAK 1 | PAK1 seq: 204-237 + 2 Phospho (ST) |
| Inactive rhomboid protein 2 | RHBDF2 seq: 88-95 + Phospho (ST) |
| Protein-methionine sulfoxide oxidase MICAL1 | MICAL1 seq: 613-637 + Oxidation (M); Phospho (ST) |
| Niban-like protein 1 | FAM129B pS665 |
| Deoxynucleoside triphosphate triphosphohydrolase SAMHD1 | SAMHD1 pS102 |
| Deoxynucleoside triphosphate triphosphohydrolase SAMHD1 | SAMHD1 seq: 15-43 + 2 Phospho (ST) |
| NAD kinase | NADK pS46 |
| BTB/POZ domain-containing protein KCTD12 | KCTD12 seq: 185-206 + Phospho (ST) |
| Torsin-1A-interacting protein 1 | TOR1AIP1 seq: 252-274 + Phospho (ST) |
| Plectin | PLEC pS4384 pS4400 |
| Microtubule-associated serine/threonine-protein kinase 3 | MAST3 seq: 707-725 + Phospho (ST) |
| NAD kinase | NADK pS46 |
| Apolipoprotein B receptor | APOBR seq: 1004-1009 + 2 Phospho (ST) |
| WD repeat-containing protein 7 | WDR7 seq: 1152-1173 + Phospho (ST) |
| Telomerase protein component 1 | TEP1 pS397 |
| Neuroblast differentiation-associated protein AHNAK | AHNAK pS4520 |
| Cation-independent mannose-6-phosphate receptor | IGF2R seq: 2398-2420 + Phospho (ST) |
| Vimentin | VIM pS325 |
| Actin-related protein 2/3 complex subunit 1B | ARPC1B seq: 309-326 + Phospho (ST) |

TABLE 2-continued

| Phosphoprotein | Phosphopeptide |
|---|---|
| Protein-methionine sulfoxide oxidase MICAL1 | MICAL1 seq: 613-637 + Phospho (ST) |
| A-kinase anchor protein 13 | AKAP13 seq: 647-681 + Phospho (ST) |
| 28 kDa heat- and acid-stable phosphoprotein | PDAP1 pS178 |
| Mitogen-activated protein kinase kinase kinase 3 | MAP3K3 seq: 144-161 + Phospho (ST) |
| Vimentin | VIM pS325 |
| Serine/threonine-protein kinase N1 | PKN1 seq: 379-396 + Phospho (ST) |
| Neuroblast differentiation-associated protein AHNAK | AHNAK pT4430 |
| Protein EVI2B | EVI2B seq: 266-279 + 2 Phospho (ST) |
| Protein EVI2B | EVI2B pS294 |
| Minor histocompatibility protein HA-1 | HMHA1 seq: 619-641 + Phospho (ST) |
| Coiled-coil domain-containing protein 88B | CCDC88B pS1408 |
| Coiled-coil domain-containing protein 88B | CCDC88B pS1379 |
| Tyrosine-protein kinase SYK | SYK pS297 |
| A-kinase anchor protein 13 | AKAP13 seq: 647-681 + Phospho (ST) |
| Calmodulin-regulated spectrin-associated protein 1 | CAMSAP 1 pS629 |
| Dedicator of cytokinesis protein 10 | DOCK10 pT196 |
| DENN domain-containing protein 1A | DENND1A seq: 518-531 + 2 Phospho (ST) |
| Mitogen-activated protein kinase kinase kinase 3 | MAP3K3 seq: 164-185 + 2 Phospho (ST) |
| Niban-like protein 1 | FAM129B seq: 686-705 + Phospho (ST) |
| Minor histocompatibility protein HA-1 | HMHA1 pS619 |
| E3 ubiquitin-protein ligase TRIP12 | TRIP12 pS1577 |
| Oxysterol-binding protein-related protein 11 | OSBPL11 pS172 |
| COP9 signalosome complex subunit 7a | COPS7A seq: 222-243 + Phospho (ST) |
| Vimentin | VIM pS39 |
| Ribosomal protein S6 kinase alpha-1 | RPS6KA1 pS380 |
| Dedicator of cytokinesis protein 10 | DOCK10 pT1406 |
| EH domain-binding protein 1-like protein 1 | EHBP1L1 pS1257 |
| Coronin-7 | CORO7 pS465 |
| Drebrin-like protein | DBNL pS141 |
| Uncharacterized protein KIAA0930 | KIAA0930 seq: 285-296 + Phospho (ST) |
| NAD kinase | NADK seq: 44-57 + Phospho (ST) |
| PDZ and LIM domain protein 2 | PDLIM2 pS197 |
| Protein EVI2B | EVI2B seq: 266-279 + 2 Phospho (ST) |
| SH3 domain-containing kinase-binding protein 1 | SH3KBP1 pS230 |
| Transgelin-3 | TAGLN3 pS185 |
| EH domain-binding protein 1-like protein 1 | EHBP1L1 seq: 1270-1278 + Phospho (ST) |
| Protein FAM65B | FAM65B pS21 |
| Protein phosphatase 1 regulatory subunit 12A | PPP1R12A pS445 |
| Neuroblast differentiation-associated protein AHNAK | AHNAK pT4766 |
| Bridging integrator 2 | BIN2 seq: 450-477 + 2 Phospho (ST) |
| Neurobeachin-like protein 2 | NBEAL2 pS2739 |
| Hematopoietic lineage cell-specific protein | HCLS1 pT308 |
| Platelet receptor Gi24 | C10orf54 pS235 |
| Bridging integrator 2 | BIN2 seq: 450-477 + 2 Phospho (ST) |
| Neuroblast differentiation-associated protein AHNAK | AHNAK pS3426 |
| Drebrin-like protein | DBNL pS269 |
| Vimentin | VIM pS325 |
| Phosphoglycerate mutase 1 | PGAM1 pS14 |
| Serine/threonine-protein kinase PAK 2 | PAK2 seq: 53-62 + Phospho (ST) |
| Arf-GAP with Rho-GAP domain, ANK repeat and PH domain-containing protein 1 | ARAP1 seq: 222-244 + Phospho (Y) |
| Arf-GAP with Rho-GAP domain, ANK repeat and PH domain-containing protein 1 | ARAP1 seq: 222-244 + Phospho (ST) |
| Dedicator of cytokinesis protein 10 | DOCK10 pT1440 |
| Probable phosphoglycerate mutase 4 | PGAM4 seq: 118-138 + Phospho (ST) |
| Platelet receptor Gi24 | C10orf54 pS235 |
| Bridging integrator 2 | BIN2 seq: 461-477 + Phospho (ST) |
| Receptor-interacting serine/threonine-protein kinase 3 | RIPK3 pS410 |
| Cytohesin-4 | CYTH4 pS215 |
| Neuroblast differentiation-associated protein AHNAK | AHNAK pT4766 |
| Ras and Rab interactor 1 | RIN1 pS333 |

TABLE 2-continued

| Phosphoprotein | Phosphopeptide |
|---|---|
| Lysosomal-trafficking regulator | LYST pS2149 |
| Transcription factor SPT20 homolog | SUPT20H seq: 507-531 + Phospho (ST) |
| Lysosomal-trafficking regulator | LYST pS2105 |
| Brain-specific angiogenesis inhibitor 1-associated protein 2 | BAIAP2 pS366 |
| Serine/threonine-protein phosphatase 2B catalytic subunit beta isoform | PPP3CB pS471 |
| Tensin-3 | TNS3 seq: 361-401 + Phospho (ST) |
| Plectin | PLEC seq: 4384-4401 + Phospho (ST) |
| GEM-interacting protein | GMIP seq: 231-248 + Phospho (ST) |
| Bridging integrator 2 | BIN2 seq: 461-477 + Phospho (ST) |
| Coiled-coil domain-containing protein 88B | CCDC88B seq: 595-613 + Phospho (ST) |
| Coiled-coil domain-containing protein 88B | CCDC88B seq: 429-454 + Phospho (ST) |
| Band 4.1-like protein 3 | EPB41L3 pS962 |
| Tetratricopeptide repeat protein 7A | TTC7A seq: 49-66 + Phospho (ST) |
| G-protein-signaling modulator 3 | GPSM3 pS39 |
| Mitogen-activated protein kinase kinase kinase 2 | MAP3K2 pS153 |
| Lamin-B receptor | LBR pS99 |
| Neurobeachin-like protein 2 | NBEAL2 pS2739 |
| Tensin-3 | TNS3 pS776 |
| MAP7 domain-containing protein 1 | MAP7D1 pS313 |
| Minor histocompatibility protein HA-1 | HMHA1 seq: 576-609 + 2 Phospho (ST) |
| Syntaxin-7 | STX7 seq: 124-138 + Phospho (ST) |
| DENN domain-containing protein 1A | DENND1A seq: 518-531 + Phospho (ST) |
| Tensin-3 | TNS3 pS776 |
| Drebrin-like protein | DBNL pS232 |
| Rab3 GTPase-activating protein catalytic subunit | RAB3GAP1 seq: 535-551 + Phospho (ST) |
| DNA-dependent protein kinase catalytic subunit | PRKDC seq: 3197-3217 + Phospho (ST) |
| Neuroblast differentiation-associated protein AHNAK | AHNAK pS93 |
| Cytoplasmic dynein 1 heavy chain 1 | DYNC1H1 pS4368 |
| Synaptojanin-1 | SYNJ1 pS1049 pS1053 |
| Protein Hook homolog 3 | HOOK3 pS707 |
| Mitochondrial inner membrane protein | IMMT pS113 |
| Phosphorylase b kinase regulatory subunit beta | PHKB pS27 |
| Minor histocompatibility protein HA-1 | HMHA1 pS23 |
| Hematopoietic lineage cell-specific protein | HCLS1 pY198 |
| Rho GTPase-activating protein 15 | ARHGAP15 pS43 |
| 26S proteasome non-ATPase regulatory subunit 4 | PSMD4 pS256 |
| Putative 3-phosphoinositide-dependent protein kinase 2 | PDPK2 pS214 |
| Uncharacterized protein C7orf43 | C7orf43 pS517 |
| Minor histocompatibility protein HA-1 | HMHA1 seq: 576-606 + Phospho (ST) |
| RNA-binding protein 14 | RBM14 pS256 |
| Serine/threonine-protein kinase PAK 2 | PAK2 seq: 139-160 + Phospho (ST) |
| FYVE, RhoGEF and PH domain-containing protein 3 | FGD3 pS56 |
| Coronin-7 | CORO7 pS21 |
| TBC1 domain family member 5 | TBC1D5 pS730 |
| Minor histocompatibility protein HA-1 | HMHA1 seq: 576-606 + Phospho (ST) |
| CapZ-interacting protein | RCSD1 seq: 177-188 + Phospho (ST) |
| Zinc finger CCCH domain-containing protein 13 | ZC3H13 seq: 875-885 + Phospho (ST) |
| Putative RNA-binding protein 15 | RBM15 seq: 123-132 + Phospho (ST) |
| Remodeling and spacing factor 1 | RSF1 pS748 |
| Zinc finger protein 768 | ZNF768 pS125 |
| Zinc finger protein 609 | ZNF609 seq: 571-582 + Phospho (ST) |
| Tumor suppressor p53-binding protein 1 | TP53BP1 pS1362 |
| Cyclin-dependent kinase 13 | CDK13 pS437 pS439 |
| Activity-dependent neuroprotector homeobox protein | ADNP pS953 |
| Mediator of DNA damage checkpoint protein 1 | MDC1 pS780 |
| Transcription elongation factor A protein 1 | TCEA1 pS100 |
| Msx2-interacting protein | SPEN pS1062 |

TABLE 2-continued

| Phosphoprotein | Phosphopeptide |
| --- | --- |
| ATPase family AAA domain-containing protein 2B | ATAD2B pS81 |
| DNA-directed RNA polymerase I subunit RPA43 | TWISTNB pS316 |
| Tumor suppressor p53-binding protein 1 | TP53BP1 pS265 |
| Tumor suppressor p53-binding protein 1 | TP53BP1 seq: 372-387 + Phospho (ST) |
| REST corepressor 3 | RCOR3 seq: 366-389 + Phospho (ST) |
| Protein lyl-1 | LYL1 pS36 |
| Serine/arginine repetitive matrix protein 2 | SRRM2 seq: 1457-1467 + Oxidation (M); Phospho (ST) |
| E3 SUMO-protein ligase RanBP2 | RANBP2 seq: 1507-1522 + Phospho (ST) |
| Transcription factor 12 | TCF12 seq: 75-90 + Phospho (ST) |
| Transcription factor 12 | TCF12 seq: 75-90 + Phospho (Y) |
| Lysine-specific histone demethylase 1A | KDM1A pS166 |
| DNA-directed RNA polymerase I subunit RPA43 | TWISTNB pS328 |

Advantageously, the panel of phosphorylation sites may comprise one or more phosphorylation sites in kinases, including one, two, three, four, five, six, seven, eight, nine, ten or more than ten of PAK1 at S144, PAK2 at S141, MAPK1 at Y187, MAPK1 at T185, RPS6KA1 at S380, MAPK3 at T202, MAPK3 at Y204, MAP3K3 at S166, SYK at S295 and S297, IRAK3 at S110, PKN1 (379-396+phospho ST), STK10 (447-464+phospho ST), RIPK3 at S410, PRKCD at T218, PRKCD at T295, PRKCD at Y313, PRKCD at T507, PRKCD at T645, PRKCD at S664, PRKCD at T2638, MARK2 at S535, MAP3K2 at S535, PRKD2 (710-730+phospho Y), NRK at s805, PRKAR2A at S58, ZAK (591-616+phospho ST), MAP4K4 at S900, CDK9 at S347, RPS6KA4 (681-699+2 phospho ST), MAST3 (1254-1274+phospho ST), NEK9 (10-39+phospho ST), GSK3A (19-50+phospho ST), RPS6KA3 at S369, RIPK2 at S531, AAK1 at T606, TYK2 at Y292, PDPK2 at S214, PRKAA1 (3-8+phospho ST), STK11P at S772, BAZ1B at S1468, CLK1 at S140, MAP4K2 at S328, WNK1 (1996-2021+phospho ST), CDK11A at S271, FES at Y713, and/or TNIK at S769, and step (a) may comprise analysing the data to determine if the panel of phosphopeptides is phosphorylated at a high level in the leukaemia cells, where an advanced differentiation status is determined if the panel of phosphopeptides is phosphorylated at a high level in the cells Preferably, the panel of phosphorylation sites may comprise regulatory phosphorylation sites in kinases, such as PAK1 at S144, PAK2 at S141, MAPK1 at Y187 and/or T185, and RPS6KA1 at S380, and step (a) may comprise analysing the data to determine if the panel of phosphopeptides is phosphorylated at a high level in the leukaemia cells, where an advanced differentiation status is determined if the panel of phosphopeptides is phosphorylated at a high level in the cells.

Suitably, the panel of phosphorylation sites may include MAPK1 at Y187, PAK2 at S141 and PRKCD at Y313, and step (a) may comprise analysing the data to determine if the panel of phosphopeptides is phosphorylated in the leukaemia cells, where an advanced differentiation status is determined if the panel of phosphopeptides is phosphorylated in the cells.

Optionally, the panel of phosphorylation sites may include FES at Y713, MAPK3 at T202/Y204, MAPK1 at T185/Y187, PAK1 at S144, MEK1 at S222, PAK2 at S141 and PRKCD at S645, and step (a) may comprise analysing the data to determine if the panel of phosphopeptides is phosphorylated in the leukaemia cells, where an advanced differentiation status is determined if the panel of phosphopeptides is phosphorylated in the cells.

The panel of phosphorylation sites may, for example, include one or more phosphorylation sites on one or more PKC isoforms including PRKCA, PRKCB and/or PRKCD), and/or one or more phosphorylation sites on one or more of STK10, GSK3A, PAK1, PAK2 and Gi24 (VSIR), as indicated in Table 1. For example, the panel of phosphorylation sites may include S21 of GSK3A and/or T507, T295, T218, Y313, T507, and/or S664 of PRKCD, and/or S20 of STK10, and/or S13 of STK10, and/or S144 of PAK1, and/or S141 of PAK2.

Suitably, the panel of phosphorylation sites may consist of phosphorylation sites on MAPK1, including at Y187 and/or T185 of MAPK1, and/or at T202 or Y204 of MAPK3, and/or at S21 of GSK3A, and step (a) may comprise analysing the data to determine if the panel of phosphopeptides is phosphorylated in the leukaemia cells, where an advanced differentiation status is determined if the panel of phosphopeptides is phosphorylated in the cells.

Said data recording the classification of the leukaemia cells under the French-American-British (FAB) classification system may comprise data of any kind which indicates the FAB classification of the leukaemia cells. An advanced differentiation status may be determined if the leukaemia cells are classified as M4, M4 eos or M5, preferably if the leukaemia cells are classified as M4.

The methods of the invention enable the effective identification of AML patients who are suitable for kinase inhibitor therapy, based on the differentiation status of the patients' leukaemia. Whilst kinase inhibitors of various types have previously been suggested as candidates for use in AML therapy, there has been no previous disclosure or suggestion that the differentiation status of a patient's leukaemia may in any way indicate suitability for kinase inhibitor therapy. The present invention therefore provides a new and non-obvious grouping of AML patients who are suitable for kinase inhibitor therapy. As proved by the specific examples, this grouping is highly selective for AML patients who will respond to kinase inhibitor therapy.

According to yet another aspect, therefore, the invention provides a kinase pathway inhibitor, which kinase pathway inhibitor inhibits a kinase signalling pathway that is involved in cell proliferation or cell survival, for use in a method of treating acute myeloid leukaemia in a patient, wherein the patient has leukaemia cells with an advanced differentiation status. Preferably, the differentiation status of the leukaemia cells may be determined according to the methods of the invention as described herein.

A kinase pathway inhibitor is an agent such as a small molecule or antibody which blocks the activity of a kinase pathway. Kinase pathway inhibitors may include inhibitors of enzyme and kinase pathway signalling molecules, including kinases, phosphatases, and G proteins. Suitably, the kinase pathway inhibitor may be a kinase inhibitor. A kinase inhibitor is an agent which blocks the kinase activity of a protein kinase. Such agents are well known and are widely available in the art. The inhibitory capability of a kinase inhibitor can be assessed by determining the activity of a kinase before and after incubation with the candidate compound. Kinase profiling methods for identifying kinase inhibitors are also widely available in the art, thus putting a large range of kinase inhibitors for use in the present invention at the disposal of the skilled person. One assay which may be used for the identification of agents capable of inhibiting specific kinases is a radioactive filter binding assay using 33P ATP, described in Hastie, et al 2006. Nat Protoc. 2006; 1(2):968-71; Bain, et al 2007. Biochem J. 2007 Dec. 15; 408(3):297-315. This method is sensitive, accurate and provides a direct measure of activity. Thus results are directly comparable between samples.

Preferably, the kinase pathway inhibitor may inhibit any one or more of the FLT3 pathway, the PKC pathway, the RAS-RAF-MEK-ERK pathway, the PI3K-AKT-MTOR-S6K pathway, the PAK pathway, the JAK-STAT pathway, the CAMKK pathway, or any kinase signalling pathway parallel thereto. The kinase pathway inhibitor may, for example, be a kinase inhibitor which inhibits one or more of PKC, PAK, RAF, MEK, ERK, PI3K, AKT, MTOR, S6K, STAT5, CAMKK, SYK, LYN, JAK, RTK, ALK, CDK, and BTK.

In some embodiments, the kinase pathway inhibitor may be a kinase inhibitor which is:

(a) a MEK inhibitor selected from APS-2-79, AZ 628, AZD8330, BI-847325, Binimetinib, BIX 02188, CEP-32496, Cobimetinib, Dabrafenib, DEL-22379, ERK5-IN-1, FR 180204, GDC-0623, GDC-0994, HA15, Honokiol, PD0325901, PD184352, PD318088, PD98059, Pimasertib, PLX7904, Refametinib, R05126766, SC1, SCH772984, SCH772984, Selumetinib, SGX-523, SL-327, Sorafenib, TAK733, Trametinib, U0126, U0126, Ulixertinib, Vandetanib, Vemurafenib, VX-11e, and XMD8-92; or (b) a FLT3 inhibitor selected from AMG 925, Amuvatinib, AZD2932, Cabozantinib, Dovitinib, ENMD-2076, ENMD-2076 L-(+)-Tartaric acid, G-749, KW-2449, Midostaurin, Pacritinib, Quizartinib, R406, Tandutinib, TCS 359, TG101209, and UNC2025; or an RTK inhibitor selected from Imatinib, Lenvatinib, Lucitanib, Sunitinib, Osimertinib, Erlotinib, Gefitinib, Dasatinib, Nilotinib, Lapatinib, Pazopanib, Ruxolitinib, Ponatinib, Cabozantinib, Regorafenib, Bosutinib, Axitinib, Afatinib, and Nintedanib; or (c) a PKC inhibitor selected from Enzastaurin, Bisindolylmaleimide I, Daphnetin, Dequalinium Chloride, Go 6983, Go6976, LY333531 HCl, Ro 31-8220 Mesylate, Sotrastaurin, and Staurosporine; or (d) a PAK inhibitor selected from FRAX1013, FRAX486, FRAX597, IPA-3, and PF3758309; or (e) a PI3K/AKT/MTOR inhibitor selected from 3-Methyladenine, A66, A-674563, Afuresertib, Akti-1/2, Alpelisib, AMG319, Apitolisib, AS-252424, AS-604850, AS-605240, AT13148, AT7867, AZD1208, AZD5363, AZD6482, AZD8055, AZD8186, AZD8835, BGT226, BI-78D3, Buparlisib, CAY10505, CC-223, CCT128930, CH5132799, Copanlisib, CP-466722, CPI-360, CUDC-907, CX-6258 HCl, CZ415, CZC24832, Dactolisib, Duvelisib, ETP-46464, Everolimus, GDC-0084, GDC-0349, Gedatolisib, GNE-317, GSK1059615, GSK2269557, GSK2292767, GSK2636771, GSK690693, HS-173, IC-87114, Idelalisib, INK 128, Ipatasertib, KU-0060648, KU-0063794, KU-55933, LTURM34, LY294002, LY3023414, MHY1485, Miltefosine, Miransertib, MK-2206, NU7026, NU7441, Omipalisib, OSI-027, Palomid 529, Perifosine, PF-04691502, PF-4989216, PHT-427, PI-103, PI-3065, Pictilisib, PIK-293, PIK-294, PIK-90, PIK-93, Pilaralisib, PIM447, Piperlongumine, PKI-402, PP121, Rapamycin, Ridaforolimus, SAR405, SC79, SGI-1776, SIS3, SKI II, SRPIN340, Tacrolimus, Taselisib, Temsirolimus, TG100-115, TG100713, TGR-1202, TIC10, TIC10 Analogue, Torin 1, Torin 2, Torkinib, Triciribine, Uprosertib, VE-821, Vistusertib, Voxtalisib, VPS34-IN1, VS-5584, WAY-600, Wortmannin, WYE-125132, WYE-354, WYE-687, XL147 analogue, XL388, Zotarolimus and ZSTK474; or (f) an ALK inhibitor selected from Ceritinib, Brigatinib, Crizotinib, and Alecitinib; or (g) a CDK inhibitor selected from Palbociclib and Ribociclib; or (h) a JAK inhibitor such as Tofacitinib; or (i) a BTK inhibitor such as Ibrutinib.

The kinase pathway inhibitor may, for example, be one of afatinib, alecitinib, alpelisib, axitinib, bosutinib, brigatinib, buparlisib, cabozantinib, ceritinib, cobimetinib, copanlisib, crizotinib, dabrafenib, dasatinib, dequalinium chloride, duvelisib, erlotinib, everolimus, gefitinib, ibrutinib, idelalisib, imatinib, lapatinib, lenvatinib, miltefosin, nilotinib, nintedanib, osimertinib, pacritinib, palbociclib, pazopanib, ponatinib, quizartinib, radaforolimus, rapamycin, regorafenib, ribociclib, ruxolitinib, selumetinib, sorafenib, sunitinib, temsirolimus, tofacitinib, vandetanib, vemurafenib and zotarolimus.

In some preferred embodiments, the kinase pathway inhibitor may be a MEK inhibitorsuch as APS-2-79, AZ 628, AZD8330, BI-847325, Binimetinib, BIX 02188, CEP-32496, Cobimetinib, Dabrafenib, DEL-22379, ERK5-IN-1, FR 180204, GDC-0623, GDC-0994, HA15, Honokiol, PD0325901, PD184352, PD318088, PD98059, Pimasertib, PLX7904, Refametinib, R05126766, SC1, SCH772984, SCH772984, Selumetinib, SGX-523, SL-327, Sorafenib, TAK733, Trametinib, U0126, U0126, Ulixertinib, Vandetanib, Vemurafenib, VX-11e, or XMD8-92; or a FLT3/PKC inhibitor such as midostaurin; or a PAK inhibitor such as FRAX1013, FRAX486, FRAX597, IPA-3, and PF3758309; or a PI3K/AKT/MTOR inhibitor selected from 3-Methyladenine, A66, A-674563, Afuresertib, Akti-1/2, Alpelisib, AMG319, Apitolisib, AS-252424, AS-604850, AS-605240, AT13148, AT7867, AZD1208, AZD5363, AZD6482, AZD8055, AZD8186, AZD8835, BGT226, BI-78D3, Buparlisib, CAY10505, CC-223, CCT128930, CH5132799, Copanlisib, CP-466722, CPI-360, CUDC-907, CX-6258 HCl, CZ415, CZC24832, Dactolisib, Duvelisib, ETP-46464, Everolimus, GDC-0084, GDC-0349, Gedatolisib, GNE-317, GSK1059615, GSK2269557, GSK2292767, GSK2636771, GSK690693, HS-173, IC-87114, Idelalisib, INK 128, Ipatasertib, KU-0060648, KU-0063794, KU-55933, LTURM34, LY294002, LY3023414, MHY1485, Miltefosine, Miransertib, MK-2206, NU7026, NU7441, Omipalisib, OSI-027, Palomid 529, Perifosine, PF-04691502, PF-4989216, PHT-427, PI-103, PI-3065, Pictilisib, PIK-293, PIK-294, PIK-90, PIK-93, Pilaralisib, PIM447, Piperlongumine, PKI-402, PP121, Rapamycin, Ridaforolimus, SAR405, SC79, SGI-1776, SIS3, SKI II, SRPIN340, Tacrolimus, Taselisib, Temsirolimus, TG100-

115, TG100713, TGR-1202, TIC10, TIC10 Analogue, Torin 1, Torin 2, Torkinib, Triciribine, Uprosertib, VE-821, Vistusertib, Voxtalisib, VPS34-IN1, VS-5584, WAY-600, Wortmannin, WYE-125132, WYE-354, WYE-687, XL147 analogue, XL388, Zotarolimus or ZSTK474. Suitably, the kinase pathway inhibitor may be trametinib, or midostaurin, or PF 3758309.

In particularly preferred embodiments of the present invention, the kinase pathway inhibitor is a MEK inhibitor, a FLT3/PKC inhibitor or a PAK inhibitor, and step (a) involves:

(i) determining the differentiation status of the patient's leukaemia by analysing data relating to the phosphorylation of one or more phosphorylation sites in MAPK1 and/or MAPK3 in leukaemia cells obtained from the patient; and/or (ii) determining the differentiation status of the patient's leukaemia by analysing data relating to the surface expression on leukaemia cells obtained from said patient of a group of CD markers consisting of CD11b, CD14, CD15, CD16, CD33, CD38, CD44, CD45, CD64, CD123 and HLA-DR; wherein a high level of phosphorylation of the one or more phosphorylation sites and/or the presence of said group of CD markers on said leukaemia cells indicates an advanced differentiation status.

Said one or more phosphorylation sites in MAPK1 may include Y187 and/or T185. Said one or more phosphorylation sites in MAPK3 may include T202 and/or Y204.

As demonstrated by the experimental data provided herein, the inventors have found that the present invention provides an accurate test for identifying AML patients who will be responsive to treatment with FLT3/PKC pathway inhibitors such as midostaurin.

In preferred embodiments, therefore, the kinase pathway inhibitor is a FLT3/PKC pathway inhibitor such as midostaurin, and step (a) involves determining the differentiation status of the patient's leukaemia by:

(i) analysing data relating to the phosphorylation of phosphorylation sites in one or more of GSK3A, PRKCA, PRKCB, PRKCD, STK10, PAK1, PAK2MAPK1 and/or MAPK3 in leukaemia cells obtained from the patient; and/or (ii) analysing data relating to the surface expression on leukaemia cells obtained from said patient of a group of CD markers consisting of CD11b, CD14, CD15, CD16, CD33, CD38, CD44, CD4PKC5, CD64, CD123 and HLA-DR; wherein either: a high level of phosphorylation in the leukaemia cells of GSK3A, PRKCA, PRKCB, PRKCD, STK10, PAK1, PAK2MAPK1 and/or MAPK3; or expression by the leukaemia cells of said group of CD markers; indicates an advanced differentiation status.

In these embodiments, said data relating to the phosphorylation of one or more phosphorylation sites in GSK3A, PRKCA, PRKCB, PRKCD, STK10, PAK1, PAK2MAPK1 and/or MAPK3 may comprise data relating to: the phosphorylation of GSK3A at pS21 and/or the phosphorylation of PRKCD at Y313, pT507, pT295, pT218, and/or pS664 and/or the phosphorylation of STK10 at pS20 and/or pS13, and/or the phosphorylation of PAK1 at pS144 and/or the phosphorylation of PAK2 at pS141, and/or the phosphorylation of MAPK1 at Y187 and/or T185, and/or the phosphorylation of MAPK3 at T202 and/or Y204.

The present invention also provides a highly accurate protocol for identifying AML patients who will respond to treatment with RAS-RAF-MEK-ERK pathway inhibitors, such as trametinib. The inventors have found that leukaemia cells with an advanced differentiation status are highly sensitive to treatment with such inhibitors. Such cells frequently have activating mutations in NRAS, KRAS, HRAS and/or BRAF. Testing for the presence of such activating mutations therefore supplements the protocol of the present invention.

In some preferred embodiments of the first aspect of the invention, therefore, the kinase pathway inhibitor is a RAS-RAF-MEK-ERK inhibitor such as trametinib; step (a) further comprises determining the mutational status of NRAS, KRAS, HRAS or BRAF in leukaemia cells obtained from the patient by analysing data relating to the genotype of the leukaemia cells; and step (b) comprises predicting that the acute myeloid leukaemia of the patient may be effectively treated with the kinase pathway inhibitor if the differentiation status of the leukaemia is advanced or if any one of NRAS, KRAS, HRAS or BRAF in the leukaemia cells has an activating mutation.

In some preferred embodiments of the second aspect of the invention, the kinase pathway inhibitor is a RAS-RAF-MEK-ERK inhibitor such as trametinib; step (a) further comprises determining the mutational status of NRAS, KRAS, HRAS or BRAF in leukaemia cells obtained from the patient by analysing data relating to the genotype of the leukaemia cells; and step (b) comprises treating the patient with the kinase pathway inhibitor if the differentiation status of the leukaemia is advanced or if any one of NRAS, KRAS, HRAS or BRAF in the leukaemia cells has an activating mutation.

In some preferred embodiments of the third aspect of the invention, the kinase pathway inhibitor is a RAS-RAF-MEK-ERK inhibitor such as trametinib; step (a) further comprises determining the mutational status of NRAS, KRAS, HRAS or BRAF in leukaemia cells obtained from the patient by analysing data relating to the genotype of the leukaemia cells; and step (b) comprises identifying any one or more patients who have leukaemia with an advanced differentiation status and/or who have leukaemia with an activating mutation in any one of NRAS, KRAS, HRAS or BRAF, and determining that said one or more patients may be suitable for effective treatment with the kinase pathway inhibitor.

In some preferred embodiments of the fourth aspect of the invention, the kinase pathway inhibitor is a RAS-RAF-MEK-ERK inhibitor such as trametinib; step (a) further comprises determining the mutational status of NRAS, KRAS, HRAS or BRAF in leukaemia cells obtained from the patient by analysing data relating to the genotype of the leukaemia cells; and step (b) comprises treating the patient with the kinase pathway inhibitor if the differentiation status of the leukaemia is advanced or if any one of NRAS, KRAS, HRAS or BRAF in the leukaemia cells has an activating mutation.

In these preferred embodiments, an activating mutation of NRAS, KRAS, HRAS or BRAF is a mutation which has the effect of constitutively switching the protein "on". Such mutations may, for example, include:

NRAS:

| G12S (c.34G > A) | G12C (c.34G > T) | G12R (c.34G > C) | G12V (c.35G > A) |
| G12A (c.35G > C) | G12D (c.35G > A) | G13A (c.38G > C) | G13V (c.38G > T) |
| G13R (c.37G > C) | G13C (c.37G > T) | G13S (c.37G > A) | G13D (c.38G > A) |

-continued

| Q61E (c.181C > G) | Q61H (c.183A > T) | Q61H (c.183A > C) | Q61L (c.182A > T) |
| Q61L (c.182_183AA > TG) | Q61K (c.181C > A) | Q61P (c.182A > C) | |
| Q61R (c.182A > G) | Q61R (c.182_183AA > GG) | Q61Q (c.183A > G) | |

BRAF:

| V600E (c.1799T > A) | V600K (c.1798_1799GT > AA) | V600M (c.1798G > A) |
| V600D (c. 1799_1800TG > AT) | V600R (c. 1798_1799GT > AG) | |
| V600G (c.1799T > G) | V600E'(c. 1799_1800TG > AA) | V600A (c. 1799_T > C) |
| G469A (c. 1406G > A) | G469V (c. 1406G > T) | D594G (c. 1781A > G) |
| D594V (c. 34G > A) | L597 (c.1789C) | L597 (c.1790T) |

KRAS:

| G12D (c.34G) | G12 (c.35G) | G13 (c.37G) | G12 (c.38G) |
| Q61 (c.181C) | Q61 (c.182A) | Q61 (c.183A) | A146 (c.436G) |
| A146 (c.437C) | | | |

HRAS:

| G12V (c.34G) | G12 (c.35G) | G13 (c.37G) | G13 (c.38G) |
| Q61 (c.181C) | Q61 (c.182A) | Q61 (c.183G) | |

In these embodiments, said data relating to the genotype of the leukaemia cells may comprise any information from which a skilled person could deduce the presence or absence of an activating mutation in NRAS, KRAS, HRAS and/or BRAF. The data may include, without limitation, the sequence of the NRAS, KRAS, HRAS and/or BRAF genes in the leukaemia cells, the sequence of the or each encoded protein expressed by the leukaemia cells, or data recording the presence or absence of an activating mutation in NRAS, KRAS, HRAS and/or BRAF in the leukaemia cells. In some embodiments, said data has previously been gathered and recorded and step (a) comprises obtaining said data for analysis. In other embodiments, step (a) further comprises gathering and recording said data for analysis. Said data may be gathered and recorded without difficulty according to techniques and protocols well known in the art and as exemplified herein.

In these embodiments, step (a) may comprise:

(i) determining the differentiation status of the patient's leukaemia by analysing data relating to the phosphorylation of one or more phosphorylation sites in MAPK1 or MAPK3 in leukaemia cells obtained from the patient; and/or (ii) determining the differentiation status of the patient's leukaemia by analysing data relating to the surface expression on leukaemia cells obtained from said patient of a group of CD markers consisting of CD11b, CD14, CD15, CD16, CD33, CD38, CD44, CD45, CD64, CD123 and HLA-DR; wherein a high level of phosphorylation of the one or more phosphorylation sites and/or the presence of said group of CD markers on said leukaemia cells indicates an advanced differentiation status.

The present inventors have also found that leukaemia cells possessing an activating mutation in FLT3, or displaying activation of a FLT3-driven pro-survival kinase signalling pathway operating in parallel to the RAS-RAF-MEK-ERK pathway, or having a high level of phosphorylation on certain phosphomarkers as identified below, can show resistance to treatment with MEK pathway inhibitors. It is thought that mutation of FLT3 and/or activation of parallel FLT3-driven pro-survival signalling pathways may provide the cells with alternative survival mechanisms notwithstanding the inhibition of the RAS-RAF-MEK-ERK pathway.

In some preferred embodiments of the invention, the kinase pathway inhibitor is a RAS-RAF-MEK-ERK pathway inhibitor such as a MEK inhibitor, such as trametinib, and step (a) further comprises:

(i) determining the mutational status of FLT3 in leukaemia cells obtained from the patient by analysing data relating to the genotype of said leukaemia cells and/or (ii) determining the activation in the leukaemia cells of a FLT-3 driven kinase signalling pathway that is involved in cell proliferation or cell survival other than the RAS-RAF-MEK-ERK pathway, such as the PKC pathway, the PI3K-AKT-MTOR-S6K pathway, the PAK pathway, the JAK-STAT pathway, or the CAMKK pathway, by analysing data relating to kinase pathway activity markers in said leukaemia cells; and/or (iii) determining the level of phosphorylation of one or both of TOP2A and/or KDM5C in the leukaemia cells, by analysing data relating to the phosphorylation of TOP2A and/or KDM5C in the leukaemia cells.

In such embodiments according to the first aspect of the invention, step (b) may comprise predicting that the acute myeloid leukaemia of the patient may be effectively treated with the RAS-RAF-MEK-ERK pathway inhibitor if: (i) the differentiation status of the leukaemia is advanced and (ii) if FLT3 in the leukaemia cells does not have an activating mutation or if the FLT3-driven kinase signalling pathway is not activated in the leukaemia cells or if TOP2A and/or KDM5C are phosphorylated at a low level in the leukaemia cells. In such embodiments according to the second aspect of the invention, step (b) may comprise treating the patient with the RAS-RAF-MEK-ERK pathway inhibitor if: (i) the differentiation status of the leukaemia is advanced and (ii) if FLT3 in the leukaemia cells does not have an activating mutation or if the FLT3-driven kinase signalling pathway is not activated in the leukaemia cells or if TOP2A and/or KDM5C are phosphorylated at a low level in the leukaemia cells. In such embodiments according to the third aspect of the invention, step (b) may comprise identifying as suitable for effective treatment with the RAS-RAF-MEK-ERK inhibitor any one or more patients for whom: (i) the leukaemia cells have an advanced differentiation status and (ii) the leukaemia cells have no activating mutation in FLT3 or the FLT3-driven kinase signalling pathway is not activated in the leukaemia cells or if TOP2A and/or KDM5C are phosphorylated at a low level in the leukaemia cells. In such embodiments according to the fourth aspect of the invention, step (b) may comprise treating the patient with the RAS-RAF-MEK-ERK inhibitor if: (i) the differentiation status of the leukaemia is advanced and (ii) if FLT3 in the leukaemia cells does not have an activating mutation or if the FLT3-driven kinase signalling pathway is not activated in the leukaemia cells or if TOP2A and/or KDM5C are phosphorylated at a low level in the leukaemia cells.

Some preferred related embodiments of the first aspect of the invention may accordingly comprise:

(a) (i) determining the differentiation status of the patient's leukaemia and/or determining the mutational status of NRAS, KRAS, HRAS or BRAF in leukaemia cells obtained from the patient by analysing data relating to the genotype of the leukaemia cells; and (ii) determining the mutational status of FLT3 in leukaemia cells obtained from the patient by analysing data relating to the genotype of said leukaemia cells and/or determining the activation in the leukaemia cells of a FLT-3 driven kinase signalling pathway that is involved in cell proliferation or cell survival other than the RAS-RAF-MEK-ERK pathway, by analysing data relating to activity markers of the FLT3-driven kinase signalling pathway in said leukaemia cells; and/or determining the level of phosphorylation of one or both of TOP2A and/or KDM5C in the leukaemia cells, by analysing data relating to the phosphorylation of TOP2A and/or KDM5C in the leukaemia cells and (b) where: (i) the differentiation status of the leukaemia is advanced or any one of NRAS, KRAS, HRAS or BRAF in the leukaemia cells has an activating mutation, and (ii) FLT3 in the leukaemia cells does not have an activating mutation or the FLT3-driven kinase signalling pathway is not activated or TOP2A and/or KDM5C are phosphorylated at a low level in the leukaemia cells;

predicting that the acute myeloid leukaemia in the patient may be effectively treated with said RAS-RAF-MEK-ERK pathway inhibitor.

Some preferred embodiments of the second aspect of the invention may accordingly comprise:

(a) (i) determining the differentiation status of the patient's leukaemia and/or determining the mutational status of NRAS, KRAS, HRAS or BRAF in leukaemia cells obtained from the patient by analysing data relating to the genotype of the leukaemia cells; and (ii) determining the mutational status of FLT3 in leukaemia cells obtained from the patient by analysing data relating to the genotype of said leukaemia cells and/or determining the activation in the leukaemia cells of a FLT-3 driven kinase signalling pathway that is involved in cell proliferation or cell survival other than the RAS-RAF-MEK-ERK pathway, by analysing data relating to activity markers of the FLT3-driven kinase signalling pathway in said leukaemia cells; and/or determining the level of phosphorylation of one or both of TOP2A and/or KDM5C in the leukaemia cells, by analysing data relating to the phosphorylation of TOP2A and/or KDM5C in the leukaemia cells and (b) where: (i) the differentiation status of the leukaemia is advanced or any one of NRAS, KRAS, HRAS or BRAF in the leukaemia cells has an activating mutation, and (ii) FLT3 in the leukaemia cells does not have an activating mutation or the FLT3-driven kinase signalling pathway is not activated or TOP2A and/or KDM5C are phosphorylated at a low level in the leukaemia cells;

treating the patient with said RAS-RAF-MEK-ERK pathway inhibitor.

Some preferred embodiments of the third aspect of the invention may accordingly comprise:

(a) for each patient:

(i) determining the differentiation status of the patient's leukaemia and/or determining the mutational status of NRAS, KRAS, HRAS or BRAF in leukaemia cells obtained from the patient by analysing data relating to the genotype of the leukaemia cells; and (ii) determining the mutational status of FLT3 in leukaemia cells obtained from the patient by analysing data relating to the genotype of said leukaemia cells and/or determining the activation in the leukaemia cells of a FLT-3 driven kinase signalling pathway that is involved in cell proliferation or cell survival other than the RAS-RAF-MEK-ERK pathway, by analysing data relating to activity markers of the FLT3-driven kinase signalling pathway in said leukaemia cells; and/or determining the level of phosphorylation of one or both of TOP2A and/or KDM5C in the leukaemia cells, by analysing data relating to the phosphorylation of TOP2A and/or KDM5C in the leukaemia cells; and (b) for any one or more patients where:

(i) the differentiation status of the leukaemia is advanced or any one of NRAS, KRAS, HRAS or BRAF in the leukaemia cells has an activating mutation, and (ii) FLT3 in the leukaemia cells does not have an activating mutation or the FLT3-driven kinase signalling pathway is not activated or TOP2A and/or KDM5C are phosphorylated at a low level in the leukaemia cells;

identifying the patient or patients as having leukaemia suitable for effective treatment with said RAS-RAF-MEK-ERK pathway inhibitor.

Some preferred embodiments of the fourth aspect of the invention may accordingly comprise:

(a) (i) determining the differentiation status of the patient's leukaemia and/or determining the mutational status of NRAS, KRAS, HRAS or BRAF in leukaemia cells obtained from the patient by analysing data relating to the genotype of the leukaemia cells; and (ii) determining the mutational status of FLT3 in leukaemia cells obtained from the patient by analysing data relating to the genotype of said leukaemia cells and/or determining the activation in the leukaemia cells of a FLT-3 driven kinase signalling pathway that is involved in cell proliferation or cell survival other than the RAS-RAF-MEK-ERK pathway, by analysing data relating to activity markers of the FLT3-driven kinase signalling pathway in said leukaemia cells; and/or determining the phosphorylation at one or more phosphorylation sites in one or both of TOP2A and/or KDM5C in the leukaemia cells, by analysing data relating to the phosphorylation of TOP2A and/or KDM5C in the leukaemia cells; and (b) where: (i) the differentiation status of the leukaemia is advanced or any one of NRAS, KRAS, HRAS or BRAF in the leukaemia cells has an activating mutation, and (ii) FLT3 in the leukaemia cells does not have an activating mutation or the FLT3-driven kinase signalling pathway is not activated or TOP2A and/or KDM5C are phosphorylated at a low level in the leukaemia cells;

treating the patient with said RAS-RAF-MEK-ERK pathway inhibitor.

In these preferred embodiments, an activating mutation of FLT3 is a mutation which has the effect of constitutively switching the FLT3 protein "on". Such mutations may, for example, include internal tandem duplications (ITD) of the juxtamembrane domain or point mutations usually involving the tyrosine kinase domain, such as at D835. Said data relating to the genotype of the leukaemia cells may comprise any information from which a skilled person could deduce the presence or absence of an activating mutation in FLT3. The data may include, without limitation, the sequence of the FLT3 gene in the leukaemia cells, the sequence of the FLT3 protein expressed by the leukaemia cells, or data recording the presence or absence of an activating mutation in FLT3 in the leukaemia cells. Said data may be gathered and interpreted by the skilled person without difficulty according to techniques and protocols well known in the art.

In these preferred embodiments, said step of determining the activation in the leukaemia cells of a FLT3-driven kinase signalling pathway that is involved in cell proliferation or cell survival other than the RAS-RAF-MEK-ERK pathway may comprise determining the activation of more than one FLT3-driven kinase signalling pathway. The or each FLT3-driven kinase signalling pathway may preferably be selected from the PKC pathway, the PI3K-AKT-MTOR-S6K pathway, the PAK pathway, the JAK-STAT pathway, or the CAMKK pathway. Preferably, the FLT3-driven kinase signalling pathway may be the JAK-STAT pathway, the PI3K-AKT-MTOR-S6K pathway or the CAMKK pathway. Suitably, the FLT3-driven kinase signalling pathway may be the JAK-STAT (STAT5) pathway.

Said activity markers of the FLT3-driven kinase signalling pathway may include any markers which can be used to identify the activation of the FLT3-driven kinase signalling pathway. These may include any kinases, phosphatases, phospholipoases, integrins, signal transduction regulators, G proteins, transmembrane receptors, phosphopeptides and/or other kinase signalling molecules which are selectively activated in the FLT3-driven kinase signalling pathway, or any molecules which are selectively phosphorylated in the FLT3-driven kinase signalling pathway (phosphomarkers). Conveniently, the activity markers of the FLT3-driven kinase signalling pathway may include one or more phosphomarkers, and the data relating to the activity markers may comprise data relating to the phosphorylation of the one or more phosphomarkers, where a high level of phosphorylation of the one or more phosphomarkers indicates that the FLT3-driven kinase signalling pathway is activated.

Said one or more phosphomarkers may, for example, include phosphorylation sites in one or more of the proteins STAT5A and/or CAMKK1, for example phosphorylation sites at S780 and/or S128 of STAT5A, and phosphorylation sites at S548 of CAMKK1. These phosphorylation sites are selectively phosphorylated in FLT3-driven kinase signalling pathways. The data relating to the activity markers may thus comprise data relating to the level of phosphorylation of either or both of STAT5A and CAMKK1, such as the phosphorylation of STAT5A at S780 and/or S128, and/or the level of phosphorylation of CAMKK1 at S548, where a high level of phosphorylation indicates activation of the FLT3-driven kinase signalling pathway.

In these preferred embodiments, said data relating to the phosphorylation of TOP2A and/or KDM5C in the leukaemia cells may comprise data relating to the phosphorylation of TOP2A and/or KDM5C, such as data relating to the phosphorylation of TOP2A at S1213 and/or the phosphorylation of KDM5C at S317.

The present invention also envisages the use of alternative phosphomarkers of the FLT3-driven kinase signalling pathway, including the STAT5 pathway and/or the CAMKK pathway, which may equally be used for determining the activation of the FLT3-driven kinase signalling pathway.

The data relating to the activity markers may comprise any information from which a skilled person could deduce the activation of the activity markers, such as the expression or activation of the activity markers, such as the level of phosphorylation of the activity markers. Such data may include, for example, LC-MS/MS data. In some embodiments, said data has previously been gathered and recorded and step (a)(ii) comprises obtaining said data for analysis. In other embodiments, step (a)(ii) further comprises gathering and recording said data for analysis. Said data may be gathered and recorded without difficulty according to techniques and protocols well known in the art and as exemplified herein, for example by LC-MS/MS or by immunochemical techniques.

In these embodiments, the differentiation status of the leukaemia cells may be determined according to any of the method steps described herein. Preferably, however, said step of determining the differentiation status of the leukaemia cells may comprise:

(i) analysing data relating to the phosphorylation of one or more phosphorylation sites in MAPK1 or MAPK3 in leukaemia cells obtained from the patient; and/or (ii) determining the differentiation status of the patient's leukaemia by analysing data relating to the surface expression on leukaemia cells obtained from said patient of a group of CD markers consisting of CD11b, CD14, CD15, CD16, CD33, CD38, CD44, CD45, CD64, CD123 and HLA-DR;

wherein a high level of phosphorylation of the one or more phosphorylation sites and/or the presence of said group of CD markers on said leukaemia cells indicates an advanced differentiation status.

The present invention is of particular interest in respect of kinase pathway inhibitors which have been approved for treatment of AML or may shortly be approved for treatment of AML. These include the FLT3/PKC pathway inhibitor midostaurin, and the RAS-RAF-MEK-ERK pathway inhibitor trametinib. As demonstrated herein, the present invention provides a significantly improved protocol for identifying patients who will respond to treatment with these kinase pathway inhibitors. The availability of an accurate companion diagnostic test for identifying potentially responsive patients is of significant therapeutic and clinical benefit, as it will aid in ensuring that patients who will respond to treatment are identified as such and can benefit from this treatment, whilst patients who will not respond are not unnecessarily subjected to treatment.

The present invention accordingly provides midostaurin for use in a method of treating acute myeloid leukaemia in a patient, wherein the patient has leukaemia with an advanced differentiation status, defined by:

(i) surface expression on the leukaemia cells of the patient of a group of CD markers consisting of CD11b, CD14, CD15, CD16, CD33, CD38, CD44, CD45, CD64, CD123 and HLA-DR; and/or (ii) a high level of phosphorylation of phosphorylation sites on any one or more of GSK3A, PRKCA, PRKCB, PRKCD, STK10, PAK1, PAK2, MAPK1 and/or MAPK3 in the leukaemia cells of the patient.

In particular, the present invention provides midostaurin for use in a method of treating acute myeloid leukaemia in a patient, wherein the patient has leukaemia with an advanced differentiation status, defined by:

(i) surface expression on the leukaemia cells of the patient of a group of CD markers consisting of CD11b, CD14, CD15, CD16, CD33, CD38, CD44, CD45, CD64, CD123 and HLA-DR; and/or (ii) a high level of phosphorylation in the leukaemia cells of the patient of any one or more of:

pS21 of GSK3A;
pY313, pT507, pT295, pT218, and/or pS664 of PRKCD;
pS20 and/or pS13 of STK10;
pS144 of PAK1;
pS141 of PAK2;
Y187 and/or T185 of MAPK1; and
T202 and/or Y204 of MAPK3.

The present invention further provides trametinib for use in a method of treating acute myeloid leukaemia in a patient, wherein the patient has leukaemia with an advanced differentiation status and with low activation of FLT3-driven survival pathways, defined by:

(a) (i) a high level of phosphorylation of one or more phosphorylation sites in MAPK1 and/or MAPK3 in the leukaemia cells of the patient;
and/or
(ii) surface expression on the leukaemia cells of the patient of a group of
CD markers consisting of CD11b, CD14, CD15, CD16, CD33, CD38, CD44, CD45, CD64, CD123 and HLA-DR; and/or
(iii) activating mutations in any one of NRAS, KRAS, HRAS or BRAF in the leukaemia cells of the patient; and
(b) (i) a high level of phosphorylation of one or more of STAT5A, TOP2A, KDM5C and CAMKK1 in the leukaemia cells; and/or
(ii) the absence of any activating mutations in FLT3 in the leukaemia cells of the patient.

In particular, the present invention provides trametinib for use in a method of treating acute myeloid leukaemia in a patient, wherein the patient has leukaemia with an advanced differentiation status, defined by:

(a) (i) surface expression on the leukaemia cells of the patient of a group of CD markers consisting of CD11b, CD14, CD15, CD16, CD33, CD38, CD44, CD45, CD64 and HLA-DR; and/or
(ii) a high level of phosphorylation in the leukaemia cells of the patient of any one or more of Y187 and/or T185 of MAPK1; and T202 and/or Y204 of MAPK3;
(iii) activating mutations in any one or more of NRAS, KRAS, HRAS or BRAF in the leukaemia cells of the patient; and
(b) (i) a high level of phosphorylation at one or more of pS780 and pS128 of STAT5A, pS548 of CAMKK1, pS1213 of TOP2A and pS317 of KDM5C; and/or
(ii) the absence of any activating mutations in FLT3 in the leukaemia cells of the patient.

The invention further provides a method of treating acute myeloid leukaemia in an individual patient suffering from acute myeloid leukaemia, comprising the steps of:

(a) obtaining a biological sample comprising leukaemia cells from the patient;
(b) determining by in vitro laboratory testing that the differentiation status of the leukaemia cells in the sample obtained in (a) is advanced; and
(c) where the differentiation status of the leukaemia cells is advanced, administering a kinase pathway inhibitor to the patient, which kinase pathway inhibitor inhibits a signalling pathway that is involved in cell proliferation or cell survival.

The biological sample may be a peripheral blood sample or a bone marrow sample. The kinase pathway inhibitor may be selected from a MEK pathway inhibitor, a FLT3/PKC pathway inhibitor and a PAK pathway inhibitor.

In this aspect of the invention, step (b) may comprise detecting morphological and/or cytochemical features of the leukaemia cells in the sample obtained from the patient, where an M4 classification under the French-American-British (FAB) classification system indicates an advanced differentiation status.

Said step of detecting morphological and/or cytochemical features of the leukaemia cells may include preparing the cells for microscopical analysis and visually observing the cells under a light microscope to detect morphological signs of differentiation; and/or assaying the behaviour, activity or response of the cells to specific conditions or test reagents such as such as sudan black B and/or peroxidase and/or specific or non-specific esterases.

Optionally, step (b) may comprise performing an in vitro assay to detect the expression level of one or more cell surface differentiation markers on the surface of the leukaemia cells in the sample obtained from the patient, which cell surface differentiation markers are typically expressed or over-expressed in healthy myelomonocytic cells and which cell surface differentiation markers are not typically expressed or over-expressed in undifferentiated myeloblasts, where the expression of said one or more cell surface differentiation markers at a high level on the surface of the leukaemia cells indicates an advanced differentiation status. Said assay may be an LC-MS/MS assay or an immunochemical assay such as a Western blot assay, an ELISA assay or a reversed phase protein assay.

The cell surface differentiation markers may comprise a panel of cell surface marker proteins including one or more of CD3, CD7, CD11b, CD11c (integrin α-X, ITAX), CD14, CD15, CD16, CD18 (integrin β, ITB2), CD19, CD33, CD34, CD35 (CR1), CD38, CD44, CD45, CD64, CD97, CD117, CD123, CD180, CD184, HLA-C(1CO2), APOBR, the platelet membrane receptor Gi24 (VSIR) and HLA-DR; and/or any cell surface proteins which are expressed in conjunction with said one or more cell surface marker proteins.

Suitably, the panel of cell surface marker proteins may comprise:

(i) any one, two, or three, or four, or five, or six, or seven, or eight, or nine, or ten, or eleven, or twelve, or thirteen, or fourteen, or fifteen, or sixteen, or seventeen, or eighteen, or all of CD11b, CD11c (integrin α-X, ITAX), CD14, CD15, CD16, CD18 (integrin β, ITB2), CD33, CD35 (CR1), CD38, CD44, CD45, CD64, CD97, CD123, CD180, HLA-C (1CO2), APOBR, the platelet membrane receptor Gi24 (VSIR) and HLA-DR; or (ii) any one, two, three, four, five, six, seven, eight, nine, ten or all of CD11b, CD14, CD15, CD16, CD33, CD38, CD44, CD45, CD64, CD123 and HLA-DR; or (iii) any one, two, three, four, five, six, seven, eight, nine, ten, eleven, twelve, thirteen, fourteen, fifteen, sixteen or all of CD3, CD7, CD11b, CD14, CD15, CD16, CD19, CD33, CD34, CD38, CD44, CD45, CD64, CD117, CD123, CD184, and HLA-DR.

In methods of treatment according to this aspect of the invention, step (b) may comprise performing an in vitro assay to detect the expression and/or activation and/or phosphorylation of one or more functional differentiation markers in the leukaemia cells in the sample obtained from the patient, which functional differentiation markers are typically expressed, over-expressed, activated and/or phosphorylated in healthy monomyelocytic cells, and which functional differentiation markers are not typically expressed, over-expressed, activated and/or phosphorylated in undifferentiated myeloblasts; wherein the expression, activation and/or phosphorylation of said one or more functional differentiation markers in the leukaemia cells indicates an advanced differentiation status. Said assay may be an LC-MS/MS assay or an immunochemical assay such as a Western blot assay, an ELISA assay or a reversed phase protein assay. The one or more functional differentiation markers may comprise a panel of protein markers including one or more enzymes, integrins, kinases, phosphatases, signal transduction regulators, cytoplasmic proteins and phosphoproteins, membrane proteins and phosphoproteins, including cytoplasmic and membrane phosphoproteins that are involved in GTPase or other forms of cell signalling, which protein markers are typically expressed, over-expressed and/or activated in healthy monomyelocytic cells, and are not typically expressed, over-expressed and/or activated in undifferentiated myeloblasts; and wherein the expression and/or activation of said panel of protein markers in the leukaemia cells indicates an advanced differentiation status.

Optionally, the panel of protein markers may include any one, two, three, four or five of lysozyme C (LYZ), neutrophil cytosol factor 2 (NCF2), myeloid cell nuclear differentiation antigen (MNDA), AK1C4, and ERG.

Suitably, the one or more functional differentiation markers may comprise a panel of kinase pathway activity markers including one or more kinases, phosphatases, phospholipoases, integrins, signal transduction regulators, G proteins, transmembrane receptors, phosphopeptides and/or other kinase signalling molecules that are typically expressed and/or activated and/or phosphorylated in a kinase signalling pathway in healthy monomyelocytic cells but are not typically expressed and/or activated and/or phosphorylated in undifferentiated myeloblasts; and wherein the expression and/or activation and/or phosphorylation of the panel of kinase pathway activity markers in the leukaemia cells indicates an advanced differentiation status. In particular, the panel of kinase pathway activity markers may comprise markers of a kinase signalling pathway that is inhibited by the kinase pathway inhibitor.

The panel of kinase pathway activity markers may, for example, comprise any one, two, three, four, five, six, seven, eight, nine, ten or more of FES, PKC and protein kinase C isoforms including PKCδ (KPCD), PRKCA, PRKCB, and PRKCD, PKA, PAK including PAK1 and PAK2, STK10, GSK3A, RSK2, RAS, RAF, MEK including MEK1 (MAP2K1), ERK including MAPK3 (ERK1) and MAPK1 (ERK2), PI3K, AKT including AKT1, MTOR, S6 kinase, STAT5, CAMKK, SYK (KSYK), LYN, P38A, CDK1, CK2A1, PKACA, IRAK4, PKCB iso2, Cot, PKCD, PKCA, PKCB, PKCG, PKCH, BRAF, MEK2, PDK1, CDK2, PTN6, D3 (PLD3), IQGAP1, GRB2, RHOA, RHOG and S10AB, and any kinases, phosphatases, phospholipoases, integrins, signal transduction regulators, G proteins, transmembrane receptors and/or other kinase signalling molecules that are selectively expressed or activated therewith.

In some embodiments, the panel of kinase pathway activity markers may comprise:
(i) any one, two, three, or four of PKC, ERK, PAK1 and P38α;
(ii) any one, two, three, four or five of PKCD, PKCA, PKACA, IRAK4 and CK2A1; or
(iii) any one, two, three, four, five or six of MAPK1, MAPK2, AKT, AKT1S1, MAP2K1 and MAP2K2.

In some embodiments, the panel of kinase pathway activity markers may comprise a panel of one or more phosphorylation sites which are typically phosphorylated or are typically phosphorylated at a high level in a kinase signalling pathway in healthy monomyelocytic cells but are not typically phosphorylated or are not typically phosphorylated at a high level in undifferentiated myeloblasts; and wherein phosphorylation or a high level of phosphorylation at the panel of phosphorylation sites in the leukaemia cells indicates an advanced differentiation status.

In such embodiments, the panel of phosphorylation sites may comprise:
(i) any one, two, three, four, five, six, seven, eight, nine, ten or more than ten of the phosphorylation sites set out in Table 1; or
(ii) any one, two, three, four, five, six, seven, eight, nine, ten or more than ten of the phosphorylation sites set out in Table 2; or
(iii) any one, two, three, four, five, six, seven, eight, nine, ten or more than ten of PAK1 at 5144, PAK2 at 5141, MAPK1 at Y187, MAPK1 at T185, RPS6KA1 at 5380, MAPK3 at T202, MAPK3 at Y204, MAP3K3 at S166, SYK at 5295 and 5297, IRAK3 at S110, PKN1 (379-396+phospho ST), STK10 (447-464+phospho ST), RIPK3 at 5410, PRKCD at T218, PRKCD at T295, PRKCD at Y313, PRKCD at T507, PRKCD at T645, PRKCD at 5664, PRKCD atT2638, MARK2 at 5535, MAP3K2 at S535, PRKD2 (710-730+phospho Y), NRK at s805, PRKAR2A at S58, ZAK (591-616+phospho ST), MAP4K4 at S900, CDK9 at S347, RPS6KA4 (681-699+2 phospho ST), MAST3 (1254-1274+phospho ST), NEK9 (10-39+phospho ST), GSK3A (19-50+phospho ST), RPS6KA3 at S369, RIPK2 at S531, AAK1 at T606, TYK2 at Y292, PDPK2 at S214, PRKAA1 (3-8+phospho ST), STK11P at S772, BAZ1B at S1468, CLK1 at S140, MAP4K2 at S328, WNK1 (1996-2021+phospho ST), CDK11A at S271, FES at Y713, and/or TNIK at S769; or
(iv) PAK1 at S144, PAK2 at S141, MAPK1 at Y187 and/or T185, and RPS6KA1 at S380; or
(v) MAPK1 at Y187, PAK2 at S141 and PRKCD at Y313; or
(vi) FES at Y713, MAPK3 at T202/Y204, MAPK1 at T185/Y187, PAK1 at S144, MEK1 at S222, PAK2 at S141 and PRKCD at S645; or
(vii) GSK3A at S21 and/or PRKCD at T507, T295, T218, Y313, T507, and/or S664 and/or STK10 at S20 and/or S13, and/or PAK1 at S144, and/or PAK2 at S141.
(viii) one or more phosphorylation sites on MAPK1 including MAPK1 at Y187 and/or T185, and MAPK3 at T202 and/or Y204, and GSK3A at S21.

In methods of treating acute myeloid leukaemia according to the invention, the kinase pathway inhibitor may inhibit any one or more of the FLT3 pathway, the PKC pathway, the RAS-RAF-MEK-ERK pathway, the PI3K-AKT-MTOR-S6K pathway, the PAK pathway, the JAK-STAT pathway, the CAMKK pathway, or any kinase signalling pathway parallel thereto. Suitably, the kinase pathway inhibitor may be a MEK inhibitor, or a FLT3/PKC inhibitor, or a PAK inhibitor.

In such embodiments, step (b) may comprise:
(i) performing an in vitro assay to detect and/or quantify the phosphorylation of one or more phosphorylation sites in MAPK1 and/or MAPK3 in the leukaemia cells in the sample obtained from the patient; and/or (ii) performing an in vitro assay to detect and/or quantify the surface expression on the leukaemia cells in the sample obtained from said patient of a group of CD markers consisting of CD11b, CD14, CD15, CD16, CD33, CD38, CD44, CD45, CD64, CD123 and HLA-DR;
wherein phosphorylation or phosphorylation at a high level of the one or more phosphorylation sites and/or the expression of said group of CD markers at a high level on said leukaemia cells indicates an advanced differentiation status.

In methods of treating acute myeloid leukaemia according to the present invention wherein the kinase pathway inhibitor is a FLT3/PKC pathway inhibitor such as midostaurin, step (b) may comprise:
(i) performing an in vitro assay to detect and/or quantify the phosphorylation of phosphorylation sites in one or more of GSK3A, PRKCA, PRKCB, PRKCD, STK10, PAK1, PAK2MAPK1 and/or MAPK3 in the leukaemia cells in the sample obtained from the patient; and/or
(ii) performing an in vitro assay to detect and/or quantify the surface expression of a group of CD markers consisting of CD11b, CD14, CD15, CD16, CD33, CD38, CD44, CD4PKC5, CD64, CD123 and HLA-DR on the surface of the leukaemia cells in the sample obtained from the patient; wherein either: phosphorylation or a high level of phosphorylation in the leukaemia cells of any one or more of GSK3A, PRKCA, PRKCB, PRKCD, STK10, PAK1, PAK2, MAPK1 and/or MAPK3; or expression at a high level by the leukaemia cells of said group of CD markers; indicates an advanced differentiation status.

In methods of treating acute myeloid leukaemia according to the invention wherein the kinase pathway inhibitor is a MEK inhibitor such as trametinib, step (b) may further comprise performing an in vitro assay to detect the genotype of the leukaemia cells obtained from the patient and determining that any one of NRAS, KRAS, HRAS or BRAF in the leukaemia cells in the sample obtained from the patient has an activating mutation. Suitably, said assay may involve sequencing NRAS, KRAS, HRAS or BRAF in the leukaemia cells in the sample obtained from the patient, and identifying an activating mutation in the sequence data thereby obtained.

In these embodiments, step (b) may comprise:
(i) performing an in vitro assay to detect the phosphorylation of one or more phosphorylation sites in MAPK1 or MAPK3 in the leukaemia cells in the sample obtained from the patient; and/or
(ii) performing an in vitro assay to detect the surface expression of a group of CD markers consisting of CD11b, CD14, CD15, CD16, CD33, CD38, CD44, CD45, CD64, CD123 and HLA-DR on the leukaemia cells in the sample obtained from the patient;
wherein phosphorylation or a high level of phosphorylation of the one or more phosphorylation sites and/or the expression of said group of CD markers at a high level on said leukaemia cells indicates an advanced differentiation status.

In methods of treating acute myeloid leukaemia according to the invention wherein the kinase pathway inhibitor is a MEK inhibitor such as trametinib, step (b) may further comprise:
(i) performing an in vitro assay to detect the genotype of the leukaemia cells in the sample obtained from the patient and determining that FLT3 in the leukaemia cells does not have an activating mutation; and/or
(ii) performing an in vitro assay to detect the expression or activation in the leukaemia cells in the sample obtained from the patient of one or more activity markers of a FLT-3 driven signalling pathway that is involved in cell proliferation or cell survival other than the RAS-RAF-MEK-ERK pathway, such as the PKC pathway, the PI3K-AKT-MTOR-S6K pathway, the PAK pathway, the JAK-STAT pathway, or the CAMKK pathway, and determining that the FLT3-driven kinase signalling pathway is not activated in the leukaemia cells; and/or
(iii) performing an in vitro assay to detect the level of phosphorylation of one or both of TOP2A and/or KDM5C in the leukaemia cells in the sample obtained from the patient and determining that TOP2A and/or KDM5C are not phosphorylated or are phosphorylated at a low level in the leukaemia cells.

In methods of treating acute myeloid leukaemia according to the invention wherein the kinase pathway inhibitor is a MEK inhibitor such as trametinib, step (b) may comprise:
(i) performing an in vitro assay to detect the genotype of the leukaemia cells in the sample obtained from the patient and determining that any one of NRAS, KRAS, HRAS or BRAF in the leukaemia cells has an activating mutation; and/or determining that the differentiation status of the leukaemia cells in the sample obtained from the patient is advanced; and
(ii) performing an in vitro assay to detect the genotype of the leukaemia cells in the sample obtained from the patient and determining that FLT3 in the leukaemia cells does not have an activating mutation; and/or performing an assay to detect the expression or activation in the leukaemia cells in the sample obtained from the patient of one or more activity markers of a FLT-3 driven signalling pathway that is involved in cell proliferation or cell survival other than the RAS-RAF-MEK-ERK pathway, such as the PKC pathway, the PI3K-AKT-MTOR-S6K pathway, the PAK pathway, the JAK-STAT pathway, or the CAMKK pathway, and determining that the FLT3-driven kinase signalling pathway is not activated in the leukaemia cells; and/or performing an assay to detect the level of phosphorylation of one or both of TOP2A and/or KDM5C in the leukaemia cells in the sample obtained from the patient and determining that TOP2A and/or KDM5C are not phosphorylated or are phosphorylated at a low level in the leukaemia cells.

Suitably, said activity markers of the FLT3-driven kinase signalling pathway may include one or more phosphorylation sites which are selectively phosphorylated by the FLT3-driven kinase signalling pathway. In these embodiments, phosphorylation or a high level of phosphorylation of the one or more phosphorylation sites indicates that the FLT3-driven kinase signalling pathway is activated. Said one or more phosphorylation sites may include phosphorylation sites in one or both of STAT5A and CAMKK1, such as STAT5A at S780 and/or S128, and/or CAMKK1 at S548.

Optionally, said step of detecting the level of phosphorylation of one or both of TOP2A and/or KCM5C in the leukaemia cells may comprise detecting the phosphorylation of TOP2A at S1213 and/or the phosphorylation of KDM5C at S317.

In a particular aspect, the present invention provides a method of treating acute myeloid leukaemia in an individual patient suffering from acute myeloid leukaemia, comprising the steps of:
(a) obtaining a biological sample comprising leukaemia cells from the patient;
(b) (i) performing an in vitro assay to detect the expression on the surface of the leukaemia cells in the sample obtained from the patient of a group of CD markers consisting of CD11b, CD14, CD15, CD16, CD33, CD38, CD44, CD45, CD64, CD123 and HLA-DR; and/or (ii) performing an in vitro assay to detect the phosphorylation in the leukaemia cells of one or more phosphorylation sites selected from: GSK3A at pS21; PRKCD at Y313, pT507, pT295, pT218, and/or pS664 of PRKCD; STK10 at pS20 and/or pS13 of STK10; PAK1 at pS144 of PAK1; PAK2 at pS141 of PAK2; MAPK1 at Y187 and/or T185; and MAPK3 at T202 and/or Y204; and (c) where said group of CD markers is expressed at a high level on the surface of the patient's leukaemia cells, and/or one or more of said phosphorylation sites in the leukaemia cells is phosphorylated or is phosphorylated at a high level, administering midostaurin to the patient for treatment of acute myeloid leukaemia.

In another particular aspect, the invention provides a method of treating acute myeloid leukaemia in an individual patient suffering from acute myeloid leukaemia, comprising the steps of:

(a) obtaining a biological sample comprising leukaemia cells from the patient;

(b) (i) performing an in vitro assay to detect the expression on the surface of the leukaemia cells in the sample obtained from the patient of a group of CD markers consisting of CD11b, CD14, CD15, CD16, CD33, CD38, CD44, CD45, CD64, CD123 and HLA-DR; and/or (ii) performing an in vitro assay to detect the phosphorylation in the leukaemia cells of one or more MEK-related phosphorylation sites selected from MAPK1 at Y187 and/or T185 and MAPK3 at T202 and/or Y204; and/or (iii) performing an in vitro assay to detect the genotype of the leukaemia cells to determine whether there is an activating mutation in any one or more of NRAS, KRAS, HRAS or BRAF in the patient's leukaemia cells;

(c) (i) performing an in vitro assay to detect the phosphorylation in the leukaemia cells at one or more marker sites selected from STAT5A at pS780 and/or pS128, CAMKK1 at pS548, TOP2A at pS1213 and KDM5C at pS317 of KDM5C; and/or (ii) performing an in vitro assay to detect the genotype of the leukaemia cells to determine whether there is an activating mutation in FLT3 in the patient's leukaemia cells; and (d) where: (A) said group of CD markers is expressed at a high level on the surface of the patient's leukaemia cells, and/or one or more of said MEK-related phosphorylation sites in the leukaemia cells is phosphorylated or is phosphorylated at a high level, and/or there is an activating mutation in any one or more of NRAS, KRAS, HRAS or BRAF in the leukaemia cells of the patient; and (B) said marker site is not phosphorylated or is not phosphorylated at a high level in the patient's leukaemia cells, and/or there is no activating mutation in FLT3 in the patient's leukaemia cells, administering trametinib to the patient for treatment of acute myeloid leukaemia.

The present invention is illustrated with reference to the specific examples provided below, and to the figures, in which:

FIG. 1 shows heterogeneous sensitivity of AML primary cells to kinase inhibitors. (A) Cell viability of 36 AML cases as a function of ex vivo treatment with the indicated kinase inhibitors at the concentrations shown. (B) Clustering analysis of AML primary cells based on their sensitivity to 1 μM treatment with the named compounds. (C) Correlation analysis for the sensitivities of AML primary cells to treatment. (D) Sensitivity to 1 μM MEKi treatment of AML primary cells as a function of their FAB subtype. Unpaired, two-tailed Student's t-test was used to assess p-values. In (C), critical values for significant correlation in a two tailed test were r>0.329 for p<0.05(*), r>0.428 for p<0.01(), r>0.526 for p<0.001(*). All experiments were done with n=36 AML cases.

Figure 2:
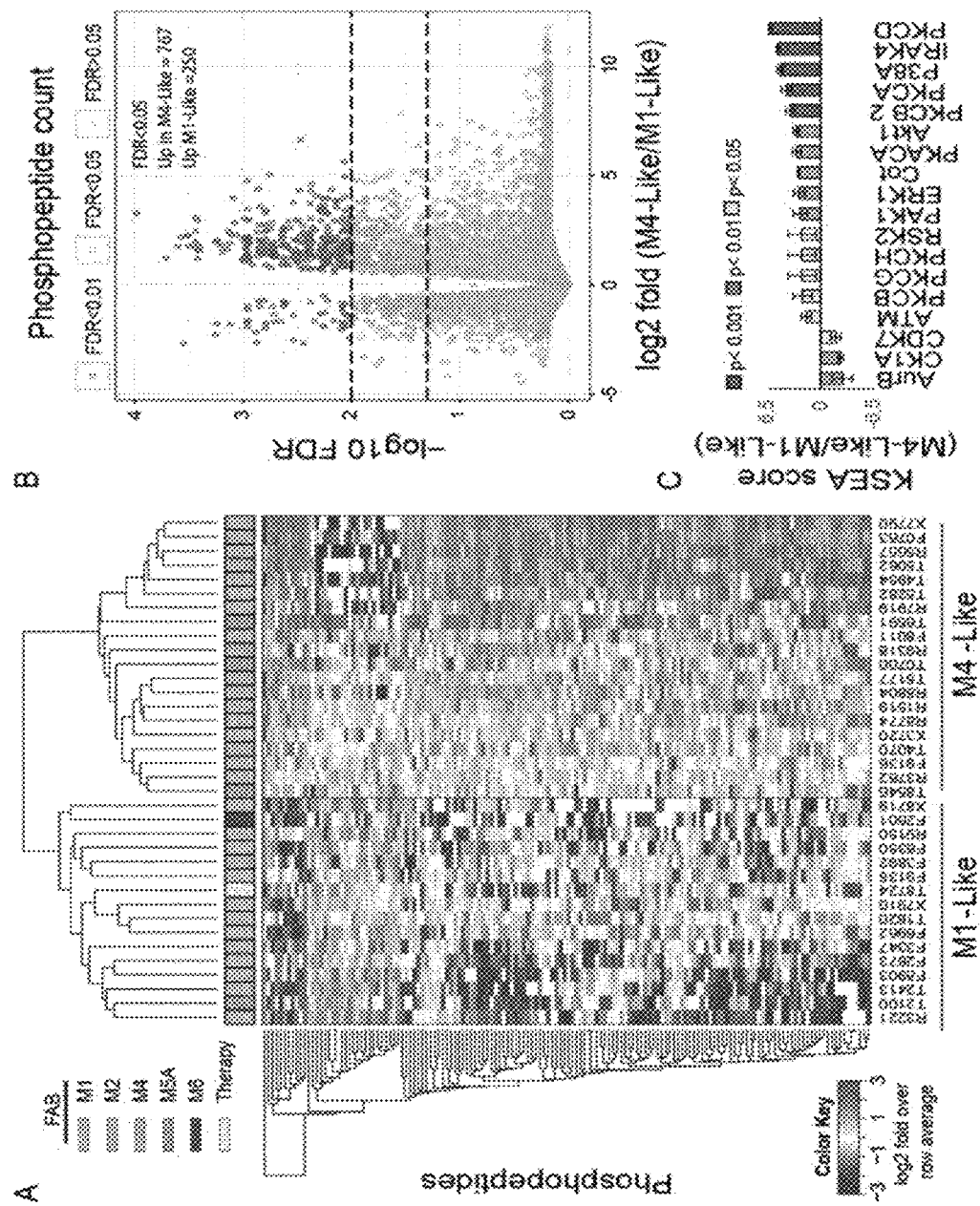

FIG. 2 shows the phosphoproteomes of FAB-M1 and FAB-M4 classify AML primary cells into groups with specific patterns of protein phosphorylation and kinase activities. (A) Hierarchical cluster analysis of the 150 phosphopeptides showing greater significant differences between FAB-M1 and FAB-M4 cases. (B) Overview of phosphopeptides significantly increased in the M1-Like and M4-Like groups. (C) KSEA inferred activity for the indicated kinases using the phosphorylation sites shown in (B). In all analysis, n=36 primary AML samples. In B, unpaired, two-tailed Student's t-test was used to calculate p-values that were adjusted using the Benjamini-Hochberg procedure (FDR). In C, hypergeometrics test was used to assess the significance of enrichment.

Figure 3:
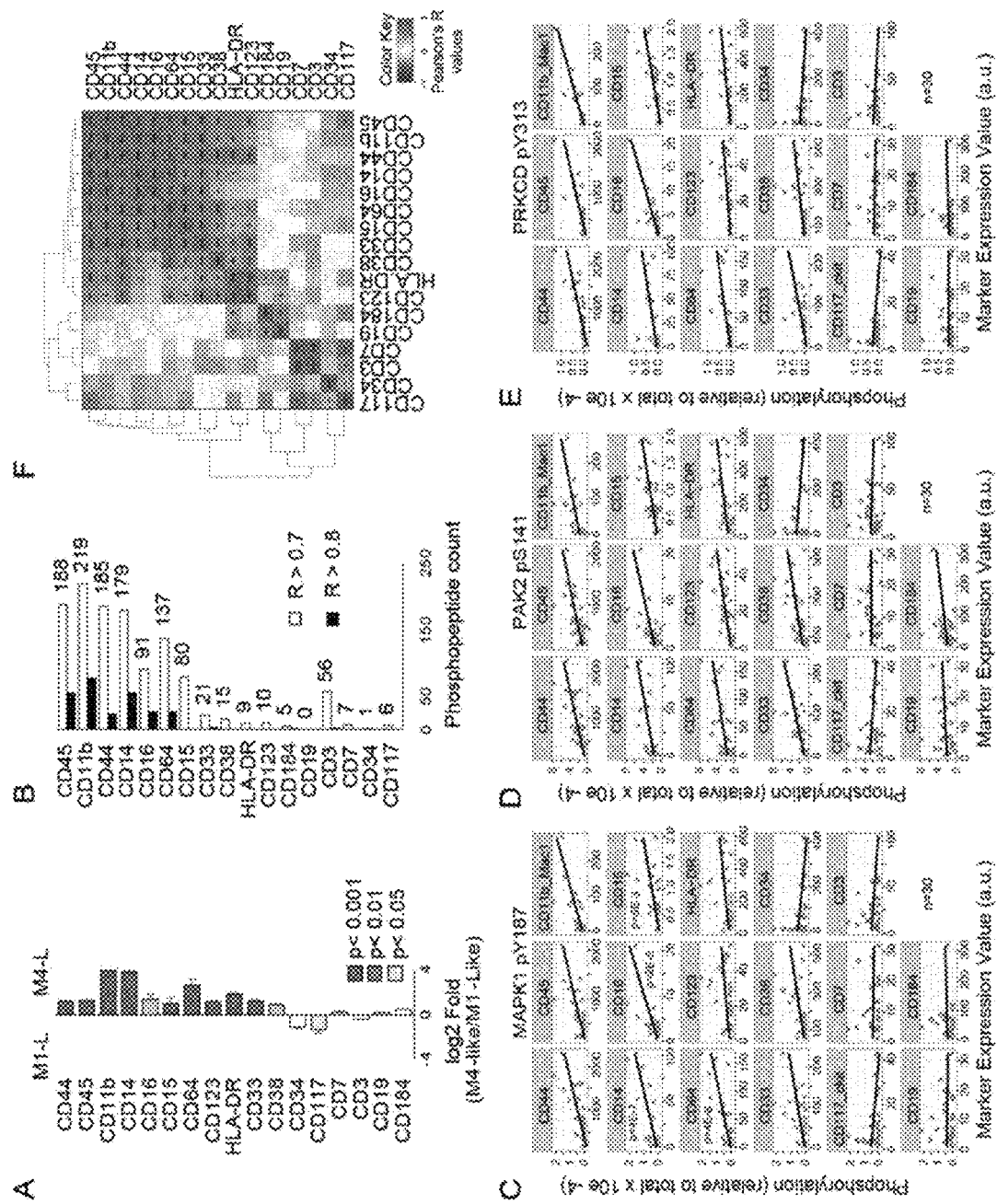

FIG. 3 shows surface expression of differentiation markers stratifies AML patients and correlates with specific patterns of protein phosphorylation. (A) Average surface expression of the indicated differentiation markers for the M1-Like and M4-Like groups. (B) Frequency of correlation between differentiation marker expression and phosphopeptide abundance. (C-E) Correlation between the phosphorylation of MAPK1 at Y187, PAK2 at S141 and PRKCD at Y313 and the surface expression of the indicated differentiation markers. (F) Pearson correlation coefficients for the expression of each differentiation marker. In all analyses, n=30 primary AML samples. In (A) p-values were assessed using unpaired, two-tailed Student's t-test. In (F), critical values for significant correlation in a two tailed test were r>0.361 for p<0.05(*), r>0.463 for p<0.01(), r>0.571 for p<0.001(*).

Figure 4:
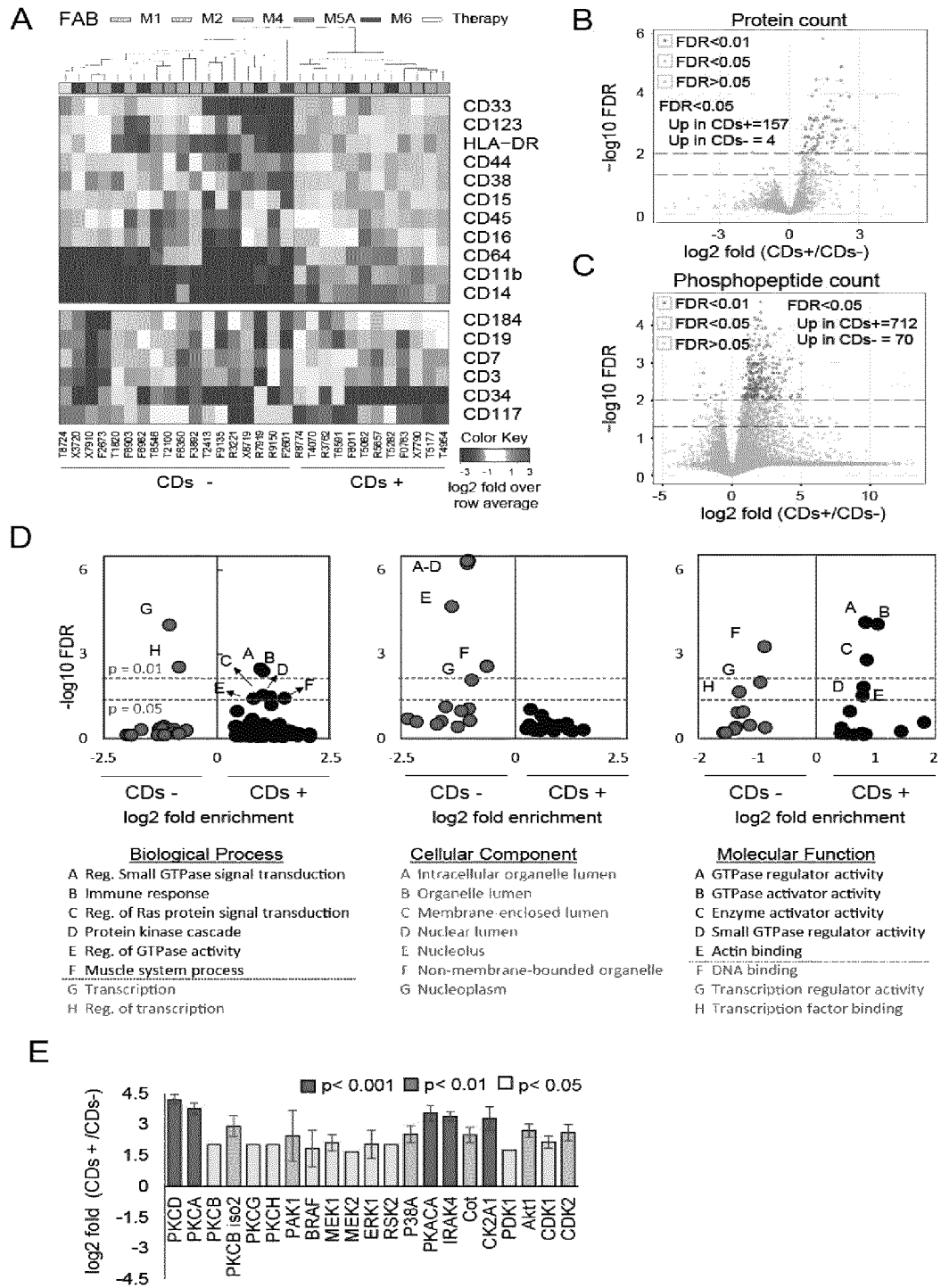

FIG. 4 shows AML cases of distinct differentiation stage present specific patterns of protein expression, protein phosphorylation and kinase activities. (A) Hierarchical clustering analysis of 30 AML cases based on the indicated differentiation markers. (B) Overview of proteins overexpression across the CDs groups. (C) Overview of phophopeptides abundances across the CDs groups. (D) Gene ontologies associated to proteins differentially phosphorylated across the CDs+ and CDs− groups. (E) KSEA estimation of average kinase activity in the CDs+ and CDs− groups. In B and C, p-values were calculated using an unpaired, two-tailed Student's t-test analysis and adjusted using Benjamini-Hochberg correction. In D and E, p-values were assessed using the hypergeometric test.

Figure 5:
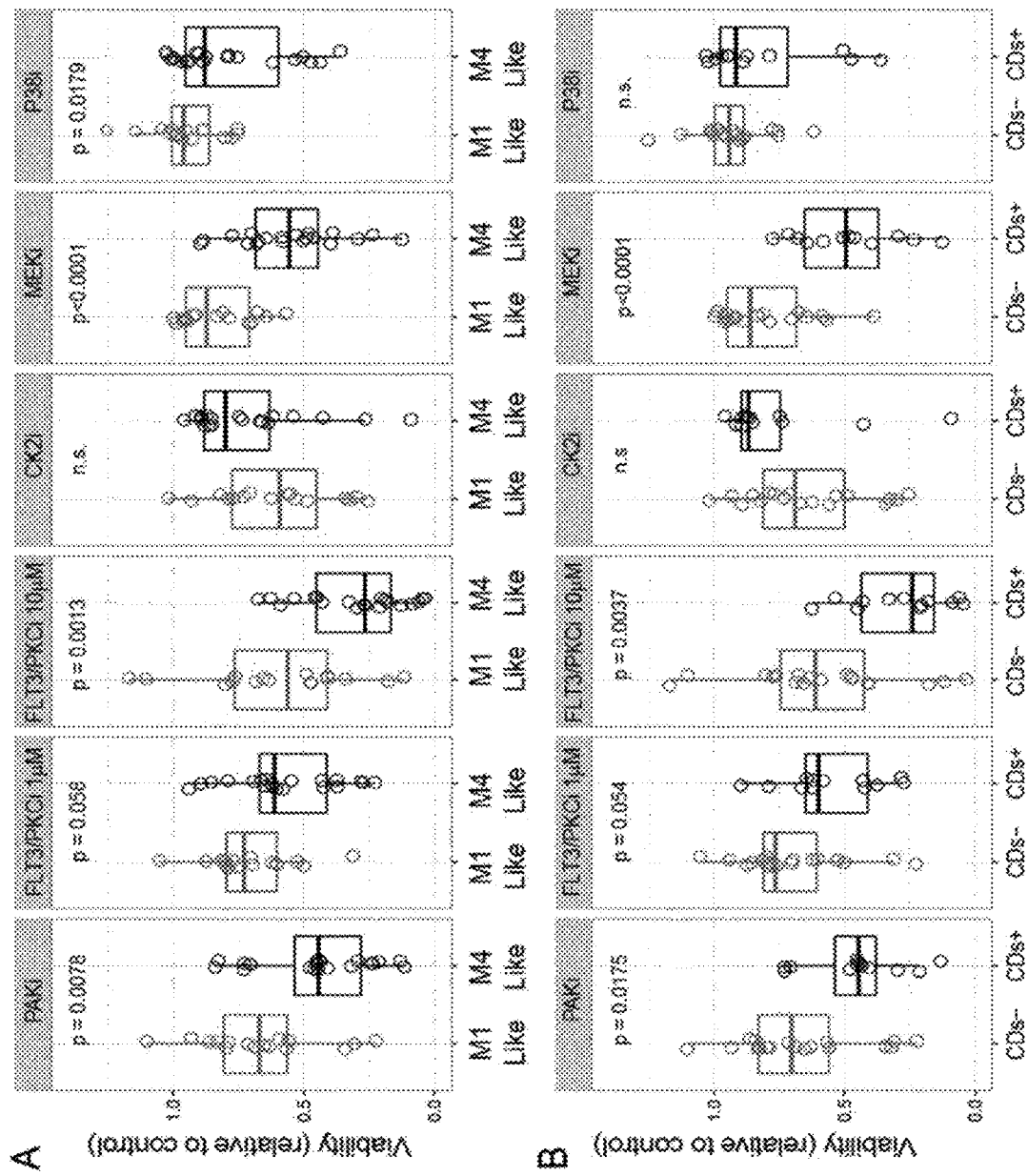

FIG. 5 shows sensitivity to kinase inhibitors as a function of AML blast differentiation. (A) Viability of primary AML samples classified as M4-Like or M1-Like (n=36) after 72h treatment with the indicated inhibitors. (B) Viability of primary AML samples classified as CDs+ or CDs− (n=30) after 72h treatment with the indicated inhibitors. Two-tailed Mann Whitney test was used to assess statistical significance.

Figure 6:
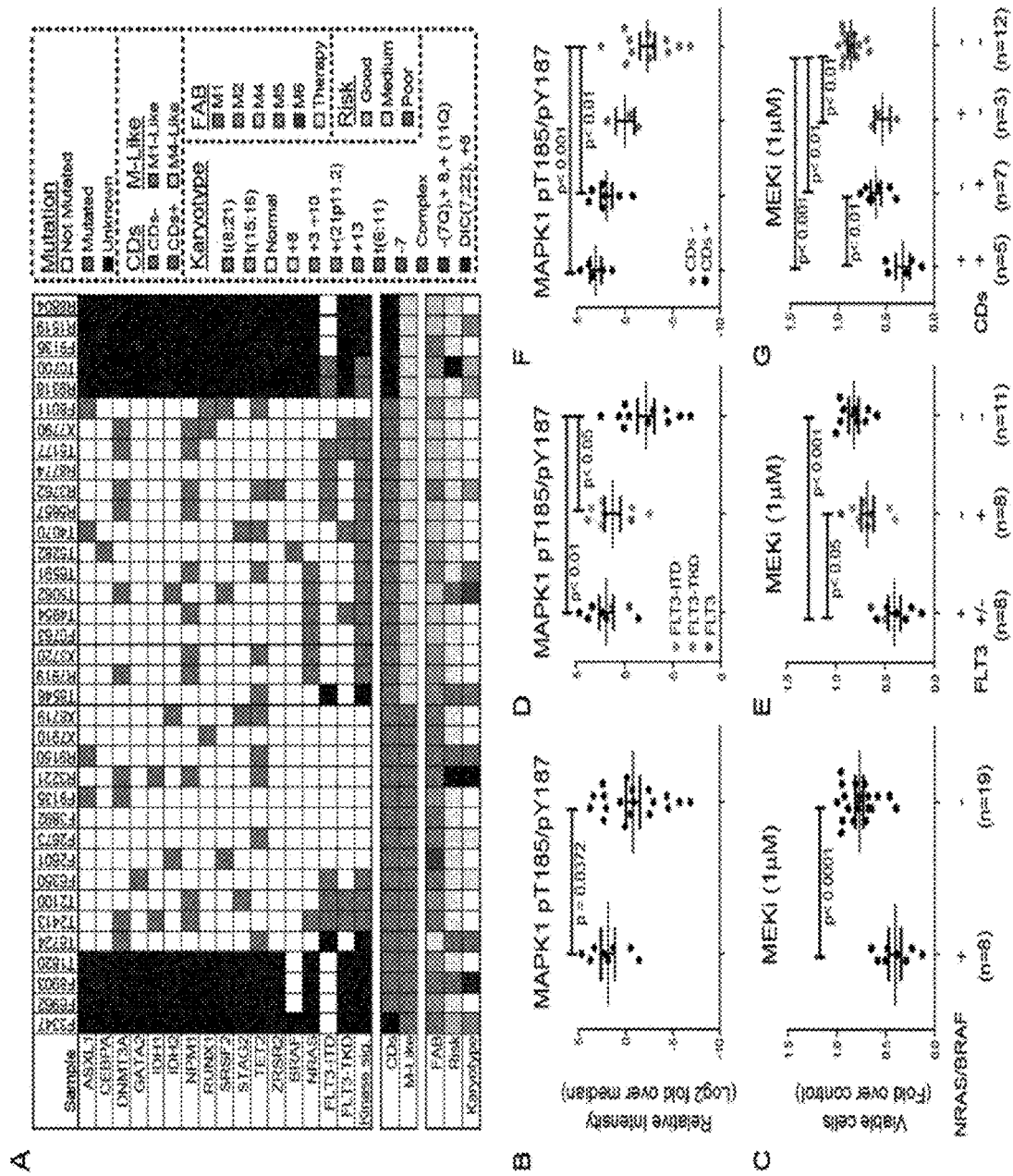

FIG. 6 shows mutation in genes linked to kinase signaling are associated to differentiation stage and to specific phosphorylation patterns. (A) Mutations for the indicated genes across the analyzed AML primary samples. Kinase sig. stands for any activating mutations in either FLT3, NRAS or BRAF. (B-G) Phosphorylation of MAPK1 and cell viability after 1 µM treatment with MEKi as a function of the indicated genotypes or phenotypes. Unpaired, two-tailed Student's t-test and one-way ANOVA followed by Tukey test was used to calculate p-values in B-C and D-E, respectively.

Figure 7:
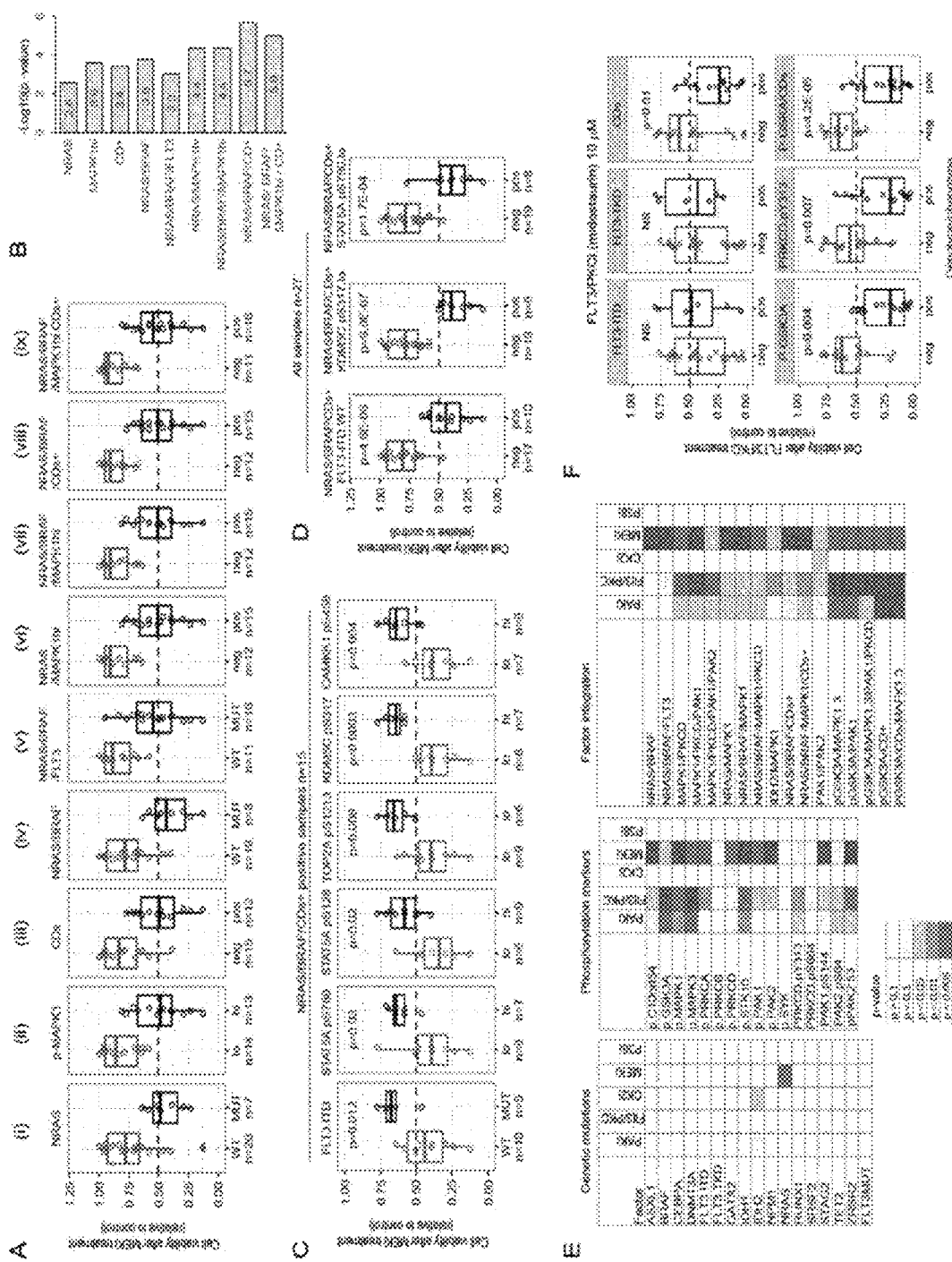

FIG. 7 shows integration of genomic, phosphoproteomics and mass cytometry data to rationalize kinase inhibitors sensitivity. (A) Viability of AML primary cells after 1 µM treatment with MEKi as a function of the indicated combinations of genotypes and phenotypes. MAPK1 phosphorylation is denoted as high (hi) and low (10) based on having a phosphorylation greater or lower than the median phosphorylation across all cases, respectively. (B) Mann Whitney p-values obtained for the comparisons performed in (A). (C) Viability of AML cells with the NRAS/BRAF/CDs+ genotype/phenotype and the indicated factor as a function of 1 µM treatment with MEKi. (D) Viability of AML primary cells after 1 µM treatment with MEKi as a function of the indicated combinations of genotypes and phenotypes. (E) Mann Whitney p-values for the viability after treatment of AML cells with 1 µM of the indicated inhibitor as a function of the presence/absence of the indicated genotype/phenotype. (F) Viability of AML cells with the indicated phenotype/genotype as a function of FLT3/PKCi treatment. Two tailed Mann Whitney test was used to assess statistical significance in (C-D, F). When numerical p-values not stated; * p<0.05;  p<0.01; * p<0.001.

Figure 8:
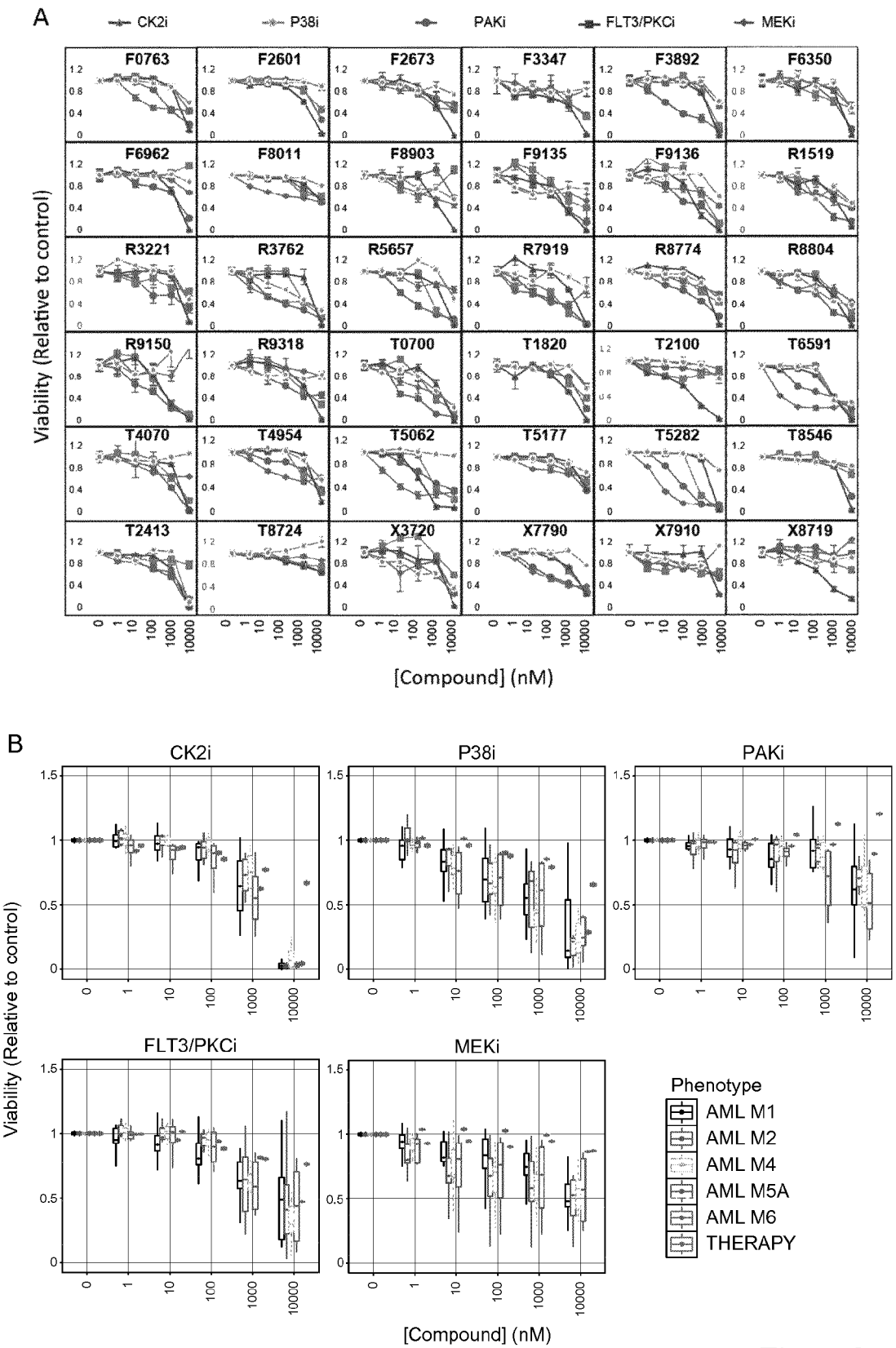

FIG. 8 shows dose response curves for cell viability of primary AML cells treated with a panel of kinase inhibitors. (A) Dose response curves to kinase inhibitors for each AML primary sample. (B) Dose response curves to kinase inhibitors for AML primary samples clustered based on the FAB subtype. Data points are mean±SD (n=3). Patient biopsies were obtained by the Barts Cancer Institute biobank with ethical consent.

FIG. 9 shows that differentiation signature based on peptide phosphorylation stratifies AML patients into groups with different patterns of phosphorylation. (A) Heatmap showing the phosphorylation of the 150 peptides used to define the M4-Like and M1-Like groups across 36 AML primary samples sorted based on FAB classification clusters. (B) Samples classified as M4-Like overphosphorylate membrane and cytoplasmic proteins liked to GTPase signaling, while M1-Like samples overphosphorylate nuclear proteins with DNA and RNA binding properties. Hypergeometric test was used to assess p-values.

FIG. 10 shows a differentiation phosphoproteomics signature classified AML primary cells in groups that present defined patterns of kinase phosphorylation and surface expression of differentiation markers. Hierarchical cluster analysis based on the 150 phosphopeptides more differentially expressed between AML cases classified as M1 or M4 FAB subtypes were used to define the M1-Like and M4-Like groups. (A) Phosphorylation sites in kinases significantly regulated (p-value<0.05) between M1-like and M4-Like groups (n=36). (B) List of surface markers quantified by mass cytometry. (C) Differentiation markers dissimilarly expressed between M1-like and M4-Like groups (n=30). Unpaired, two-tailed Student's t-test was used to assess p-values.

Figure 11:
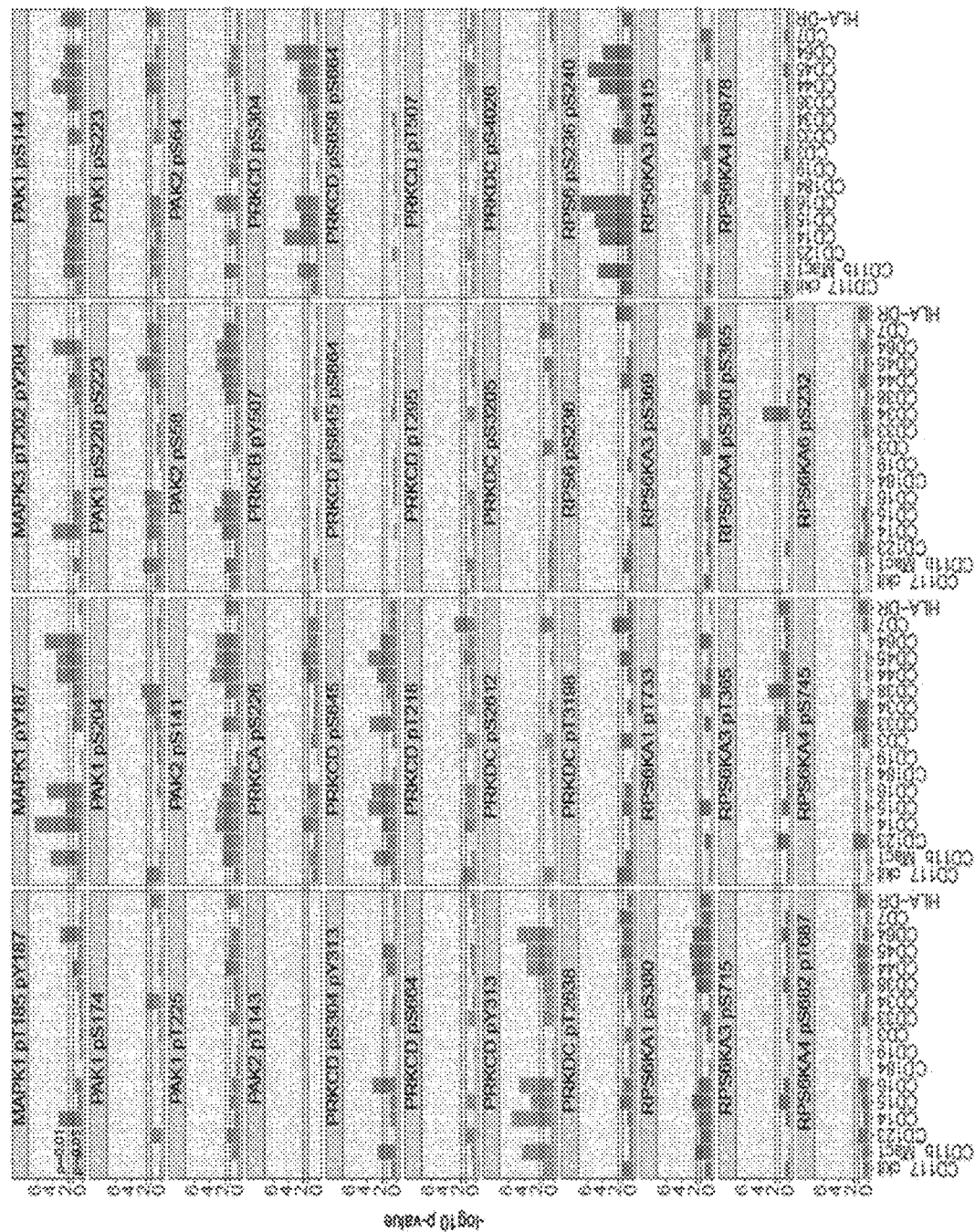

FIG. 11 shows significance of association between phosphomarkers and CD marker surface expression across 30 AML cases.

FIG. 12 shows differential protein expression and kinases differentially phosphorylated in the CDs+ and CDs− groups. Heatmaps showing proteins (A) or peptides comprised in kinases (B) whose expression or phosphorylation is significantly increased (p-value<0.05) in any of the CDs groups. Unpaired, two-tailed Student's t-test was used to assess p-values.

Figure 13:
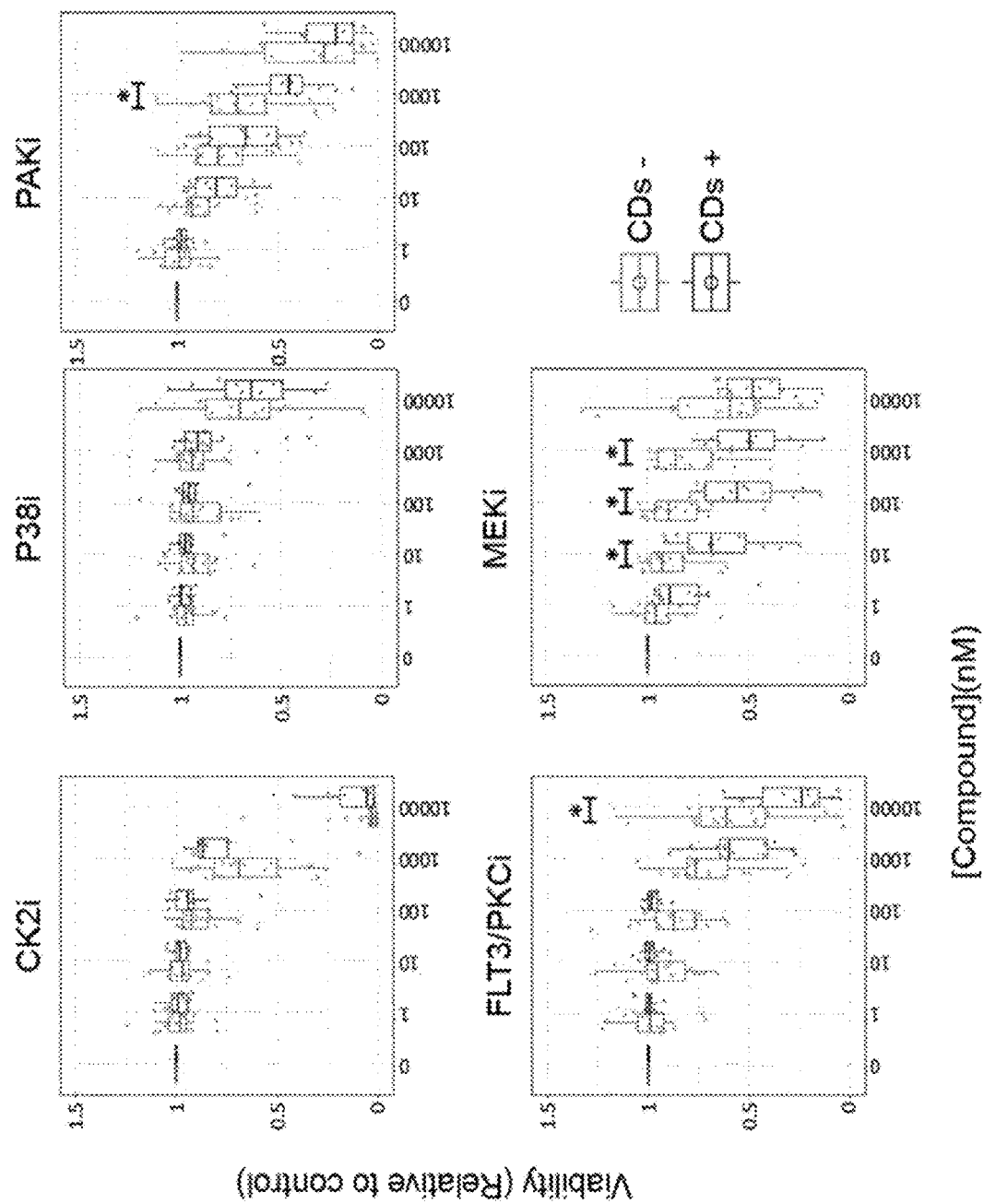

FIG. 13 shows dose response curves to kinase inhibitors for AML primary samples clustered into CDs groups. Viability of primary AML samples classified as CDs+(n=12) or CDs− (n=18) after 72h treatment with indicated inhibitors. Unpaired, two-tailed Student's t-test was used to assess p-values; * p<0.05;  p<0.01; * p<0.001

Figure 14:
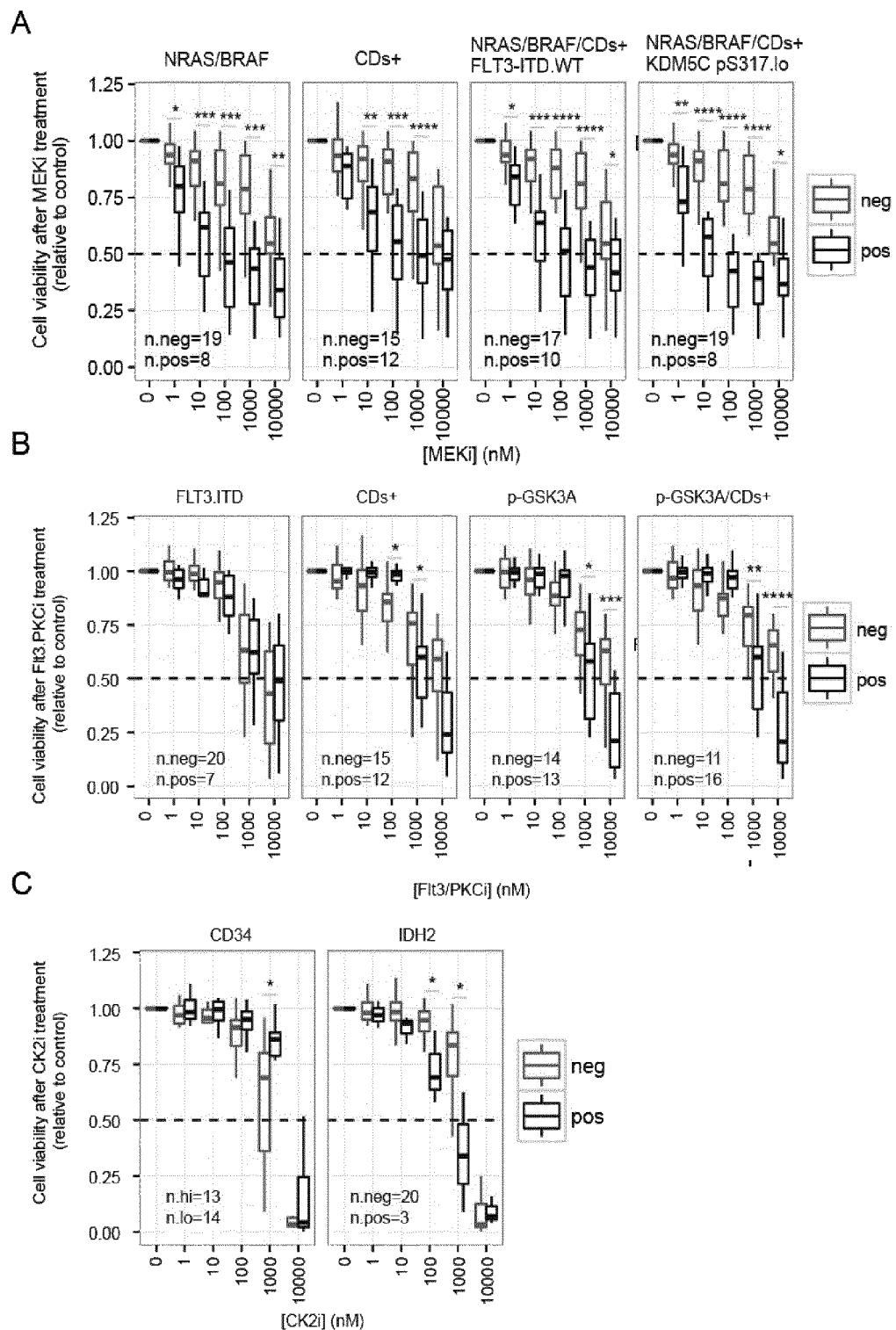

FIG. 14 shows viability of AML cells with the indicated genotype/phenotype as a function of MEKi treatment. (A) Viability of AML primary cells after treatment with MEKi. (B) Viability of AML cells after treatment with FLT3/PKCi. (C) Viability of AML primary cells after treatment with CK2i. Two tailed Mann Whitney test was used to assess p-values; * p<0.05;  p<0.01; * p<0.001.

EXAMPLES

Study Overview

The study was performed in 36 randomly selected primary samples of mononuclear cells extracted from the peripheral blood of AML patients at diagnosis. Experiments were performed as described below to determine the in vitro viability of the cells in response to treatment with inhibitors of the kinases FLT3/PKC (midostaurin, FLT3/PKCi), PAK (PF-3758309 PAKi), CK2 (silmitasertib CK2i) and MEK (trametinib, MEKi) The P38 inhibitor (P38i) TAK-715 was included as a negative control. Cells obtained from of 36 AML patients with well annotated clinical data were treated with these compounds for 72h.

Dose response curves showed that, as expected, the 36 tested samples presented heterogeneous responses to all compounds (FIGS. 1A-B and FIG. 8A). As drug response curves are difficult to interpret when treatments do not reduce viability by >50%, we used the 1 µM dose (which is expected to inhibit the intended kinase based on the compounds' reported in vitro IC50s) to define sensitivity to treatment. At the 1 µM dose, PAKi was the most potent of all the compounds tested, as it reduced the viability of 18/36 (50%) AML cases by >50% relative to DMSO control, followed by FLT3/PKCi (9/36, 25%), MEKi (8/36, 22%) and CK2i (8/36, 22%). At the same threshold, P38i treatment only reduced the viability of 3 AML cases (8%).

Clustering analysis of the cell sensitivity data showed a tendency of PAKi sensitive cells to also be sensitive to MEKi and FLT3/PKCi (FIGS. 1B-C). In contrast, the response rates to MEKi, PAKi or FLT3/PKCi were very different to those to CK2i and P38i, suggesting that PAKi, MEKi and FLT3/PKCi have very similar, albeit non-identical, modes of action, which are different from those of CK2i and P38i.

Example 1—AML Cells with a More Advanced Differentiation Status are More Responsive to Kinase Inhibitor Treatment than Less Differentiated Cells We found that M4 cells responded significantly better than M1 cells to MEKi (FIG. 1D), suggesting that AML cases of the M4 subtype were more sensitive to MEKi than those categorized as M1. This indicates that the differentiation status of the leukaemia cells may be a marker for sensitivity to kinase inhibitor therapy.

Example 2—Identification of a Phosphoproteomic Signature that is Characteristic of Differentiated Cells We investigated differences in kinase signaling between these AML subtypes. Using a mass spectrometry method as described below we identified and quantified 9,534 phosphopeptide ions in these experiments. Of these, we selected the 150 phosphorylation sites showing the most significant differences (based on Student's t-test p-values) across groups as a phosphoproteomics signature that discriminated M4 from M1 AML subtypes (FIG. 9A). Since M4 cells are more differentiated than M1, we hypothesized that this signature may be linked to the differentiation stage of the analyzed blasts. In a hierarchical clustering analysis, this phosphoproteomics signature subdivided our cohort of 36 patients into two defined groups (FIG. 2A). We termed "M1-Like" the group that included 10 of the 12 cases of the M1 subtype, and "M4-Like" the group that comprised all M4 cases (FIGS. 2A and 2B). The M1-Like and M4-Like groups consisted of 16 and 20 cases respectively.

We used ontology enrichment analysis and kinase substrate enrichment analysis (KSEA) to investigate the biological processes and signaling pathways enriched in the different groups. Analysis of phosphoproteomic differences between cases (FIG. 2B), showed that M4-Like cases had an increase in cytoplasm and membrane phosphoproteins involved in GTPase signaling, while M1-Like increased nuclear phosphoproteins with DNA and RNA binding properties. KSEA, a computational procedure that estimates individual kinase activity based on the phosphorylation of their known substrates, showed that the activities of PKC, ERK, PAK1 and P38α were enriched in the cells of the M4-Like group, whereas the activities of CDK7, CK1A and AurB were enriched in M1-Like cells (FIG. 2C). Some increased phosphorylation sites in the M4-Like group were in kinases at regulatory sites including PAK1 at S144, PAK2 at S141, MAPK1 at Y187 and RPS6KA1 at S380 (FIG. 10A). These data indicate that M4-Like cells activate kinase signaling pathways, such as PKCs, MAPK and PAK kinases, which are known to act downstream of cell surface receptors, to a greater extent than M1-Like cells.

Example 3—Identification of a Cell Surface Marker Protein Signature that is Characteristic of Differentiated Cells and Correlates with the Phosphoproteomic Signature To measure differentiation status with precision, we used mass cytometry to immunophenotype 30 cases of the 36 AML cohort (for which we had available material) by measuring the surface expression of 17 differentiation markers (FIG. 10B). We found that M4-Like cases had a greater expression of myelomonocytic differentiation markers than M1-Like cases (FIG. 3A and FIG. 10C). We next investigated if the presence of specific differentiation markers was linked to the activation of kinase signaling pathways. We found that the surface expression of CD45, CD11b, CD44, CD14, CD16, CD64 and CD15 was statistically associated ($r>0.7$, $p<0.001$) with the phosphorylation patterns of 80 to 219 sites per marker (FIG. 3B). Examples include the phosphorylation of ERK2 (MAPK1 gene) at Y187, PAK2 at S141 and PKCδ (gene PRKCD) at Y313, which were statistically associated with the expression of several differentiation markers (scatter plots for MAPK1, PAK2 and PKCδ phosphorylation sites are shown in FIGS. 3C-E and p-values of association in FIG. 11). We found the CD markers to be co-expressed (FIG. 3F). Hierarchical clustering subdivided our cohort of 30 patients in two groups, which we named CDs+ and CDs− (FIG. 4A) and which comprised of 12 and 18 cases, respectively, and which overlapped with M4-Like and M1-Like groups. In this example and in the examples below, the CDs$^+$ cells were characterized by the surface expression of a panel of cell surface markers consisting of CD33, CD123, HLA-DR, CD44, CD38, CD15, CD45, CD16, CD64, CD11b, and CD14.

Example 4—Identification of a Protein Marker Signature that is Characteristic of Differentiated Cells To investigate the biochemical differences of AML blast as a function of cell differentiation status in more detail, we compared differences in the proteomes, phosphoproteomes and kinase activities of CDs+ and CDs− AML cases. The proteomic analysis identified 2,391 proteins (FIG. 4B) and uncovered a set of proteins, previously linked to differentiation, showing greater expression in the CDs+ group relative to CDs−; including integrins, lysozyme C and other proteins linked to myeloid differentiation (FIG. 12A). Of interest, several kinases, phosphatases and signal transduction regulators were also expressed at higher levels in the CDs+ relative to CDs− cases (FIG. 12A).

As for the results of the phosphoproteomic analysis, CDs+ cases had an increase in the phosphorylation of ~3 times more sites than CDs− cases (FIG. 4C). Ontology enrichment analysis highlighted the expression of phosphoproteins linked to immune, GTPase and kinase signaling in CDs+, with CDs− cases showing an increase in the amounts of nuclear phosphoproteins and those linked to the regulation of transcription (FIG. 4D). Kinases with increased phosphorylation in the CDs+ group relative to the CDs− cases included FES at Y713, ERK1 (MAPK3) at T202/Y204, ERK2 (MAPK1) at T185/Y187, PAK1 at S144, MEK1 (MAP2K1) at S222, PAK2 at S141 and PKC-δ (PRKCD) at S645 (FIG. 12B). In line with these observations, the CDs+ group enriched the activities of several kinases relative to CDs− cells, including PKA, several isoforms of PKC, BRAF, MEK and ERK (FIG. 4E). The increased expression of integrins, survival kinases and other signaling regulators in CDs+ cells relative to CDs− cells (FIG. 12A) suggests that an increase in kinase pathway activation in more differentiated cells (FIG. 4E) is due, at least in part, to a higher expression of these signaling molecules.

Example 5—M4-Like Cells and CDs+ Cells are More Sensitive to Kinase Inhibitor Therapy Since M4-Like and CDs+ cases activated kinase survival pathways to a greater extent than M1-Like and CDs− cases, respectively, we hypothesized that there may be a difference in how the cells from these patient groups may respond to kinase inhibitors. Consistently, cell viability analysis as a function of treatment with kinase inhibitors showed that M4-Like and CDs+ cases were more sensitive than M1-Like and CDs− to 1 μM PAKi, 104 MEKi, and 10 μM FLT3/PKCi (FIG. 5A-B), which is a concentration that can inhibit PKCδ, a kinase found to be highly active in our assays (FIG. 2C, 3E, 4E). The same trends of responses were observed after treatment with other compound concentrations (FIG. 13). There were no differences between the responses to the CK2i or P38i across groups (FIG. 5A-B). Together, phosphoproteomics and differentiation marker expression stratified AML patients into groups with markedly different patterns of kinase activities and sensitivities to FLT3/PKC, PAK and MEK inhibitors. These results therefore suggest the existence of a link between differentiation, kinase-driven survival pathway activity, and the sensitivity of AML cells to kinase inhibitors.

Example 6—Mutational Status as a Marker of Kinase Inhibitor Sensitivity

To investigate the mechanisms that could contribute to the pharmacological and biochemical differences observed in AML of dissimilar differentiation phenotypes, we sequenced in our sample cohort the 25 most frequently mutated genes in AML. We found that 15 of these genes were mutated in at least 1 of the 27 cases included in the analysis (FIG. 6A). Interestingly, genes with roles in kinase signaling, including NRAS, BRAF and FLT3, were more frequently mutated in cells of the CDs+ group (FIG. 6A, p=0.008 by hypergeometric test).

We found that cells with mutated NRAS or BRAF increased the phosphorylation of MAPK1 (ERK2) at T185 and Y187, an activity marker for the RAS/MEK/ERK pathway (FIG. 6B). Consistent with published studies, we found that mutations on those genes were also significantly associated with the sensitivity of the cells to MEKi (FIG. 6C). Cells with FLT3 mutations (in a NRAS/BRAF WT background) also showed relatively high RAS/MEK/ERK pathway activity (as assessed by MAPK1 phosphorylation—FIG. 6D), although these were not more sensitive to MEKi than cells WT for FTL3, NRAS and BRAF (FIG. 6E), suggesting that the genetic background associated to pathway activation influences responses to pathway inhibition. Also of interest, CDs+ cases negative for NRAS/BRAF mutations showed high RAS/MEK/ERK pathway activation relative to CDs− samples (FIG. 6F) and were more sensitive to MEKi than the undifferentiated cases of the same NRAS/BRAF genotype (FIG. 6G).

Example 7—Mutational Status and Differentiation Status as a Combined Marker of Kinase Inhibitor Sensitivity In order to rationalize responses further, we performed a systematic analysis integrating the cells' mutational profiles with the mass spectrometry and mass cytometry data. Cells with mutated NRAS, high MAPK1 phosphorylation or positive for CDs+ were more sensitive to MEKi than cells WT for NRAS, low for MAPK1 phosphorylation or negative for the CDs phenotype, respectively (FIG. 7A(i-iv)). Cells with the NRAS/BRAF/FLT3-ITD genotypes were not more sensitive to MEKi than cells with just either NRAS or BRAF mutations (FIG. 7A(v)). In contrast, the 15 cases positive for either NRAS/BRAF/CDs+ were on average more sensitive to MEKi than cells without this molecular signature (FIG. 7A(vi-ix)).

To assess the significance of the differences in MEKi sensitivities as a function of the different molecular markers, we plotted the p-values of the comparisons illustrated in FIG. 7A. Combining the NRAS/BRAF/CDs+ signature produced the most significant difference with a $\log_{10}$ p-value of −5.7, followed by the NRAS/BRAF/MAPK1hi/CDs+ signature whose $\log_{10}$ p-value was −5.0 (FIG. 7B). These results suggest that AML cells can activate the MEK/ERK pathway by either mutations on NRAS/BRAF or by the surface expression of CD markers, consequently rendering them more sensitive to MEKi treatment than cells with WT genes or low differentiation status.

Although cases with either NRAS/BRAF mutations or the CDs+ phenotype (NRAS/BRAF/CDs+ cases) were highly sensitive to MEKi, 8 out of 15 cases with this signature demonstrated a viability>50% after treatment (FIG. 7A(viii)). To investigate the reasons for these differences in responses within the NRAS/BRAF/CDs+ cases, we compared mutation status and the phosphoproteome in the 15 cases positive for NRAS/BRAF/CDs+. Within these 15 cases, we found that FLT3-ITD positive cells were significantly more resistant to MEKi than cells without this mutation (p=0.012, FIG. 7C). Several phosphorylation markers were also found to be associated with responses to MEKi within the NRAS/BRAF/CDs+ cases, including those at STAT5A S780, STAT5A S128, TOP2A S1213, KDM5C S317 and CAMKK1 S458 (FIG. 7C), suggesting that cells with the NRAS/BRAF/CDs+ signature but relatively resistant to MEKi use FLT3-driven pathways to proliferate, which include STAT5[29]. Accordingly, samples that were positive for NRAS/BRAF/CDs+ and negative for FLT3-ITD or with low STAT5A or KDM5C phosphorylation were more sensitive to 1 µM MEKi than the other cells (FIG. 7D), with essentially all NRAS/BRAF/CDs+ cases that presented low KDM5C phosphorylation being sensitive (viability<50%) to MEKi treatment (FIG. 7D, middle panel). In addition, we found that NRAS/BRAF/CDs+ cases that were negative for FLT3-ITD or low for KDM5C phosphorylation were also more sensitive to other concentrations of MEKi, and this difference was greater than when considering NRAS/BRAF of CDs status alone (FIG. 14A).

To identify determinants of sensitivity to inhibitors other than MEKi, we compared sensitivity to the compounds as a function of mutational status, phosphorylation marker expression, or a combination of the two (FIG. 7E). We found that NRAS mutation was the only strong genomic determinant of sensitivity to MEKi with IDH2 mutations showing a small (p~0.03) effect on responses to CK2i (FIG. 7E left panel). Surprisingly, FLT3-ITD status did not have an effect on the responses of cells to the FLT3/PKCi (FIG. 7F and FIG. 14B). In contrast, several phosphorylation markers including, those on protein kinases C isoforms (gene names PRKCA, PRKCB and PRKCD), STK10, GSK3A and PAK1/2 and on the platelet membrane receptor Gi24 (C10orf54), were found to be associated with responses to PAKi, FLT3/PKCi and MEKi (FIG. 7E middle panel). Integration of genomic or CDs markers with phosphorylation data increased the significance (decreased p-values) of the associations (FIG. 7 right panel). For example, samples positive for either CDs or phosphorylation on GSK3A or PCKδ were more sensitive to FLT3/PKCi than other cases (FIG. 7F and FIG. 14B). As for CK2i, there was a small association between CD34 expression or IDH2 mutation and sensitivity to this compound, although the effect was small (FIG. 14C). Taken together, our results suggest that integration of differentiation status (as defined by CD marker expression) with genomic and phosphoproteomics signatures produces groups of AML cases characterized by their degree of sensitivity to MEKi and FLT3/PKCi.

Example 8—a Companion Diagnostic Test for Assessing Suitability of AML Patients for Treatment with Midostaurin Peripheral blood or bone marrow samples were obtained from patients suffering from acute myeloid leukaemia.

Mononuclear leukaemia cells were extracted from these samples and assays were performed on the cells as described herein in order to detect:
  (i) surface expression of a group of CD markers consisting of CD11b, CD14, CD15, CD16, CD33, CD38, CD44, CD45, CD64, CD123 and HLA-DR; and/or
  (ii) a high level of phosphorylation in the leukaemia cells of the patient at any one or more of pS21 of GSK3A; pY313, pT507, pT295, pT218, and/or pS664 of PRKCD; pS20 and/or pS13 of STK10; pS144 of PAK1; pS141 of PAK2; Y187 and/or T185 of MAPK1; and T202 and/or Y204 of MAPK3.

In step (ii), a high level of phosphorylation was identified where the phosphorylation at the reference site was higher than the average phosphorylation at that site, calculated across a plurality of patient samples.

Patients whose cells were positive for either (i) or (ii) were identified as suitable for treatment with midostaurin.

Example 9—a Companion Diagnostic Test for Assessing Suitability of AML Patients for Treatment with Trametinib Peripheral blood or bone marrow samples were obtained from patients suffering from acute myeloid leukaemia. Mononuclear leukaemia cells were extracted from these samples and assays were performed on the cells as described herein in order to detect:
  (a) (i) surface expression on the leukaemia cells of the patient of a group of CD markers consisting of CD11b, CD14, CD15, CD16, CD33, CD38, CD44, CD45, CD64, CD123 and HLA-DR; and/or
    (ii) a high level of phosphorylation in the leukaemia cells of the patient at any one or more of Y187 and/or T185 of MAPK1; and T202 and/or Y204 of MAPK3;
    (iii) activating mutations in any one or more of NRAS, KRAS, HRAS or BRAF in the leukaemia cells of the patient; and
  (b) (i) a high level of phosphorylation at one or more of pS780 and pS128 of STAT5A, pS548 of CAMKK1, pS1213 of TOP2A and pS317 of KDM5C; and/or
    (ii) the absence of any activating mutations in FLT3 in the leukaemia cells of the patient.

In steps (a)(ii) and (b)(i), a high level of phosphorylation was identified where the phosphorylation at the reference site was higher than the average phosphorylation at that site, calculated across a plurality of patient samples.

Patients whose cells were positive for both (a) and (b) were identified as suitable for treatment with trametinib.

Discussion

A central goal of targeted therapy is to identify actionable patient-specific pathways that can direct effective personalized treatments. In this study, we found that differentiation status determined the extent and/or nature of kinase pathway activation across AML samples. Some of the surface differentiation markers (e.g., CD45, and CD123) are membrane receptors or have roles in the recognition of extracellular signals, which are transduced and propagated intracellularly by protein kinase cascades. Cells positive for these CD markers had higher expression of proteins associated with myelomonocytic differentiation and kinase signaling relative to CDs– cells, and consequently presented an increase in the phosphorylation and activation of pro-survival kinases (FIGS. 2 to 4), which was translated into an increased sensitivity in how these cells responded to treatments with PAKi, midostaurin and trametinib (FIG. 5).

The integration of mass spectrometry and cytometry data with recurrent mutations present AML showed that, consistent with other studies[14], activating mutations in NRAS were linked to a higher ERK (MAPK) activity and conferred sensitivity MEKi (FIG. 6C-D). In our patient cohort, NRAS mutations seemed to be the only clear genomic determinant of responses when considered in isolation, and surprisingly, neither FLT3-ITD nor FLT3-TKD mutations were associated with the responses to midostaurin (FIG. 7F). Our data suggest that the RAS/MEK/ERK pathway may be activated in AML by either the presence of NRAS/BRAF activating mutations or by signals emanating from upstream cell surface CD markers or associated receptors. Thus MEKi treatment was more likely to reduce AML cell viability in cases positive for at least one of these markers (FIG. 7B).

However, despite the clear contribution of RAS/MEK/ERK activation to the extent of responses to MEKi, only ~50% (7/15) of cases positive for RAS/MEK/ERK activation showed high responses to MEKi. We found that cases that were relatively resistant to MEKi, despite activating the RAS/MEK/ERK pathway, possessed the FLT3-ITD genotype and had high levels of phosphorylated regulatory proteins, including STAT5A, KDM5C and the topoisomerase 2A at S1213, a site that regulates the activity of the enzyme (FIG. 7). Thus, AML cell populations that responded well to MEKi showed a high activity of the target pathway (RAS/MEK/ERK) together with a low activity of the FLT3/STAT pathway (FIG. 7D), which is known to sustain viability and proliferation of primary AML cells by acting in parallel to RAS/MEK/ERK signaling.

Our results therefore suggest two distinct mechanisms of intrinsic resistance to MEK inhibition. The first one occurs in cells that are not addicted to the pro-survival actions of MEK because these have low RAS/MEK/ERK pathway activity. The second mechanism occurs in cells which, albeit having a highly active RAS/MEK/ERK, bypass MEK inhibition because the FLT3/STAT5 axis acts as a compensatory mechanism.

Pemovska et al. observed that 36% of AML patient samples were more sensitive to trametinib than mononuclear cells from healthy donors, and we found that 22% of our cases showed >50% reduction in viability as a result of treatment with this drug (FIG. 1). Thus, trametinib, a drug already approved by the FDA for the treatment of melanoma, is worth consideration for repurposing to treat the 20-35% of AML cases predicted to respond to such treatment.

As for the PAKi and FLT3/PKCi, we did not find an association between genetic alterations and responses to these compounds (FIG. 7). We observed, however, that cells with a more differentiated phenotype and those with high phosphorylation of GSK3A and PKCδ responded better to midostaurin than cells with low phosphorylation on these markers (note that PKCδ is upstream of GSK3A [Ref[38]]). Our results therefore suggest that the mode of action of midostaurin (the FLT3/PKCi used in this work), which is in later stages of clinical development[39,40], involves the inhibition of PKCδ, a known target of this drug.

In conclusion, we found that AML cells activate the receptor tyrosine kinase signaling network during differentiation, resulting in a marked increase in the activity of pro-survival pathways regulated by MEK and PKC isoforms. The combination of target and parallel kinase pathway activation (caused by genetic and non-genetic events) determined the extent by which AML cells respond to treatments with trametinib or midostaurin.

Methods
Study Design

The study was performed in 36 primary samples of mononuclear cells extracted from the peripheral blood of AML patients at diagnosis. Samples were randomly selected from the BCI tissue bank collection. Initially, 45 samples were included in the study but nine were later excluded because these were not viable in the ex-vivo experiments. Material availability allowed proteomics and mass cytometry analysis of 30 samples and DNA sequencing of 27 samples. Ex-vivo drug testing was performed in quadruplicate sampling replicates and viability values averaged and expressed relative to vehicle control.

Patients gave informed consent for the storage and use of their blood cells for research purposes. Experiments were performed in accordance with the Local Research Ethics Committee.

Mass Spectrometry

Cells were lysed and proteins digested using trypsin as previously described in Wilkes E H, Terfve C, Gribben J G, Saez-Rodriguez J, Cutillas PR. Empirical inference of circuitry and plasticity in a kinase signaling network. *Proc Natl Acad Sci USA*. 2015; 112(25):7719-7724.

LC-MS/MS identification and quantification of peptides and phosphopeptides was performed in an orbitrap mass spectrometer (Q-Exactive Plus). Normalized quantitative data were used to calculate fold changes between groups and statistical significance (assessed by Student's t-test). The mass spectrometry proteomics data have been deposited to the ProteomeXchange Consortium via the PRIDE partner repository with the dataset identifier PXD005978 and DOI 10.6019/PXD005978. See Vizcaino JA, Csordas A, Del-Toro N, et al. 2016 update of the PRIDE database and its related tools. *Nucleic Acids Res.* 2016; 44(22): 11033.

Bioinformatics

Inference of kinase activities from the phosphoproteomics data was performed using Kinase substrate enrichment analysis (KSEA) as described in Casado P, Rodriguez-Prados J C, Cosulich S C, et al. Kinase-substrate enrichment analysis provides insights into the heterogeneity of signaling pathway activation in leukemia cells. *Sci Signal.* 2013; 6(268):rs6.

DAVID software (https://david.ncifcrf.gov/) was used to determine the enrichment of gene ontologies (GO), which were considered enriched when the Bonferroni's corrected p-values were <0.05. Hierarchical clusters were constructed within the R statistical computing environment (3.2.3) using the Euclidean distance metric in the heatmap2 function.

Mass Cytometry

Primary cells were coated with metal conjugated antibodies, as indicated by the manufacturer. and analyzed on a CyTOF2 mass cytometer (Fluidigm). Data were normalized using the normalizer within the DVS Sciences CyTOF Instrument Control Software (v 6.0.626)

Viability Assay

Ex-vivo drug testing of AML primary cells was as previously described in Casado P, Rodriguez-Prados J C, Cosulich S C, et al. Kinase-substrate enrichment analysis provides insights into the heterogeneity of signaling pathway activation in leukemia cells. *Sci Signal.* 2013; 6(268):rs6. Briefly, cells were re-suspended in MS-5 conditioned IMDM medium, seeded in 96 well plates and treated with vehicle or 1 to 10000 nM of the indicated inhibitors for 72h. Cells were stained with Guava ViaCount reagent and cell number and viability was measured. Flow cytometry data were analyzed using CytoSoft (v2.5.7).

Panel Sequencing

Target enrichment of a 25 gene myeloid panel was achieved using an in-house True SeqCustom Amplicon (TSCA) design (Illumina, San Diego, USA).

Statistical Analysis

Statistical anlaysis was performed in R (version 3.2.3), Micorsoft Excel 2013 or Prism (version 5.4). The p-values returned from Mann Witney, Anova or Student's t-test, as indicated in the figures, were adjusted for multiple testing using the Tukey or Benjamini-Hochberg procedures as required.

Mass Spectrometry, Proteomics and Phosphoproteomics

Cell were harvested by centrifugation at 500×g at 4° C. for 5 min, washed twice with cold PBS supplemented with 1 mM $Na_3VO_4$ and 1 mM NaF, snap frozen and stored at −80C until further processing. Cell pellets were lysed in urea buffer (8M urea in 20 mM in HEPES pH 8.0 supplemented with 1 mM $Na_3VO_4$, 1 mM NaF, 1 mM $Na_4P_2O_7$ and 1 mM sodium β-glycerophosphate) for 30 min and further homogenized by sonication (60 cycles of 30s on 40s off; Diagenode Bioruptor® Plus, Liege, Belgium). Insoluble material was removed by centrifugation at 20.000×g for 10 min at 5° C. and protein in the cell extracts was quantified by bicinchoninic acid (BCA) analysis.

For phosphoproteome analyses, we used published methods with some modifications. See:

Gruhler A, Olsen J V, Mohammed S, Mortensen P, Faergeman N J, Mann M, et al. Quantitative phosphoproteomics applied to the yeast pheromone signaling pathway. Molecular & cellular proteomics: MCP 2005; 4(3):310-27 doi 10.1074/mcp.M400219-MCP200.

Larsen M R, Thingholm T E, Jensen ON, Roepstorff P, Jorgensen T J. Highly selective enrichment of phosphorylated peptides from peptide mixtures using titanium dioxide microcolumns. Molecular & cellular proteomics: MCP 2005; 4(7):873-86 doi 10.1074/mcp.T500007-MCP200.

Montoya A, Beltran L, Casado P, Rodriguez-Prados JC, Cutillas PR. Characterization of a TiO(2) enrichment method for label-free quantitative phosphoproteomics. Methods 2011; 54(4):370-8 doi 10.1016/j.ymeth.2011.02.004

Briefly, 250 μg of protein were reduced and alkylated by sequential incubation with 10 mM DTT and 16.6 mM iodoacetamyde for 1h. The urea concentration was diluted to 2M with 20 mM HEPES (pH 8.0) and 80 μl of conditioned trypsin beads [(50% slurry of TLCK-trypsin (Thermo-Fisher Scientific; Cat. #20230)] conditioned with 3 washes of 20 mM HEPES (pH 8.0)) were added and the samples incubated for 16h at 37° C. with agitation. Trypsin beads were removed by centrifugation at 2,000×g for 5 min at 5° C. For phosphoproteomics analyses, 100 μg of protein were used.

Following trypsin digestion, peptide solutions were desalted using 10 mg OASIS-HLB cartridges (Waters, Manchester, UK). Briefly, OASIS cartridges were accommodated in a vacuum manifold (−5 mmHg), activated with 1 mL ACN and equilibrated with 1.5 mL washing solution (1% ACN, 0.1% TFA). After loading the samples, cartridges were washed with 1 mL of washing solution. For phosphoproteomics analyses, peptides were eluted with 500 μl of glycolic acid buffer 1 (1 M glycolic acid, 50% ACN, 5% TFA) and subjected to phosphoenrichment. For proteomics analyses peptides were eluted with 500 μL of ACN solution (30% ACN, 0.1% TFA), dried in a speed vac (RVC 2-25, Martin Christ Gefriertrocknungsanlagen GmbH, Osterode am Harz, Germany) and stored at −80° C.

Phosphopeptides were enriched using $TiO_2$ (GL Sciences) as previously described with some modifications (4).

Sample volumes were normalized to 1 mL using glycolic acid buffer 2 (1 M glycolic acid, 80% ACN, 5% TFA), 50 µL of $TiO_2$ beads (50% slurry in 1% TFA) were added to the peptide mixture, incubated for 5 min at room temperature with agitation and centrifuged for 30s at 1500×g. For each sample, 80% of the supernatant was transfer to fresh tubes and stored in ice and the remaining 20% used to resuspend the bead pellets that were loaded into an empty prewashed PE-filtered spin-tips (Glygen, MD, USA) and packed by centrifugation at 1500×g for 3 min. After loading the remaining volume of the supernatant by centrifugation at 1500×g for 3 mim, spin tips were sequentially washed with 100 µL of glycolic acid buffer 2, ammonium acetate buffer (100 mM ammonium acetate in 25% ACN) and 10% ACN by RT centrifugation for 3 min at 1500×g. For phosphopeptide recovery, the addition 50 µL of 5% ammonium water followed by centrifugation for 5 min at 1500×g was repeated 4 times. Eluents were snap frozen in dry ice, dried in a speed vac and peptide pellets stored at −80° C.

For phosphoproteomics, peptide pellets were resuspended in 12 µL of reconstitution buffer (20 fmol/µL enolase in 3% ACN, 0.1% TFA) and 5.0 µL were loaded onto an LC-MS/MS system consisting of a Dionex UltiMate 3000 RSLC directly coupled to an Orbitrap Q-Exactive Plus mass spectrometer (Thermo Fisher Scientific). For proteomics, pellets were resuspended in reconstitution buffer (0.5 µg/µL) and 2 µL were injected. The LC system used mobile phases A (3% ACN: 0.1% FA) and B (100% ACN; 0.1% FA). Peptides were trap in a µ-pre-column (catalog no 160454) and separated in an analytical column (Acclaim PepMap 100; catalog no 164569). The following parameters were used: 3% to 23% B gradient for 120 min and a flow rate of 0.3 µL/min.

As they eluted from the nano-LC system, peptides were infused into the online connected Q-Exactive Plus system operating with a 2.1s duty cycle. Acquisition of full scan survey spectra (m/z 375-1,500) with a 70,000 FWHM resolution was followed by, data-dependent acquisition in which the 20 most intense ions were selected for HCD (higher energy collisional dissociation) and MS/MS scanning (200-2,000 m/z) with a resolution of 17,500 FWHM. A 30 s dynamic exclusion period was enabled with an exclusion list with 10 ppm mass window. Overall duty cycle generated chromatographic peaks of approximately 30 s at the base, which allowed the construction of extracted ion chromatograms (XICs) with at least 10 data points. The raw files for the extra samples were also uploaded into PRIDE.

Peptide Identification and Quantification

Mascot Daemon 2.5.0 was used to automate peptide identification from MS data. Peak list files (MGFs) from RAW data were generated with Mascot Distiller v2.5.1.0 and loaded into the Mascot search engine (v2.5) in order to match MS/MS data to peptides (Perkins D N, Pappin DJ, Creasy DM, Cottrell J S. Probability-based protein identification by searching sequence databases using mass spectrometry data. Electrophoresis 1999; 20(18):3551-67). The searches were performed against the SwissProt Database (SwissProt_2012oct.fasta for proteomics or uniprot_sprot_2014_08.fasta for phosphoproteomics analysis) with a FDR of −1% and the following parameters: 2 trypsin missed cleavages, mass tolerance of ±10 ppm for the MS scans and ±25 mmu for the MS/MS scans, carbamidomethyl Cys as a fixed modification, PyroGlu on N-terminal Gln and oxidation of Met as variable modifications. For phosphoproteomics experiments Phosphorylation on Ser, Thr, and Tyr was also included as variable modifications. The in-house developed Pescal software was used for label-free peptide quantification (6), XICs for all the peptides identified across all samples were constructed with ±7 ppm and ±2 min mass and retention time windows, respectively. Peak areas from all XICs were calculated. Undetectable peptides were given an intensity value of 0. Values of 2 technical replicates per sample were averaged and intensity values for each peptide were normalized to total sample intensity.

Mass Cytometry

Mass cytometry was used to characterize CD markers in AML cells (Bandura DR, Baranov I, Ornatsky OI, Antonov A, Kinach R, Lou X, et al. Mass cytometry: technique for real time single cell multitarget immunoassay based on inductively coupled plasma time-of-flight mass spectrometry. Analytical chemistry 2009; 81(16):6813-22). Cells ($4 \times 10^6$) were transferred to fresh tubes, washed twice with PBS and incubated with 1× Cell-ID™ Cisplatin solution (Fluidigm; Cat. 201064) for 5 min at RT. Cells were washed with Maxpar Cell Staining buffer and pellets were resuspended and incubated with 50 µL of 20 µg/mL HAG (human γ-Globulins, Sigma-Aldrich; Cat. G4386-1G) for 20 min at RT. After adding 50 µL of antibody mix (1/50 dilution of each antibody; Suplemental Table1), samples were incubated for 30 min at RT. The cells were then washed twice with Maxpar Cell Staining buffer, pellets were resuspended in Fix and Perm Buffer and left overnight at 4° C. Next day, Ir intercalator was added to a final concentration of 1× and samples were incubated for 20 min at RT. Permeabilized cells were washed twice with Maxpar Cell Staining buffer and twice with Maxpar water.

The following antibodies were used in mass cytometry assays as described below:

| Antigen | Determinant | Clone | Metal |
|---|---|---|---|
| CD19 | Co-receptor for CD21 | HIB19 | 142Nd |
| CD117 | Receptor Tyrosine Kinase/SCF | 104D2 | 143Nd |
| CD11b | Fibrinogen Receptor | ICRF44 | 144Nd |
| CD64 | Fc Receptor | 10.1 | 146Nd |
| CD7 |  | CD7-6B7 | 147Sm |
| CD123 | Interleukin 3 Receptor | 6H6 | 151Eu |
| CD45 | Receptor Tyrosine Phosphatase | HI30 | 154Sm |
| CD33 | Sialic Acid Receptor | WM53 | 158Gd |
| CD15 | Carbohydrate | W6D3 | 164Dy |
| CD34 | Cell-Cell Adhesion Factor | 581 | 166Er |
| CD3 | TCR Co-receptor | UCHT1 | 170Er |
| CD44 | Hyaluronic Acid Receptor | IM7 | 171Yb |
| CD38 | Synthesis of Cyclic ADP | HIT2 | 172Yb |
| HLA-DR | Antigen Presentation | L243 | 174Yb |
| CD184 | Chemokine Receptor/PSD-1 | 12G5 | 175Lu |
| CD14 | Co-activator of TLR4 | M5E2 | 160Gd |
| CD16 | Fc Receptor | 3G8 | 148Nd |

Sanger Sequencing

Primers for BRAF V600 PCR were forward 5'-TCTT-CATGAAGACCTCACAGT-3' and reverse 5'-CCA-GACAACTGTTCAAACTGA-3'. 20-50 ng of DNA was used as template and the thermal conditions were as follows: initial heating period for 15 min at 95° C., 36 cycles at 95° C. for 1 min, 55° C. for 1 min and 72° C. for 1 min, and finally 10 min at 72° C. Amplicones were sequenced by GATC Biotech (Constanza, Germany) using the forward primer. Positive cases were validated using the reverse primer.

Mass Cytometry

Mass cytometry was used to simultaneously measure the surface expression of 17 differentiation markers (CD3, CD7, CD11b, CD14, CD15, CD16, CD19, CD33, CD34, CD38, CD44, CD45, CD64, CD117, CD123, CD184, HLA-DR) in mononuclear cells extracted from the peripheral blood of 30

AML patients. Label free quantitative phosphoproteomics based on $TiO_2$ phosphoenrichment was used to quantify>5,000 phosphorylation sites in the same AML primary samples and KSEA technology was applied to infer kinase activity from the phosphoproteomics data. Gene ontology enrichment was calculated based on the genes that code for the proteins where the phosphorylation sites were detected using DAVID software. Guava EasyCyte Flow Cytometry was used to determine cell viability after the treatment of the same patient samples with 5 kinase inhibitors (PF-3758309, Midostaurin, silmitasertib, trametinib and TAK715 aiming to target the kinases PAK, Flt-3, Casein Kinase 2, MEK and P38, respectively).

The invention claimed is:

1. A method of treating an acute myeloid leukemia (AML) patient whose leukemia cells have advanced differentiation status, comprising the steps of:

administering midostaurin to an AML patient whose leukemia cells have advanced differentiation status, wherein the AML patient whose leukemia cells have advanced differentiation status is identified by having in the leukemia cells of the patient:

(i) a higher than normal expression level of a CD marker selected from the group selected of: CD11b, CD14, CD15, CD16, CD33, CD38, CD44, CD45, CD64, CD123, and HLA-DR, and (ii) the phosphorylation of one or more phosphorylation sites selected from the group consisting of: GSK3A at pS21; PRKCD at Y313; pT507, pT295, pT218, and/or pS664 of PRKCD; STK10 at pS20 and/or pS13 of STK10; PAK1 at pS144 of PAK1; PAK2 at pS141 of PAK2; MAPK1 at Y187 and/or T185; and MAPK3 at T202 and/or Y204.

* * * * *